US011839616B2

(12) United States Patent
Verkman et al.

(10) Patent No.: US 11,839,616 B2
(45) Date of Patent: *Dec. 12, 2023

(54) OCULAR PHARMACEUTICAL COMPOSITIONS

(71) Applicant: THE REGENTS OF THE UNIVERSITY OF CALIFORNIA, Oakland, CA (US)

(72) Inventors: Alan S. Verkman, San Francisco, CA (US); Marc H. Levin, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 413 days.

This patent is subject to a terminal disclaimer.

(21) Appl. No.: 16/641,621

(22) PCT Filed: Aug. 24, 2018

(86) PCT No.: PCT/US2018/048025
§ 371 (c)(1),
(2) Date: Feb. 24, 2020

(87) PCT Pub. No.: WO2019/040919
PCT Pub. Date: Feb. 28, 2019

(65) Prior Publication Data
US 2021/0154201 A1    May 27, 2021

Related U.S. Application Data

(60) Provisional application No. 62/549,872, filed on Aug. 24, 2017.

(51) Int. Cl.
*A61K 31/53*     (2006.01)
*A61K 9/00*      (2006.01)
*A61P 27/02*     (2006.01)
*A61P 27/04*     (2006.01)

(52) U.S. Cl.
CPC ............ *A61K 31/53* (2013.01); *A61K 9/0048* (2013.01); *A61P 27/04* (2018.01)

(58) Field of Classification Search
None
See application file for complete search history.

(56) References Cited

U.S. PATENT DOCUMENTS

| | | | |
|---|---|---|---|
| 4,296,114 A | 10/1981 | Appleton et al. | |
| 4,816,064 A | 3/1989 | Konno et al. | |
| 5,705,703 A | 1/1998 | Bernauer et al. | |
| 6,774,235 B2 | 8/2004 | Daeyaert et al. | |
| 10,604,492 B2 | 3/2020 | Verkman et al. | |
| 11,230,535 B2 | 1/2022 | Verkman et al. | |
| 2004/0209880 A1 | 10/2004 | Timmer et al. | |
| 2005/0256000 A1 | 11/2005 | Schaper et al. | |
| 2009/0105240 A1 | 4/2009 | Mustelin et al. | |
| 2009/0291950 A1 | 11/2009 | Govek et al. | |
| 2010/0168154 A1 | 7/2010 | Shishikura et al. | |
| 2013/0040986 A1 | 2/2013 | Binch et al. | |
| 2016/0317493 A1 | 11/2016 | Van Der Plas et al. | |
| 2019/0031622 A1 | 1/2019 | Verkman et al. | |
| 2019/0337929 A1 | 11/2019 | Walters et al. | |
| 2021/0154201 A1 | 5/2021 | Verkman et al. | |
| 2022/0081402 A1 | 3/2022 | Verkman et al. | |

FOREIGN PATENT DOCUMENTS

| | | |
|---|---|---|
| CN | 1295476 A | 5/2001 |
| CN | 102361855 A | 2/2012 |
| CN | 105130948 A | 12/2015 |
| CN | 108699107 A | 10/2018 |
| EA | 004540 B1 | 6/2004 |
| EA | 009728 B1 | 2/2008 |
| EP | 0008864 A1 | 3/1980 |
| EP | 2935277 A0 | 10/2015 |
| EP | 3394083 B1 | 9/2021 |
| EP | 3394040 B1 | 12/2021 |
| JP | 2002509923 A | 4/2002 |
| JP | 2007537172 A | 12/2007 |
| JP | 2018533169 A | 11/2018 |
| JP | 2018538352 A | 12/2018 |
| JP | 2018538354 A | 12/2018 |
| JP | 2019505502 A | 2/2019 |
| JP | 2020531511 A | 11/2020 |
| JP | 6894902 B2 | 6/2021 |
| JP | 6938509 B2 | 9/2021 |
| WO | 94/11355 A1 | 5/1994 |
| WO | 99/50254 A1 | 10/1999 |
| WO | 01/47897 A1 | 7/2001 |
| WO | 03/024926 A2 | 3/2003 |
| WO | 2004/031184 A1 | 4/2004 |

(Continued)

OTHER PUBLICATIONS

Gennaro, Remington's Pharmaceutical sciences, Ophthalmic Preparation—Preparation, Mack Pub., 19th Edition, 1995, pp. 1568-1569.*
Al-Muhammed et al., "In-vivo studies on dexamethasone sodium phosphate liposomes," *J. Microencapsul.* 13(3):293-305, 1996.
Al-Nakkash et al., "Activation of a CFTR-Mediated Chloride Current in a Rabbit Corneal Epithelial Cell Line," *Invest. Ophthalmol. Vis. Sci.* 42(10):2364-2370, 2001.
Allen, *The Art, Science and Technology of Pharmaceutical Compounding*, Fifth Edition, American Pharmacists Association, 1999. (8 pages), Introduction, pp. xxxi-xxxvii.
Alves et al., "Dry Eye Disease Treatment: A Systematic Review of Published Trials and Critical Appraisal of Therapeutic Strategies," *Ocul. Surf.* 11(3):181-192, 2013.

(Continued)

*Primary Examiner* — Gigi G Huang
(74) *Attorney, Agent, or Firm* — Seed IP Law Group LLP

(57) ABSTRACT

The disclosure provides, inter alia, topical pharmaceutical compositions comprising active agents, methods for increasing tear production using the topical pharmaceutical compositions, and methods for treating dry eye disorders using the topical pharmaceutical compositions.

10 Claims, 8 Drawing Sheets

(56) References Cited

FOREIGN PATENT DOCUMENTS

| WO | 2005/009980 | A1 | 2/2005 | | |
|---|---|---|---|---|---|
| WO | 2005/075435 | A1 | 8/2005 | | |
| WO | 2005/103015 | A1 | 11/2005 | | |
| WO | 2005/112630 | A1 | 12/2005 | | |
| WO | 2007/095812 | A1 | 8/2007 | | |
| WO | 2009/091388 | A2 | 7/2009 | | |
| WO | 2009/091388 | A3 | 7/2009 | | |
| WO | 2009/091388 | A4 | 7/2009 | | |
| WO | 2009/109258 | A1 | 9/2009 | | |
| WO | 2010/048564 | A1 | 4/2010 | | |
| WO | 2010/073011 | A2 | 7/2010 | | |
| WO | 2011/124869 | A1 | 10/2011 | | |
| WO | 2012/092471 | A2 | 7/2012 | | |
| WO | 2015/168079 | A1 | 11/2015 | | |
| WO | 2017/112950 | A1 | 6/2017 | | |
| WO | 2017/112951 | A1 | 6/2017 | | |
| WO | WO-2017112950 | A1 | * | 6/2017 | ........... C07D 498/06 |
| WO | 2019/040919 | A1 | 2/2019 | | |

OTHER PUBLICATIONS

Anitha et al., "Gut Microbial Products Regulate Murine Gastrointestinal Motility Via Toll-Like Receptor 4 Signaling," *Gastroemerology* 143(4):1006-1016.e4, 2012.

Ansari et al., "Ocular signs and symptoms and vitamin A status in patients with cystic fibrosis treated with daily vitamin A supplements," *Br. J. Oghthalmol.* 83:688-691, 1999.

Asbell et al., "Ophthalmologist Perceptions Regarding Treatment of Moderate-to-Severe Dry Eye: Results of a Physician Survey," *Eye Contact Lens* 36(1):33-38, 2010.

Berge et al., "Pharmaceutical Salts," *Journal of Pharmaceutical Science* 66(1):1-19, 1977.

Bhattacharya et al., "Tear Production After Bilateral Main Lacrimal Gland Resection In Rabbits," *Invest. Ophthalmol. Vis. Sci.* 56(13):7774-7783, 2015.

Bijvelds et al., "Activation of Intestinal Cl⁻ Secretion by Lubiprostone Requires the Cystic Fibrosis Transmembrane Conductance Regulator," *Gastroemerology* 137(3):976-985, 2009.

Botelho et al., "Tear sodium, potassium, chloride, and calcium at various flow rates: Children with cystic fibrosis and unaffected siblings with and without corneal staining," *The Journal of Pediatrics* 83(4):601-606, 1973.

Busby et al., "Linaclotide, through activation of guanylate cyclase C, acts locally in the gastrointestinal tract to elicit enhanced intestinal secretion and transit," *European Journal of Pharmacology* 649:328-335, 2010.

Candia, "Electrolyte and fluid transport across corneal, conjunctival and lens epithelia," *Experimental Eye Research* 78:527-535, 2004.

Cao et al., "Chloride Channels And Transporters In Human Corneal Epithelium," *Exp. Eye Res.* 90(6):771-779, 2010. (18 pages)

Castro et al., "Linaclotide Inhibits Colonic Nociceptors and Relieves Abdominal Pain Via Guanylate Cyclase-C and Extracellular Cyclic Guanosine 3',5'-Monophosphate," *Gastroemerology* 145(6):1334-1346, 2013.

Chao et al., "Activation of intestinal CFTR Cl⁻ channel by heat-stable enterotoxin and guanylin via cAMP-dependent protein kinase," *EMBO J.* 13(5):1065-1072, 1994.

Chey et al., "Naloxegol for Opioid-Induced Constipation in Patients with Noncancer Pain," *New England Journal of Medicine* 370(25):2387-2396, 2014.

Cholon et al., "Potentiator Ivacaftor Abrogates Pharmacological Correction of ΔF508 CFTR in Cystic Fibrosis," *Sci. Transl. Med.* 6(246):1-31, 2014.

Chonn et al., "Recent advances in liposomal drug-delivery systems," *Curr. Opin. Biotechnol.* 6:698-708, 1995.

Cil et al., "Benzopyrimido-pyrrolo-oxazine-dione CFTR inhibitor (R)-BPO-27 for antisecretory therapy of diarrheas caused by bacterial enterotoxins," *FASEB J.* 31:751-760, 2017.

Cil et al., "CFTR Activator Increases Intestinal Fluid Secretion and Norrnalizes Stool Output in a Mouse Model of Constipation," *Cell Mol. Gastroenterol Hepatol.* 2(3):317-327, 2016.

Cil et al., "Phenylquinoxalinone CFTR activator as potential prosecretory therapy for constipation," *Transl. Res.* 182:14-26, 2017. (23 pages).

Coffman et al., "Constrained Bithiazoles: Small Molecule Correctors of Defective AF508-CFTR Protein Trafficking," *J. Med. Chem.* 57:6729-6738, 2014.

Dartt, "Regulation of mucin and fluid secretion by conjunctival epithelial cells," *Progress in Retinal and Eye Research* 21:555-576, 2002.

De La Fuente et al., "Small-molecule screen identifies inhibitors of a human intestinal calcium-activated chloride channel," *Mol. Pharmacol.* 73:758-768, 2007. (39 pages).

Dekkers et al., "A Functional CFTR assay using primary cystic fibrosis intestinal organoids," *Nature Medicine* 19(7):939-945, 2013. (9 pages).

Dovlatian et al., "Synthesis and Thermic Decomposition of Halogenalkoxy(thio)-symm-Triazines," *Armyanskii Khimicheskii Zhurnal* 41(6):346-351, 1988.

Dudley et al., "Cyanuric Chloride Derivatives. III. Alkoxy-s-triazines," *Journal of the American Chemical Society* 73:2986-2990, 1951.

Eckford et al., "Cystic Fibrosis Transmembrane Conductance Regulator (CFTR) Potentiator VX-770 (Ivacaftor) Opens the Defective Channel Gate of Mutant CFTR in a Phosphorylation-Dependent but ATP-independent Manner," *Journal of Biological Chemistry* 287(44):36639-36649, 2012.

Esteva-Font et al., "Diuresis and reduced urinary osmolality in rats produced by small-molecule UT-A-selective urea transport inhibitors," *FASEB J.* 28(9):3878-3890, 2014.

Extended European Search Report dated July 10, 2019 in corresponding EP Application No. 16880160.3, 9 pages.

Eyles, "Oral Delivery and Fate of Poly(lactic acid) Microsphere-encapsulated Interferon in Rats," *J. Pharm. Pharmacol.* 49:669-674, 1997.

Fei et al., "Lubiprostone Reverses the Inhibitory Action of Morphine on Intestinal Secretion in Guinea Pig and Mouse," *Journal of Pharmacology and Experimental Therapeutics* 334(1):333-340, 2010. (37 pages).

Field et al., "Effect of Cholera Enterotoxin on Ion Transport across Isolated Ileal Mucosa," *The Journal of Clinical Investigation* 51:796-804, 1972.

Field, "Mechanisms of action of cholera and *Escherichia coli* enterotoxins," *Am. J. Clin. Nutr.* 32(1):189-196, 1979. (10 pages).

Flores et al., "Small-molecule CFTR activators increase tear secretion and prevent experimental dry eye disease," *FASEB J.* 30:1789-1797, 2016.

Foulke-Abel et al., "Human Enteroids as a Model of Upper Small Intestinal Ion Transport Physiology and Pathophysiology," *Gastroenterology* 150:638-649.e8, 2016.

Fox et al., "Discovery of 6-Phenylpyrimido[4,5-b][1,4]oxazines as Potent and Selective Acyl CoA:Diacylglycerol Acyltransferase 1 (DGAT1) Inhibitors with in vivo Efficacy in Rodents," *J. Med. Chem.* 57:3464-3483, 2014.

Gabriel et al., "Cystic Fibrosis Heterozygote Resistance To Cholera Toxin In The Cystic Fibrosis Mouse Model," *Science* 266:107-109, 1994. (4 pages).

Galietta et al., "Cell-based assay for high-throughput quantitative screening of CFTR chloride transport agonists," *Am. J. Physiol. Cell Physiol.* 281:C1734-1742, 2001.

Galietta et al., "Green fluorescent protein-based halide indicators with improved chloride and iodide affinities," *FEBS Lett.* 499:220-224, 2001.

Galietta et al., "Novel CFTR Chlonde Channel Activators Identified by Screening of Combinatorial Libraries Based on Flavone and Benzoquinolizinium Lead Compounds," *J. Biol. Chem.* 276(23):19723-19728, 2001. (7 pages).

Gao et al., "Controlled Release of a Contraceptive Steroid from Biodegradable and Injectable Gel Formulations: In Vitro Evaluation," *Pharm. Res.* 12(6):857-863, 1995.

(56) References Cited

OTHER PUBLICATIONS

Gilbard et al., "Morphologic Effect of Hyperosmolarity on Rabbit Corneal Epithelium," *Ophthalmology* 91(10):1205-1212, 1984.

Gras et al., "Bronchial epithelium as a target for innovative treatments in asthma," *Pharmacology & Therapeutics* 140(3):290-305, 2013.

Haggie et al., "Inhibitors of pendrin anion exchange identified in a small molecule screen increase airway surface liquid volume in cystic fibrosis," *FASEB J.* 30:2187-2197, 2016.

Hecht et al., "Differential regulation of $Na^+/H^+$ exchange isoform activities by enteropathogenic *E. coli* in human intestinal epithelial cells," *American Journal of Physiology—Gastrointestinal and Liver Physiology* 287:G370-G378, 2004.

Hong et al., "Mechanism And Syriergism In Epithelial Fluid And Electrolyte Secretion," *Pflugers Arch.* 466(8):1487-1499, 2014. (26 pages).

Hosoda et al., "Targeted and Natural (Piebald-lethal) Mutations of Endothelin-B Receptor Gene Produce Megacolon Associated with Spotted Coat Color in Mice," *Cell* 79:1267-1276, 1994.

Hwang et al., "Identification of a series of 1,3,4-trisubstituted pyrazoles as novel hepatitis C virus entry inhibitors," *Bioorganic & Medicinal Chemistry Letters* 23:6467-6473, 2013.

International Search Report, dated Mar. 30, 2017, for International Application No. PCT/US2016/068569, 3 pages.

International Search Report and Written Opinion, dated Oct. 30, 2018, for International Application No. PCT/US2018/048025, 7 pages.

Jean-Claude et al., "Synthesis of Bi- and Tri-cyclic Tetrazepinones," *J. Chem. Soc., Perkin Trans.* 10:2525-2529, 1991. (7 pages).

Jowa et al., "Should Atrazine and Related Chlorotriazines Be Considered Carcinogenic for Human Health Risk Assessment?," *Journal of Environmental Science and Health, Part C*, 29:91-144, 2011. (55 pages).

Kim et al., "Construction of 1,2,5-Tricarbonyl Compounds using Methyl Cyanoacetate as a Glyoxylate Anion Synthon Combined with Copper(I) Iodide-Catalyzed Aerobic Oxidation," *Adv. Synth. Catal.* 353:3335-3339, 2011.

Koh et al., "Long-term results of treatment with diquafosol ophthalmic solution for aqueous-deficient dry eye," *J. Ophthalmol.* 57:440-446, 2013.

Kompella et al., "Active chloride transport in the pigmented rabbit conjunctiva," *Curr. Eye Res.* 12:1041-1048, 1993.

Lawrence et al., "Structure-Activity Studies of Substituted Quinoxalinones as Multiple-Drug-Resistance Antagonists," *Journal of Medicinal Chemistry* 44:594-601, 2001.

Lee et al., "Nanomolar-Potency Aminophenyl-1,3,5-Triazine Activators Of The Cystic Fibrosis Transmembrane Conductance Regulator (CFTR) Chloride Channel For Pro-Secretory Therapy Of Dry Eye Diseases," *J. Med. Chem.* 60(3):1210-1218, 2017. (24 pages).

Lembo et al., "Two Randomized Trials of Linaclotide for Chronic Constipation," *New England Journal of Medicine* 365(6):527-536, 2011.

Lemp et al., "Tear Osmolarity in the Diagnosis and Management of Dry Eye Disease," *Am. J. Ophthalmol.* 151(5):792-798, 2011.

Lemp et al., "The definition and classification of dry eye disease: Report of the Definition and Classification Subcommittee of the International Dry Eye WorkShop," DEWS, *Ocul. Surf.* 5:75- 204, 2007. (128 pages).

Lencer et al., "Opening CFTR in the Intestine: Flushing on Demand," *Cellular and Molecular Gastroenterology and Hepatology* 2:256, 2016.

Levin et al., "CFTR-Regulated Chloride Transport at the Ocular Surface in Living Mice Measured by Potential Differences," *Invest. Ophthalmol. Vis. Sci.* 46(4):1428-1434, 2005.

Levin et al., "Potential Difference Measurements of Ocular Surface Na+ Absorption Analyzed Using an Electrokinetic Model," *Invest. Ophthalmol. Vis. Sci.* 47(1):306-316, 2006.

Li et al., "Dependence of cAMP Mediated Increases In Cl- And HCO3-Permeability On CFTR In Bovine Corneal Endothelial Cells," *Exp. Eye Res.* 86(4):684-690, 2008. (13 pages).

Lipinski et al., "Experimental and computational approaches to estimate solubility and permeability in drug discovery and development settings," *Advanced Drug Delivery Reviews* 23(1997):3-25, 1997.

Liu et al., "A Link between Tear Instability and Hyperosmolarity in Dry Eye," *Invest. Ophthalmol. Vis. Sci.* 50(8):3671-3679, 2009.

Lu et al., "CFTR-mediated Cl(-) Transport in the Acinar and Duct Cells of Rabbit Lacrimal Gland," *Curr. Eye Res.* 37(8):671-677, 2012. (13 pages).

Luo et al., "Hyperosmolar Saline Is A Proinflammatory Stress on the Mouse Ocular Surface," *Eye & Contact Lens* 31(5):186-193, 2005.

Ma et al., "High-affinity Activators of Cystic Fribrosis Transmembrane Conductance Regulator (CFTR) Chloride Conductance Identified by High-throughput Screening," *J. Biol. Chem.* 277(40):37235-37241, 2002.

Menees et al., "Agents that act luminally to treat diarrhoea and constipation," *Nature Reviews Gastroenterology and Hepatology* 9(11):661-674, 2012.

Milner et al., "Dysfunctional Tear Syndrome: Dry Eye Disease And Associated Tear Film Disorders—New Strategies For Diagnosis And Treatment," *Curr Opin Ophthalmol.* 28(1), 2017. (48 pages).

Moon et al., "A Novel Microtubule Destabilizing Entity from Orthogonal Synthesis of Triazine Library and Zebrafish Emryo Screening," *J. Am. Chem. Soc.* 124:11608-11609, 2002.

Moon et al., "Drug-induced secretory diarrhea: A role for CFTR," *Pharmacol Res.* 102:107-112, 2015. (12 pages).

Morkeberg et al. "Ocular findings in cystic fibrosis patients receiving vitamin A supplementation," *Graefes Arch. Clin. Exp. Ophthalmol.* 233:709-713, 1995. (7 pages).

Mrugacz et al., "IL-8 and IFN-gamma in Tear Fluid of Patients with Cystic Fibrosis," *Journal of Interferon & Cytokine Research* 26:71-75, 2006.

Mugie et al., "Constipation in childhood," *Nature Reviews Gastroenterology and Hepatology* 8(9):502-511, 2011.

Murakami et al., "Disquafosol Elicits Increases in Net Cl- Transport Through $P2Y_2$ Receptor Stimulation in Rabbit Conjunctiva," *Ophthalmic Res.* 36:89-93, 2004.

Namkung et al., "TMEMI6A Inhibitors Reveal TMEMI6A as a Minor Component of Calcium-Activated Chloride Channel Conductance in Airway and Intestinal Epithelial Cells," *J. Biol. Chem.* 286(3):2365-2374, 2011.

Nandoskar et al., "Changes of Chloride Channels in the Lacrimal Glands of a Rabbit Model of Sjögren syndrome," *Cornea* 31(3):273-279, 2012.

Nichols et al., "Diquafosol tetrasodium: a novel dry eye therapy," *Expert. Opin. Investig.. Drugs* 13(1):47-54, 2004.

Ong et al., "New Therapeutic Approaches to Modulate and Correct CFTR," *Pediatr. Clin. North. Am.* 63(4):751-764, 2016.

Ostro, "Use of liposomes as injectable-drug delivery systems," *Am. J. Hosp. Pharm.* 46(8):1576-1587, 1989. (13 pages).

Phuan et al., "Cyanoquinolines with Independent Corrector and Potentiator Activities Restore ΔPhe508-Cystic Fibrosis Transmembrane Conductance Regulator Chloride Channel Function in Cystic Fibrosis," *Mol. Pharmacol.* 80(4):683-693, 2011.

Pinto Sanchez et al., "Epidemiology and burden of chronic constipation," *Canadian Journal of Gastroenterology* 25(Suppl. B):11B-15B, 2011.

Plebanek et al., "Straightforward synthesis of 2,4,6-trisubstituted 1,3,5-triazine compounds targeting cysteine cathepsins K and S," Manuscript—*Eur. J. Med. Chem.* 121:12-20, 2016. (20 pages).

Qin et al., "Design and Synthesis of Potent and Multifunctional Aldose Reductase Inhibitors Based on Quinoxalinones," *Journal of Medicinal Chemistry* 58:1254-1267, 2015.

Raghunadh et al., "An Efficient and Practical Synthesis of Aryl and Hetaryl α-Keto Esters," *Synthesis* 44:283-289, 2012.

Ramsey et al., "A CFTR Potentiator in Patients with Cystic Fibrosis and the G551D Mutation," *N. Engl. J. Med.* 365(18):1663-1672, 2011.

Rao et al., "Mode of Action of Heat-Stable *Escherichia coli* Enterotoxin: Tissue and Subcellular Specificities and Role of Cyclic GMP," *Biochimica et Biophysica Acta (BBA)—General Subjects* 632(1):35-46, 1980.

(56) References Cited

OTHER PUBLICATIONS

Rao, "Recent developments of collagen-based materials for medical applications and drug delivery systems," *J. Biomater Sci. Polym.* 7(7):623-645, 1995.

Ratcliff et al., "Production of a severe cystic fibrosis mutation in mice by gene targeting," *Nature Genetics* 4:35-41, 1993.

Rowe et al, "Nasal Potential Difference Measurements To Assess CFTR Ion Channel Activity," *Methods Mol. Biol.* 741:69-86, 2011. (16 pages).

Saint-Criq et al., "Role of CFTR in epithelial physiology," *Cell Mol. Life Sci.* 74:93-115, 2017.

Schaumberg et al., "Prevalence of Dry Eye Disease Among US Men: Estimates from the Physicians' Health Studies," *Arch. Ophthalmol.* 127(6):763-768, 2009.

Schaumberg et al., "Prevalence of Dry Eye Syndrome Among US Women," *Am. J. Ophthalmol.* 136(2):318-326, 2003.

Schmidt et al., "Cystic fibrosis transmembrane conductance regulator modulators in cystic fibrosis: current perspectives," *Clin. Pharmacol* 8:127-140, 2016.

Shaw et al., "One-Pot Two-Step Synthesis of Quinoxalinones and Diazepinones Via a Tandem Oxidative Amidation-Deprotection-Cyclization Seguence," *Synthesis* 45:459-462, 2013.

Sheppard et al., "Lifitegrast Ophthalmic Solution 5.0% for Treatment of Dry Eye Disease: Results of the OPUS-1 Phase 3 Study," *Ophthalmology* 121(2):475-483, 2014.

Shiue et al., "Characterization of cyclic AMP-regulated chloride conductance in the pigmented rabbit conjunctival epithelial cells," *Can. J. Physiol. Pharmacol.* 80:533-540, 2002.

Snyder et al., "Potent, Metabolically Stable Benzopyrimido-Pyrrolo- Oxazine-Dione (BPO) CFTR Inhibitors for Polycystic Kidney Disease," *J. Med. Chem.* 54(15):5468-5477, 2011. (20 pages).

Solomon et al., "Breakthrough Therapies: Cystic Fibrosis (CF) Potentiators and Correctors," *Pediatr. Pulmonol.* 50:S3-S13, 2015.

Solomon et al., "Therapeutic Approaches to Acquired Cystic Fibrosis Transmembrane Conductance Regulator Dysfunction in Chronic Bronchitis," *Ann. Am. Thorac. Soc. Suppl* 13(2):S169-S176, 2016.

Srivastava et al., "Progressive Familial Intrahepatic Cholestasis," *Journal of Clinical and Experimental Hepatology* 4(1):25-36, 2014.

Stevenson et al., "Extraorbital Lacrimal Gland Excision: A Reproducible Model of Severe Aqueous Tear-Deficient Dry Eye Disease," *Cornea* 33(2):1336-1341, 2014.

Stewart et al., "Effect of Experimental Dry Eye on Tear Sodium Concentration in the Mouse," *Eye & Contact Lens* 31(4):175-178, 2005.

Subramanya et al., "Differential regulation of cholera toxin-inhibited Na-H exchange isoforms by butyrate in rat ileum," *American Journal of Physiology—Gastrointestinal and Liver Physiology* 293:G857-G863, 2007.

Sullivan et al., "Does Androgen Insufficiency Cause Lacrimal Gland Inflammation and Aqueous Tear Deficiency?," *Invest. Ophthalmol. Vis. Sci.* 40(6):1261-1265, 1999.

Takamura et al., "A randomised, double-masked comparison study of diquafosol versus sodium hyaluronate ophthalmic solutions in dry eye patients," *Br. J. Ophthalmol.* 96:1310-1315, 2012.

Tauber et al., "Double-Masked, Placebo-Controlled Safety And Efficacy Trial Of Diquafosol Tetrasodium (INS365) Ophthalmic Solution for the Treatment Of Dry Eye," *Cornea* 23(8):784-792, 2004.

Thelin et al., "Effect of Topically Applied Epithelial Sodium Channel Inhibitors on Tear Production in Normal Mice and in Mice with Induced Aqueous Tear Deficiency," *J. Ocul. Pharmacol. Ther.* 28(4):433-438, 2012.

Thiagarajah et al., "Secretory diarrhoea: mechanisms and emerging therapies," *Nature Reviews Gastroenterology and Hepatology* 12(8):446-457, 2015. (24 pages).

Turner et al., "Cyclic AMP-dependent Stimulation of Basolateral $K^+$ Conductance in the Rabbit Conjunctival Epithelium," *Exp. Eye Res.* 70:295-305, 2000.

Turner et al., "Presence of CFTR in the conjunctival epithelium," *Curr. Eye Res.* 24(3):182-187, 2002.

Van Goor et al., "Pharmacological Rescue of Mutant CFTR Function for the Treatment of Cystic Fibrosis," *Top. Med. Chem.* 3:91-120, 2008.

Veber et al., "Molecular Properties That Influence the Oral Bioavailability of Drug Candidates," *Journal of Medicinal Chemistry* 45:2615-2623, 2002.

Verkman et al., "Chloride channels as drug targets," *Nat. Rev. Drug Discov.* 8(2):153-171, 2009. (39 pages).

Vijmasi et al., "Topical administration of interleukin-1 receptor antagonist as a therapy for aqueous-deficient dry eye in autoimmune disease," *Mol. Vis.* 19:1957-1965, 2013.

Villareal et al., "Effect of Topical Ophthalmic Epinastine and Olopatadine on Tear Volume in Mice," *Eye & Contact Lens* 32(6):272-276, 2006.

Watsky et al., "Comparison of conjunctival and corneal surface area in rabbit and human," *Curr. Eye Res.* 7(5):483-486, 1988.

Webster et al., "Embryogenesis of the enteric ganglia in normal mice and in mice that develop congenital aganglionic megacolon," *J. Embryol. exp. Morph.* 30(3):573-585, 1973.

Whittaker et al., "Evaluation Of Lacrimation Characteristics In Clinically Normal New Zealand White Rabbits By Using The Schirmer Tear Test I," *J. Am. Assoc. Lab. Anim. Sci.* 54(6):783-787, 2015.

Wolosin et al., "$Cl^-$ secretagogues increase basolateral $K^+$ conductance of frog corneal epithelium," *Am. J. Physiol.* 253(4):C555-C560, 1987. (8 pages).

Yao et al., "Triazolothienopyrimidine Inhibitors of Urea Transporter UT-B Reduce Urine Concentration," *J. Am. Soc. Nephrol.* 23:1210-1220, 2012.

Yu et al., "Regional differences in rat conjunctival ion transport activities," *Am. J. Physiol. Cell Physiol.* 303:C767-C780, 2012.

Yu et al., "The Economic Burden Of Dry Eye Disease in the United States: A Decision Tree Analysis," *Cornea* 30(4):379-387, 2011.

Zaidi et al., "Cystic Fibrosis Transmembrane Conductance Regulator-Mediated Corneal Epithelial Cell Ingestion Of Pseudomonas Aeruginosa Is A Key Component In The Pathogenesis Of Experimental Mutine Keratitis," *Infection and Immunity* 67(3):1481-1492, 1999.

Zarate et al., "Chronic constipation: Lessons from animal studies," *Best Practice & Research Clinical Gastroemerology* 25(1):59-71, 2011.

Baindur et al., "2-Hydroxy-4,6-diamino-[1,3,5]triazines: A Novel Class of VEGF-R2 (KDR) Tyrosine Kinase Inhibitors," *J. Med. Chem.* 48(6):1717-1720: 2005.

Li et al., "Revealing Interaction Mode Between HIV-1 Reverse Transcriptase and Diaryltriazine Analog Inhibitor," *Chem. Biol. Drug Des.* 72:350-359, 2008.

Ludovici et al., "Evolution of Anti-HIV Drug Candidates Part 2: Diaryltriazine (DATA) Analogues," *Bioorganic & Medicinal Chemistry Letters* 11:2229-2234, 2001.

Moran et al., "Binding site of activators of the cystic fibrosis transmembrane conductance regulator in the nucleotide binding domains," *CMLS Cellular and Molecular Life Sciences* 62:446-460, 2005.

Office Action, dated Mar. 10, 2020, for Russian Patent Application No. 2018126958, 21 pages. (w/ English Translation).

Pubchem, "N-Methyl-N'-phenyl-6-(2,2,2-trifluoroethoxy)-1,3,5-triazine-2,4-diamine," PubChem CID 2266465, 2005. (11 pages).

Shah et al., "Synthesis and Diuretic Activity of 2-Amino-4-arylamino-6-mercapto-s-triazines and Related Derivatives," 1167-1171, 1968.

"Public Health Strategic Framework for COPD Prevention," Electronic Resource: [https://www.cdc.gov/copd/pdfs/Framework_for_COPD_Prevention.pdf], Retrieved on Sep. 18, 2018. (20 pages).

Ahmad et al., "A High Throughput Assay for Discovery of Bacterial β-Glucuronidase Inhibitors", *Current Chemical Genomics* 5:13-20, 2011. (8 pages).

CAS RN 319490-42-1, 2(1H)-Quinoxalinone, 3-(2-amino-5-nitrophenyl)-1-(phenylmethyl)-, STN entry date Feb. 2, 2001. (2 pages).

(56) References Cited

OTHER PUBLICATIONS

Dorjsuren et al., "Diverse Small Molecule Inhibitors of Human Apurinic/Apyrimidinic Endonuclease APE1 Identified from a Screen of a Large Public Collection," *PloS ONE*, 7(10):e47974, Oct. 23, 2012. (12 pages).
Extended European Search Report, dated May 11, 2022, for European Application No. 21207338.1. (9 pages).
Extended European Search Report, dated Aug. 19, 2022, for European Application No. 22159301.5. (9 pages).
Felix et al. "Pro-Secretory Activity and Pharmacology in Rabbits of an Aminophenyl-1,3,5-Triazine CFTR Activator for Dry Eye Disorders," *Physiology and Pharmacology, Invest Ophthalmol Vis Sci.* 58(11):4506-4513, Sep. 2017. (8 pages).
Horig et al., "From bench to clinic and back: Perspective on the 1$^{st}$ IQPC Translational Research conference," *Journal of Translational Medicine* 2:44, Dec. 20, 2004. (8 pages).
Mukhina et al., "Amino Azaxylylenes Photogenerated from o-Amido Imines: Photoassisted Access to Complex Spiro-Poly-Heterocycles", *Angewandte Chemie International Edition 54*:11516-11520, 2015. (5 pages).
Ruiz-Ederra et al., "In Situ Fluorescence Measurement of Tear Film [Na$^+$], [K$^+$], [Cl$^-$], and pH in Mice Shows Marked Hypertonicity in Aquaporin-5 Deficiency," *Investigative Ophthalmology & Visual Science 50*(5): 2132-2138, May 2009. (7 pages).
Schafer et al., "Failure is an option: learning from unsuccessful proof-of-concept trials," *Drug Discovery Today* 13(21/22):913-916, Nov. 2008. (4 pages).
Son et al., "High-Potency Phenylquinoxalinone Cystic Fibrosis Transmembrane Conductance Regulator (CFTR) Activators," *J. Med. Chem.* 60(6):2401-2410, Mar. 23, 2017. (HHS Public Access, Author Manuscript, available in PMC Mar. 23, 2018) (31 pages).
STN International, CAS Registry No. 301211-36-9, File Registry [online], 1,3,5-Triazine-2,4-diamine, N2,N2-dimethyl-N4-(4-nitrophenyl)-6-(2,2,2-trifluoroethoxy), Nov. 3, 2000. (1 page).
STN International, CAS Registry No. 731836-49-0, File Registry [online], 1,3,5-Triazine-2,4-diamine, N2,N2-diethyl-N4-(4-methylphenyl)-6-[2,2,2-trifluoro-1-(trifluoromethyl)ethoxy], Aug. 24, 2004. (1 page).
STN International, CAS Registry No. 732247-01-7, File Registry [online], 1,3,5-Triazine-2,4-diamine, N4-(4-methoxyphenyl)-N2,N2-dipropyl-6-[2,2,2-trifluoro-1-(trifluoromethyl)ethoxy], Aug. 25, 2004. (1 page).
STN International, CAS Registry No. 732250-34-9, File Registry [online], 1,3,5-Triazine-2,4-diamine, N4-(4-methylphenyl)-N2,N2-dipropyl-6-[2,2,2-trifluoro-1-(trifluoromethyl)ethoxy], Aug. 25, 2004. (1 page).
STN International, CAS Registry No. 733797-64-3, File Registry [online], 1,3,5-Triazine-2,4-diamine, N2,N2-diethyl-N4-(4-methoxyphenyl)-6-[2,2,2-trifluoro-1-(trifluoromethyl)ethoxy], Aug. 27, 2004. (1 page).
STN International, CAS Registry No. 736938-07-1, File Registry [online], 1,3,5-Triazine-2,4-diamine, N2,N2-diethyl-N4-(2-methoxyphenyl)-6-[2,2,2-trifluoro-1-(trifluoromethyl)ethoxy], Sep. 1, 2004. (1 page).
STN International, CAS Registry No. 736970-45-9, File Registry [online], 1,3,5-Triazine-2,4-diamine, N2,N2-dimethyl-N4-phenyl-6-[2,2,2-trifluoro-1-(trifluoromethyl)ethoxy], Sep. 1, 2004. (1 page).
STN International, CAS Registry No. 890717-80-3, File Registry [online], 1,3,5-Triazine-2,4-diamine, N2,N2-dimethyl-N4-1-naphthalenyl-6-[2,2,2-trifluoro-1-(trifluoromethyl)ethoxy], Jul. 6, 2006. (1 page).
STN International, Search Report, Feb. 25, 2021. (39 pages).

\* cited by examiner

US 11,839,616 B2

OCULAR PHARMACEUTICAL COMPOSITIONS

CROSS-REFERENCE TO RELATED APPLICATIONS

This application claims priority to U.S. Provisional Application No. 62/549,872, filed Aug. 24, 2017.

STATEMENT AS TO RIGHTS TO INVENTIONS MADE UNDER FEDERALLY SPONSORED RESEARCH AND DEVELOPMENT

This invention was made with Government support under Grant Numbers EY13574, DK72517, EB00415, DK35124 and DK101373; and UCSF-CTSI Grant UL1 TR000004, awarded by the National Institutes of Health. The Government has certain rights in the invention.

BACKGROUND

Dry eye disorders constitute a significant health care burden, particularly in an aging population. Current treatment options include artificial tears, punctal plugs, and the topical anti-inflammatory drugs cyclosporine and lifitegrast. References 1-3. There is compelling rationale for development of pro-secretory therapy in dry eye, as increasing the volume of tear fluid bathing the ocular surface is predicted to reduce tear fluid hyperosmolality, which drives the downstream inflammatory response and consequent symptoms. Described herein, inter alia, are solutions to these and other problems in the art.

SUMMARY

The disclosure provides methods of increasing tear production in an eye of a patient in need thereof by topically administering to the eye of the patient a pharmaceutical composition comprising about 5 micrograms or more of an active agent to increase tear production; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides methods of treating a dry eye disease in a patient in need thereof by topically administering to an eye of the patient a pharmaceutical composition comprising about 5 micrograms or more of an active agent to treat the dry eye disease; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides methods of increasing tear production in an eye of a patient in need thereof by topically administering to the eye of the patient a pharmaceutical composition comprising about 2 nanomoles or more of an active agent to increase tear production; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides methods of treating a dry eye disease in a patient in need thereof, the method comprising topically administering to an eye of the patient a pharmaceutical composition comprising about 2 nanomoles or more of an active agent to treat the dry eye disease; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides methods of increasing tear production in an eye of a patient in need thereof by topically administering to the eye of the patient a pharmaceutical composition comprising a therapeutically effective amount of an active agent to increase tear production; wherein the therapeutically effective amount provides a concentration of the an active agent in an amount of about 500 nM or more in the tear fluid of the eye about 1 hour to about 12 hours after administration; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides methods of treating a dry eye disease in a patient in need thereof by topically administering to an eye of the patient a pharmaceutical composition comprising a therapeutically effective amount of an active agent to treat the dry eye disease; wherein the therapeutically effective amount provides a concentration of the active agent in an amount of (i) about 500 nM or more in the tear fluid of the eye about 30 minutes to about 3 hours after administration, or (ii) about 10 nM or more in the tear fluid of the eye about 4 hours to about to about 12 hours after administration; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides methods of increasing tear production in an eye of a patient in need thereof by topically administering once per day or twice per day to the eye of the patient a pharmaceutical composition comprising an active agent to increase tear production; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides methods of treating a dry eye disease in a patient in need thereof by topically administering once per day or twice per day to an eye of the patient a pharmaceutical composition comprising an active agent to treat the dry eye disease; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides topical pharmaceutical compositions comprising about 5 micrograms or more of an active agent and a pharmaceutically acceptable carrier; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides topical pharmaceutical compositions comprising an active agent and a pharmaceutically acceptable carrier; wherein the composition comprises the active agent at a concentration from about 1 nanomole to about 25 nmoles per 0.5 mL; and wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides eye droppers for delivering a drop of a topical pharmaceutical composition to the eye of a patient; wherein the eye dropper comprises any of the topical pharmaceutical compositions described herein.

The disclosure provides kits comprising the eye droppers described herein.

The disclosure provides kits comprising an eye dropper, a container which comprises any of the topical pharmaceutical compositions described herein, and instructions for use.

The disclosure provides methods of identifying a patient for treatment with a modulator of ocular surface membrane transport or a modulator of intracellular signaling by (i) measuring the change in the open-circuit transepithelial potential difference, in response to contact with different solutions, at an ocular surface of the patient; (ii) comparing the change in the open-circuit transepithelial potential difference, in response to contact with different solutions, to a control; and (iii) identifying that the patient should be treated with the modulator of ocular surface membrane transport or a modulator of intracellular signaling if the change in the open-circuit transepithelial potential difference is lower than that of the control.

These and other embodiments of the disclosure are described in more detail herein.

BRIEF DESCRIPTION OF THE DRAWINGS

With reference to the figures, $CFTR_{act}$-K267 is also referred to in the disclosure as Compound A.

FIG. 2A is a representative ocular surface PD recording in response to sequential solution exchanges. FIG. 2B is a summary of PD changes (Δ PD) in response to indicated maneuvers (mean±S.E.M., n=16 eyes). FIG. 2C is a representative short-circuit current (Isc) measurement in freshly isolated rabbit forniceal and palpebral conjunctiva in response to compound additions. FIG. 2D is a summary of changes in Isc (Δ Isc) in response to compound additions (mean±S.E.M; n=3).

FIGS. 3A-C show that $CFTR_{act}$-K267 increases tear fluid at the rabbit ocular surface as measured by Schirmer's test. FIG. 3A shows the tear volume (mm, by Schirmer's test) measured just before and at the indicated times after single-dose topical application of 3 nmol of $CFTR_{act}$-K267 or formulation (containing 0.3% CMC) control (mean±S.E.M., 8 eyes per condition). FIG. 3B shows the dose-dependence with study done as in FIG. 3A, comparing 0.75, 1.5 and 6.0 nmol $CFTR_{act}$-K267 (4 eyes per condition). FIG. 3C shows the effect of formulation viscosity, with study done as in FIG. 3A, for formulation containing 0.665% CMC instead of 0.3% CMC (4 eyes per condition). * P<0.05, ** P<0.01, ANOVA, comparing $CFTR_{act}$-K267 vs. vehicle-treated.

FIG. 4A is a standard LC/MS curve of aqueous solutions containing specified concentrations of Compound A. FIG. 4B shows the recovered $CFTR_{act}$-K267 (in picomoles, closed circles, left ordinate) and deduced concentration (in nM, open circles, right ordinate) in tear fluid. Each point is the average of measurements done on 2 eyes for each time point.

FIG. 6A shows representative photographs taken before and at day 28. FIG. 6B shows lissamine green staining scores (mean±S.E.M., 8 eyes). FIG. 6C shows H&E staining of cornea and conjunctiva at day 28. Representative of sections done on 2 eyes per group. S, stroma; CD, corneal endothelium. Scale bars: 100 μm (cornea), 25 μm (conjunctiva).

FIG. 7A is a representative LC/MS elution curves shown for $CFTR_{act}$-K267 in indicated tissues. FIG. 7B shows $CFTR_{act}$-K267 levels in ocular and extraocular tissues (mean±S.E.M., 8 rabbits). LC/MS detection limit shown as vertical dashed line.

DETAILED DESCRIPTION

Figure 1A:
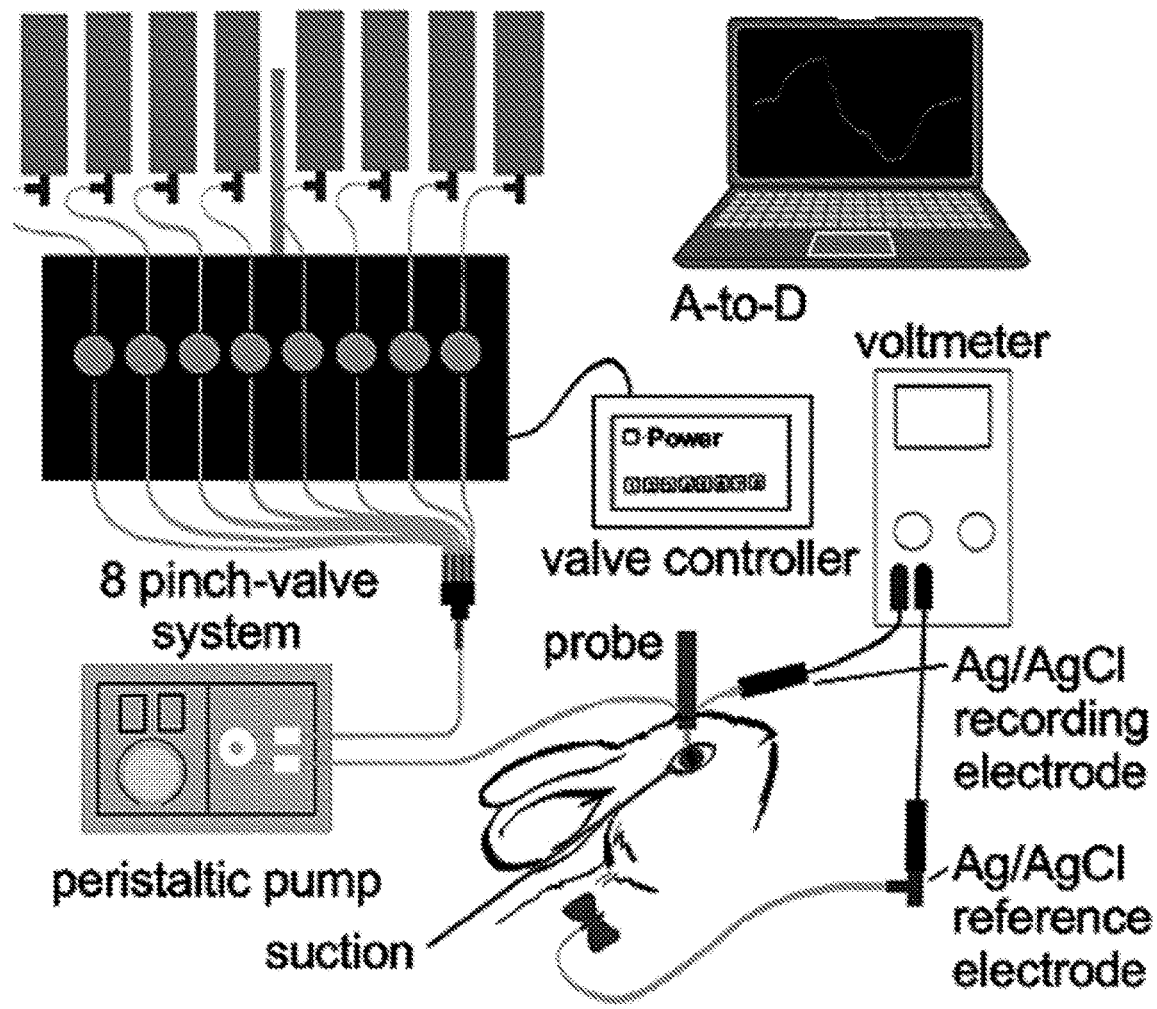
FIGS. 1A-B provide a schematic (FIG. 1A) and photograph (FIG. 1B) of an ocular surface potential difference (PD) recording method. The perfusion catheter coupled to the measuring electrode was oriented perpendicular to the ocular surface near the medial canthus. The eyelids created a natural reservoir for corneal and conjunctival exposure, with vacuum aspiration maintaining a stable perfusate volume.
Figure 1B:
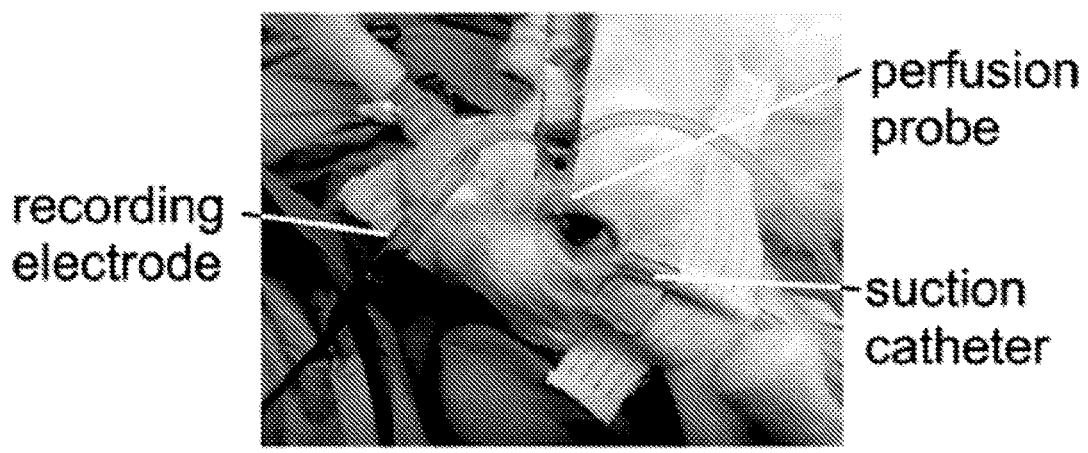

"Active agent" or "active agents" refer to a compound of Formula (I), a compound of Formula (II), a compound of Formula (III), a compound of Formula (IV), Compound A, Compound B, Compound C, Compound D, Compound E, or a pharmaceutically acceptable salt of any of the foregoing. In embodiments, "active agent" is a compound of Formula (I) or a pharmaceutically acceptable salt thereof. In embodiments, "active agent" is a compound of Formula (II) or a pharmaceutically acceptable salt thereof. In embodiments, "active agent" is a compound of Formula (III) or a pharmaceutically acceptable salt thereof. In embodiments, "active agent" is a compound of Formula (IV) or a pharmaceutically acceptable salt thereof. In embodiments, "active agent" is Compound A or a pharmaceutically acceptable salt thereof. In embodiments, "active agent" is Compound B or a pharmaceutically acceptable salt thereof. In embodiments, "active agent" is Compound C or a pharmaceutically acceptable salt thereof. In embodiments, "active agent" is Compound D or a pharmaceutically acceptable salt thereof. In embodiments, "active agent" is Compound E or a pharmaceutically acceptable salt thereof.

The terms "micrograms" or "μg" when referencing the weight of an active agent refers to micrograms of the free base form of the active agent regardless of whether the active agent is present in the form of the free base or the pharmaceutically acceptable salt. For example, 5 micrograms of a pharmaceutically acceptable salt of Compound A means that there is 5 micrograms of the free base form of Compound A.

The terms "nanomoles" or "nM" or "nmoles" when referencing the unit of measurement of an active agent refers to nanomoles of the free base form of the active agent regardless of whether the active agent is present in the form of the free base or the pharmaceutically acceptable salt. For example, 5 nanomoles of a pharmaceutically acceptable salt of Compound A means that there is 5 nanomoles of the free base form of Compound A.

"Tear fluid" or "tears" or "tear" refer to the watery fluid secreted by the lacrimal glands between the surface of the eye and the eyelid that serve to moisten, lubricate, and protect the eye.

"Increasing tear production" refers to increasing the tear production in a patient relative to a control. The control can be the same patient prior to treatment, a statistical group of patients who have not been treated, or a different patient who has not been treated. In embodiments, increasing tear production refers to doubling the tear production of the patient when compared to the tear production of the patient prior to treatment (or when compared to another control) with the active agents described herein. In embodiments, increasing tear production refers to tripling or quadrupling tear production when compared to the tear production of the patient prior to treatment (or when compared to another control) with the active agents described herein. In embodiments, increasing tear production refers to increasing the tear production of a patient to within a normal range of tear production for the patient relative to a control or to applicable standards known in the art. Methods of measuring tear production are known in the art, and include, for example, Schirmer's tear tests I (unanesthetized) and II (anesthetized, measured after instillation of topical 0.5% proparacaine). If the patient is a human, the normal result for a Schirmer's tear test I is generally more than 10 mm of moisture on the filter paper after about 5 minutes. Thus, in embodiments, increasing tear production refers to an increase in tear production to at least 10 mm of moisture on a filter paper after about 5 minutes following Schirmer's tear test I. In embodiments, increasing tear production refers to an increase in tear production from about 10 mm to about 15 mm of moisture on a filter paper after about 5 minutes following Schirmer's tear test I. If the patient is a human, the normal result for a Schirmer's tear test II is generally more than 5 mm of moisture on the filter paper after about 5 minutes. Thus, in embodiments, increasing tear production refers to an increase in tear production to at least 5 mm of moisture on a filter paper after about 5 minutes following Schirmer's tear test II. In embodiments, increasing tear production refers to an increase in tear production from about 5 mm to about 10 mm of moisture on a filter paper after about 5 minutes following Schirmer's tear test II. In embodiments, increasing tear production refers to increasing the results of the Schirmer's tear tests relative to the results prior to administration of the active agents and compositions described herein.

"Dry eye disease" is a disease in which a patient experiences dryness in one or both eyes. Dry eye disease is marked by an insufficient quality or quantity of tear production. Exemplary symptoms of dry eye disease include irritation, burning, stinging, discharge, foreign body sensation, tearing, blurred vision, or a combination of two or more symptoms. Dry eye disease may alternatively be referred to as dry eye syndrome, keratoconjunctivitis sicca, dysfunctional tear syndrome, or lacrimal keratoconjunctivitis. Dry eye disease may be caused by medications, advanced age, rosacea, blepharitis, autoimmune disorders (e.g., Sjogren's syndrome), diabetes, thyroid disorders, Vitamin A deficiency, environmental conditions (e.g., dry or windy environments), seasonal allergies, sun exposure, or laser eye surgery. In embodiments, dry eye disease may be diagnosed by Schirmer's tear tests and/or ocular surface staining patterns of Lissamine green, Rose Bengal, and/or fluorescein dyes.

"Patient" and "patient in need thereof" refer to a living organism suffering from or prone to a disease that can be treated by administration of the active agents described herein. Non-limiting examples include humans, other mammals, bovines, rats, mice, dogs, monkeys, goat, sheep, cows, and other non-mammalian animals. In embodiments, the patient is human. In embodiments, the patient is a dog. In embodiments, the patient is a cat.

The terms "treating", or "treatment" refer to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; or improving a patient's physical well-being. The treatment of symptoms can be based on objective or subjective parameters, including the results of a physical examination. The term "treating" includes prevention of an injury, pathology, condition, or disease. "Treating" in reference to a treating a symptom of a dry eye disease refers to: (i) reducing the severity of one or more symptoms; (ii) eliminating one or more symptoms; (iii) reducing the duration of one or more symptoms; (iv) preventing the recurrence or onset of one or more symptoms; or (iv) a combination of two or more thereof.

A "therapeutically effective amount" is an amount of the active agent sufficient to accomplish a stated purpose, e.g., achieve the effect for which it is administered (i.e., increasing tear production), treat a dry eye disease, or reduce one or more symptoms of dry eye disease in a patient. A "therapeutically effective amount" is an amount of the active agent sufficient to contribute to the treatment, prevention, or reduction of a symptom or symptoms of a disease. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In embodiments, the "therapeutically effective amount" is the amount described herein.

Dosages of the active agent may be varied depending upon the requirements of the patient and the active agent being employed. The dose administered to a patient should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment can optionally be initiated with smaller dosages which are less than the optimum dose of the active agent. Thereafter, the dosage is increased by small increments until the optimum effect under circumstances is reached. Dosage amounts and intervals can be adjusted individually to provide levels of the administered active agent effective for the particular clinical indication being treated. This will provide a therapeutic regimen that is commensurate with the severity of the individual's disease state. Appropriate dosages for increasing tear production and treating dry eye disease are described in detail herein.

The dosage and frequency (once/daily, twice/daily) of the active agent administered to a patient can vary depending upon a variety of factors, for example, whether the patient suffers from another disease, and its route of administration; size, age, sex, health, body weight, body mass index, and diet of the patient; nature and extent of symptoms of the disease being treated, kind of concurrent treatment, complications from the disease being treated or other health-related problems. Other therapeutic regimens or agents can be used in conjunction with the methods and active agents described herein. Adjustment and manipulation of established dosages (e.g., frequency and duration) are well within the ability of those skilled in the art. As discussed in detail herein, the active agents and compositions may be administered once or twice per day. In embodiments, the active agents and compositions described herein may be administered once per day for about two weeks. In embodiments, the active agents and compositions described herein may be administered once per day for about one month. In embodiments, the active agents and compositions described herein may be administered twice per day for about two weeks. In embodiments, the active agents and compositions described herein may be administered twice per day for about one month.

A "week" is from about 13 days to about 15 days. In embodiments, a week is 14 days.

A "month" is 28 days, 29 days, 30, days, or 31 days. In embodiments, a month is 28 days. In embodiments, a month is 30 days. In embodiments, a month is 31 days.

The active agents and compositions described herein can be used in combination with one or more other drugs known to be useful in treating dry eye disease or increasing tear production. The active agents and compositions described herein can be used with adjunctive agents that may not be effective alone, but may contribute to the efficacy of the active agent. Thus, the active agents described herein may be co-administered with one or more other drugs that are useful to treat dry eye disorder or increase tear production in patients. Exemplary drugs used to treat dry eye disorder or to increase tear production include epithelial sodium channel inhibitors, lymphocyte function-associated antigen-1 antagonists, anti-inflammatory agents, cholinergic agonists, steroids, antibiotics, and the like. An exemplary epithelial sodium channel inhibitor is amiloride. An exemplary lymphocyte function-associated antigen-1 antagonist is lifitegrast. An exemplary anti-inflammatory agent is cyclosporine. Exemplary cholinergic agonists are pilocarpine and cevimeline. An exemplary steroid is a corticosteroid.

By "co-administer" it is meant that active agent or compositions described herein are administered at the same time, prior to (e.g., minutes or hours), or after (e.g., minutes or hours) the administration of one or more additional therapies. The active agents described herein can be administered alone or can be co-administered to the patient. Co-administration is meant to include simultaneous or sequential administration of the active agent individually or in combination. Thus, the preparations can also be combined, when desired, with other active substances.

Co-administration includes administering one active agent within 0.5, 1, 2, 4, 6, 8, 10, 12, 16, 20, or 24 hours of a second pharmaceutical compound (e.g. anti-dry eye agents). Also contemplated herein, are embodiments, where co-administration includes administering one active agent within 0.5, 1, 2, 4, 6, 8, 10, 12, 16, 20, or 24 hours of a another pharmaceutical compound. Co-administration includes administering the active agent and other pharmaceutical compound simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both the active agent and the other pharmaceutical compound. In other embodiments, the active agent and other pharmaceutical compound can be formulated separately.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Pharmaceutically acceptable excipient" and "pharmaceutically acceptable carrier" refer to a substance that aids the administration of an active agent to and absorption by a patient and can be included in the compositions described herein. Exemplary pharmaceutically acceptable excipients include stabilizers, co-solvents, and the like. Other non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with other pharmaceutically acceptable excipients such as lubricants, preservatives, stabilizers, wetting agents, emulsifiers, salts for influencing osmotic pressure, buffers, coloring, and/or aromatic substances and the like.

A "stabilizer" refers to a pharmaceutically acceptable excipient that maintains the properties of the active agents described herein and/or that delays or prevents physical or chemical degradation of the active agents described herein. Exemplary stabilizers include microcrystalline cellulose, carboxymethyl cellulose, hydromellose, dextran, and the like.

"Co-solvent" refers to pharmaceutically acceptable excipients that can increase, maintain, or prolong the solubility of the active agents. Exemplary co-solvents include sorbitol, glycerol, propylene glycol, polyethylene glycol, polyvinyl alcohol, polysorbate, and the like.

"Administering" means topical administration of the active agents and compositions described herein to one or both eyes of a patient. In embodiments, the topical administration is topical administration to the conjunctiva of the eye. In embodiments, the topical administration is topical administration to the conjunctival sac of the eye. In embodiments, the topical administration is topical administration to the conjunctiva of the eye and the conjunctival sac of the eye. The active agents and compositions described herein can be delivered topically as a liquid formulation. In embodiments, the topical liquid formulation is a solution. In embodiments, the topical liquid formulation is an aqueous solution. In embodiments, the topical liquid formulation is a suspension. In embodiments, the topical liquid formulation is an emulsion.

"Solution" has the plain and ordinary meaning as used in the chemical and biological arts, and refers to a formulation in which an active agent is dissolved in a suitable solvent (e.g., aqueous solvent, organic solvent).

"Suspension" has the plain and ordinary meaning as used in the chemical and biological arts, and refers to a formulation in which an insoluble active agent is dispersed in a suitable solvent (e.g., aqueous solvent, organic solvent).

"Emulsion" has the plain and ordinary meaning as used in the chemical and biological arts, and refers to two or more immiscible liquids in which one liquid is uniformly dispersed throughout the other liquid. The active agent may be present in one or both immiscible liquids "Micronized" refers to the active agent having a particle size distribution D90 of about 25 microns or less or to a particle size range from about 1 micron to about 25 microns. In embodiments, micronized particles of the active agent have a particle size distribution D90 of about 20 microns or less, or about 15 microns or less, or about 10 microns or less. In embodiments, micronized particles of the active agent have a particle size range from about 1 micron to about 20 microns, or about 2 microns to about 15 microns, or about 2 microns to about 10 microns. Methods of micronizing pharmaceutical compounds are conventional and well known in the art of pharmaceutical chemistry.

Methods of Treatment

The disclosure provides methods of increasing tear production in an eye of a patient in need thereof by topically administering once per day or twice per day to the eye of the patient a pharmaceutical composition comprising an active agent to increase tear production; wherein the active agent comprises a compound of Formula (I), a compound of Formula (II), a compound of Formula (III), a compound of Formula (IV), Compound A, Compound B, Compound C, Compound D, Compound E, or a pharmaceutically acceptable salt of any of the foregoing. In embodiments, the active agent is a compound of Formula (I) or a pharmaceutically acceptable salt thereof. In embodiments, the active agent is a compound of Formula (II) or a pharmaceutically acceptable salt thereof. In embodiments, the active agent is a compound of Formula (III) or a pharmaceutically acceptable salt thereof. In embodiments, the active agent is a compound of Formula (IV) or a pharmaceutically acceptable salt thereof. In embodiments, the active agent is Compound A or a pharmaceutically acceptable salt thereof. In embodiments, the active agent is Compound B or a pharmaceutically acceptable salt thereof. In embodiments, the active agent is Compound C or a pharmaceutically acceptable salt thereof. In embodiments, the active agent is Compound D or a pharmaceutically acceptable salt thereof. In embodiments, the active agent is Compound E or a pharmaceutically acceptable salt thereof. In embodiments, the pharmaceutical composition is a liquid pharmaceutical composition. In embodiments, the liquid pharmaceutical composition is a solution, a suspension, or an emulsion. In embodiments, the liquid pharmaceutical composition is an aqueous solution. In embodiments, the liquid pharmaceutical composition is a suspension; and the active agent is micronized. In embodiments, the pharmaceutical composition further comprises a pharmaceutically acceptable excipient. In embodiments, the pharmaceutically acceptable excipient is a stabilizer, a co-solvent, or a combination thereof. In embodiments, the methods comprise topically administering the pharmaceutical composition to the conjunctiva of the eye. In embodiments, the methods comprise topically administering the pharmaceutical composition to the conjunctival sac of the eye. In embodiments, the pharmaceutical composition is administered once per day. In embodiments, the pharmaceutical composition is administered twice per day. In embodiments, the composition is administered for about 14 days. In embodiments, the composition is administered for about one month. In embodiments, the methods further comprise administering an epithelial sodium channel inhibitor, a lymphocyte function-associated antigen-1 antagonist, an anti-inflammatory agent, a cholinergic agonist, a steroid, an antibiotic, or a combination of two or more thereof. In embodiments, the epithelial sodium channel inhibitor is amiloride; wherein the lymphocyte function-associated antigen-1 antagonist is lifitegrast; wherein the anti-inflammatory agent is cyclosporine; wherein the cholinergic agonist is pilocarpine or cevimeline; and wherein the steroid is a corticosteroid. In embodiments, the patient is a human. In embodiments, the patient has an open-circuit transepithelial potential difference on the eye that is lower than that of a control. In embodiments, the methods further comprise measuring the change in the open-circuit transepithelial potential difference, in response to contact with different solutions, at the surface of the eye of the patient, and comparing the result to a control.

The disclosure provides methods of treating a dry eye disease in a patient in need thereof by topically administering once per day or twice per day to an eye of the patient a pharmaceutical composition comprising an active agent to treat the dry eye disease; wherein the active agent comprises a compound of Formula (I), a compound of Formula (II), a compound of Formula (III), a compound of Formula (IV), Compound A, Compound B, Compound C, Compound D, Compound E, or a pharmaceutically acceptable salt of any of the foregoing. In embodiments, the disclosure provides methods of treating a symptom of dry eye disease in a patient in need thereof by topically administering once per day or twice per day to an eye of the patient a pharmaceutical composition comprising an active agent to treat the symptom of the dry eye disease; wherein the active agent comprises a compound of Formula (I), a compound of Formula (II), a compound of Formula (III), a compound of Formula (IV), Compound A, Compound B, Compound C, Compound D, Compound E, or a pharmaceutically acceptable salt of any of the foregoing. In embodiments, the active agent is a compound of Formula (I) or a pharmaceutically acceptable salt thereof. In embodiments, the active agent is a compound of Formula (II) or a pharmaceutically acceptable salt thereof. In embodiments, the active agent is a compound of Formula (III) or a pharmaceutically acceptable salt thereof. In embodiments, the active agent is a compound of Formula (IV) or a pharmaceutically acceptable salt thereof. In embodiments, the active agent is Compound A or a pharmaceutically acceptable salt thereof. In embodiments, the active agent is Compound B or a pharmaceutically acceptable salt thereof. In embodiments, the active agent is Compound C or a pharmaceutically acceptable salt thereof. In embodiments, the active agent is Compound D or a pharmaceutically acceptable salt thereof. In embodiments, the active agent is Compound E or a pharmaceutically acceptable salt thereof. In embodiments, the pharmaceutical composition is a liquid pharmaceutical composition. In embodiments, the liquid pharmaceutical composition is a solution, a suspension, or an emulsion. In embodiments, the liquid pharmaceutical composition is an aqueous solution. In embodiments, the liquid pharmaceutical composition is a suspension; and active agent is micronized. In embodiments, the pharmaceutical composition further comprises a pharmaceutically acceptable excipient. In embodiments, the pharmaceutically acceptable excipient is a stabilizer, a co-solvent, or a combination thereof. In embodiments, the methods comprise topically administering the pharmaceutical composition to the conjunctiva of the eye. In embodiments, the methods comprise topically administering the pharmaceutical composition to the conjunctival sac of the eye. In embodiments, the pharmaceutical composition is administered once per day. In embodiments, the pharmaceutical composition is administered twice per day. In embodiments, the composition is administered for about 14 days. In embodiments, the composition is administered for about one month. In embodiments, the methods further comprise administering a epithelial sodium channel inhibitor, a lymphocyte function-associated antigen-1 antagonist, an anti-inflammatory agent, a cholinergic agonist, a steroid, an antibiotic, or a combination of two or more thereof. In embodiments, the epithelial sodium channel inhibitor is amiloride; wherein the lymphocyte function-associated antigen-1 antagonist is lifitegrast; wherein the anti-inflammatory agent is cyclosporine; wherein the cholinergic agonist is pilocarpine or cevimeline; and wherein the steroid is a corticosteroid. In embodiments, the patient is a human. In embodiments, the patient has open-circuit transepithelial potential difference on the eye that is lower than that of a control. In embodiments, the methods further comprise measuring the change in the open-circuit transepithelial potential difference, in response to contact with different solutions, at the surface of the eye of the patient, and comparing the result to a control.

The disclosure provides methods of increasing tear production in an eye of a patient in need thereof by topically administering to the eye of the patient a pharmaceutical composition comprising a therapeutically effective amount of an active agent to increase tear production; wherein the active agent comprises a compound of Formula (I), a compound of Formula (II), a compound of Formula (III), a compound of Formula (IV), Compound A, Compound B, Compound C, Compound D, Compound E, or a pharmaceutically acceptable salt of any of the foregoing. In embodiments, the active agent is a compound of Formula (I) or a pharmaceutically acceptable salt thereof. In embodiments, the active agent is a compound of Formula (II) or a pharmaceutically acceptable salt thereof. In embodiments, the active agent is a compound of Formula (III) or a pharmaceutically acceptable salt thereof. In embodiments, the active agent is a compound of Formula (IV) or a pharmaceutically acceptable salt thereof. In embodiments, the active agent is Compound A or a pharmaceutically acceptable salt thereof. In embodiments, the active agent is Compound B or a pharmaceutically acceptable salt thereof. In embodiments, the active agent is Compound C or a pharmaceutically acceptable salt thereof. In embodiments, the active agent is Compound D or a pharmaceutically acceptable salt thereof. In embodiments, the active agent is Compound E or a pharmaceutically acceptable salt thereof. In embodiments, the pharmaceutical composition is a liquid pharmaceutical composition. In embodiments, the liquid pharmaceutical composition is a solution, a suspension, or an emulsion. In embodiments, the liquid pharmaceutical composition is an aqueous solution. In embodiments, the liquid pharmaceutical composition is a suspension; the active agent is micronized. In embodiments, the pharmaceutical composition further comprises a pharmaceutically acceptable excipient. In embodiments, the pharmaceutically acceptable excipient is a stabilizer, a co-solvent, or a combination thereof. In embodiments, the methods comprise topically administering the pharmaceutical composition to the conjunctiva of the eye. In embodiments, the methods comprise topically administering the pharmaceutical composition to the conjunctival sac of the eye. In embodiments, the pharmaceutical composition is administered once per day. In embodiments, the pharmaceutical composition is administered twice per day. In embodiments, the composition is administered for about 14 days. In embodiments, the composition is administered for about one month. In embodiments, the methods further comprise administering a epithelial sodium channel inhibitor, a lymphocyte function-associated antigen-1 antagonist, an anti-inflammatory agent, a cholinergic agonist, a steroid, an antibiotic, or a combination of two or more thereof. In embodiments, the epithelial sodium channel inhibitor is amiloride; wherein the lymphocyte function-associated antigen-1 antagonist is lifitegrast; wherein the anti-inflammatory agent is cyclosporine; wherein the cholinergic agonist is pilocarpine or cevimeline; and wherein the steroid is a corticosteroid. In embodiments, the patient is a human. In embodiments, the patient has an open-circuit transepithelial potential difference on the eye that is lower than that of a control. In embodiments, the methods further comprise measuring the change in the open-circuit transepithelial potential difference, in response to contact with different solutions, at the surface of the eye of the patient, and comparing the result to a control.

In embodiments of the methods of increasing tear production described herein, the pharmaceutical composition comprises a therapeutically effective amount of an active agent; wherein the therapeutically effective amount of the active agent is about 1 microgram or more. In embodiments, the therapeutically effective amount of the active agent is from about 1 microgram to about 100 micrograms. In embodiments, the therapeutically effective amount of the active agent is from about 5 micrograms to about 100 micrograms. In embodiments, the therapeutically effective amount of the active agent is from about 5 micrograms to about 75 micrograms. In embodiments, the therapeutically effective amount of the active agent is from about 5 micrograms to about 50 micrograms. In embodiments, the therapeutically effective amount of the active agent is from about 5 micrograms to about 35 micrograms. In embodiments, the therapeutically effective amount of the active agent is from about 5 micrograms to about 20 micrograms. In embodiments, the therapeutically effective amount of the active agent is from about 5 micrograms to about 15 micrograms. In embodiments, the therapeutically effective amount of the active agent is from about 8 micrograms to about 12 micrograms. In embodiments, the therapeutically effective amount of the active agent is about 10 micrograms. In embodiments, the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

In embodiments of the methods of increasing tear production described herein, the pharmaceutical composition comprises a therapeutically effective amount of the active agent; wherein the therapeutically effective amount is about 2 nanomoles or more. In embodiments, the therapeutically effective amount of the active agent is from about 2 nanomoles to about 100 nanomoles. In embodiments, the therapeutically effective amount of the active agent is from about 2 nanomoles to about 75 nanomoles. In embodiments, the therapeutically effective amount of the active agent is from about 2 nanomoles to about 50 nanomoles. In embodiments, the therapeutically effective amount of the active agent is from about 2 nanomoles to about 25 nanomoles. In embodiments, the therapeutically effective amount of the active agent is from about 2 nanomoles to about 15 nanomoles. In embodiments, the therapeutically effective amount of the active agent is from about 2 nanomoles to about 10 nanomoles. In embodiments, the therapeutically effective amount of the active agent is from about 2 nanomoles to about 5 nanomoles. In embodiments, the therapeutically effective amount of the active agent is about 3 nanomoles. In embodiments, the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides methods of treating a dry eye disease in a patient in need thereof by topically administering to an eye of the patient a pharmaceutical composition comprising a therapeutically effective amount of an active agent to treat the dry eye disease; wherein the active agent comprises a compound of Formula (I), a compound of Formula (II), a compound of Formula (III), a compound of Formula (IV), Compound A, Compound B, Compound C, Compound D, Compound E, or a pharmaceutically acceptable salt of any of the foregoing. In embodiments, the disclosure provides methods of treating a symptom of dry eye disease in a patient in need thereof by topically administering to an eye of the patient a pharmaceutical composition comprising a therapeutically effective amount of an active agent to treat the symptom of the dry eye disease; wherein the active agent comprises a compound of Formula (I), a compound of Formula (II), a compound of Formula (III), a compound of Formula (IV), Compound A, Compound B, Compound C, Compound D, Compound E, or a pharmaceutically acceptable salt of any of the foregoing. In embodiments, the active agent is a compound of Formula (I) or a pharmaceutically acceptable salt thereof. In embodiments, the active agent is a compound of Formula (II) or a pharmaceutically acceptable salt thereof. In embodiments, the active agent is a compound of Formula (III) or a pharmaceutically acceptable salt thereof. In embodiments, the active agent is a compound of Formula (IV) or a pharmaceutically acceptable salt thereof. In embodiments, the active agent is Compound A or a pharmaceutically acceptable salt thereof. In embodiments, the active agent is Compound B or a pharmaceutically acceptable salt thereof. In embodiments, the active agent is Compound C or a pharmaceutically acceptable salt thereof. In embodiments, the active agent is Compound D or a pharmaceutically acceptable salt thereof. In embodiments, the active agent is Compound E or a pharmaceutically acceptable salt thereof. In embodiments, the pharmaceutical composition is a liquid pharmaceutical composition. In embodiments, the liquid pharmaceutical composition is a solution, a suspension, or an emulsion. In embodiments, the liquid pharmaceutical composition is an aqueous solution. In embodiments, the pharmaceutical composition further comprises a pharmaceutically acceptable excipient. In embodiments, the pharmaceutically acceptable excipient is a stabilizer, a co-solvent, or a combination thereof. In embodiments, the methods comprise topically administering the pharmaceutical composition to the conjunctiva of the eye. In embodiments, the methods comprise topically administering the pharmaceutical composition to the conjunctival sac of the eye. In embodiments, the pharmaceutical composition is administered once per day. In embodiments, the pharmaceutical composition is administered twice per day. In embodiments, the composition is administered for about 14 days. In embodiments, the composition is administered for about one month. In embodiments, the methods further comprise administering a epithelial sodium channel inhibitor, a lymphocyte function-associated antigen-1 antagonist, an anti-inflammatory agent, a cholinergic agonist, a steroid, an antibiotic, or a combination of two or more thereof. In embodiments, the epithelial sodium channel inhibitor is amiloride; wherein the lymphocyte function-associated antigen-1 antagonist is lifitegrast; wherein the anti-inflammatory agent is cyclosporine; wherein the cholinergic agonist is pilocarpine or cevimeline; and wherein the steroid is a corticosteroid. In embodiments, the patient is a human. In embodiments, the patient has an open-circuit transepithelial potential difference on the eye that is lower than that of a control. In embodiments, the methods further comprise measuring the change in the open-circuit transepithelial potential difference, in response to contact with different solutions, at the surface of the eye of the patient, and comparing the result to a control.

In embodiments of the methods of treating a dry eye disease described herein, the pharmaceutical composition comprises a therapeutically effective amount of the active agent; wherein the therapeutically effective amount is about 1 microgram or more. In embodiments of the methods of treating a symptom of dry eye disease described herein, the pharmaceutical composition comprises a therapeutically effective amount of the active agent; wherein the therapeutically effective amount is about 1 microgram or more. In embodiments, the therapeutically effective amount of the active agent is about 5 micrograms or more. In embodiments, the therapeutically effective amount of the active agent is from about 1 microgram to about 100 micrograms. In embodiments, the therapeutically effective amount of the active agent is from about 5 micrograms to about 100 micrograms. In embodiments, the therapeutically effective amount of the active agent is from about 5 micrograms to about 75 micrograms. In embodiments, the therapeutically effective amount of the active agent is from about 5 micrograms to about 50 micrograms. In embodiments, the therapeutically effective amount of the active agent is from about 5 micrograms to about 35 micrograms. In embodiments, the therapeutically effective amount of the active agent is from about 5 micrograms to about 20 micrograms. In embodiments, the therapeutically effective amount of the active agent is from about 5 micrograms to about 15 micrograms. In embodiments, the therapeutically effective amount of the active agent is from about 8 micrograms to about 12 micrograms. In embodiments, the therapeutically effective amount of the active agent is about 10 micrograms. In embodiments, the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

In embodiments of the methods of treating a dry eye disease described herein, the pharmaceutical composition comprises a therapeutically effective amount of the active agent; wherein the therapeutically effective amount of the active agent is about 2 nanomoles or more. In embodiments of the methods of treating a symptom of a dry eye disease described herein, the pharmaceutical composition comprises a therapeutically effective amount of the active agent; wherein the therapeutically effective amount of the active agent is about 2 nanomoles or more. In embodiments, the therapeutically effective amount of the active agent is from about 2 nanomoles to about 100 nanomoles. In embodiments, the therapeutically effective amount of the active agent is from about 2 nanomoles to about 75 nanomoles. In embodiments, the therapeutically effective amount of the active agent is from about 2 nanomoles to about 50 nanomoles. In embodiments, the therapeutically effective amount of the active agent is from about 2 nanomoles to about 25 nanomoles. In embodiments, the therapeutically effective amount of the active agent is from about 2 nanomoles to about 15 nanomoles. In embodiments, the therapeutically effective amount of the active agent is from about 2 nanomoles to about 10 nanomoles. In embodiments, the therapeutically effective amount of the active agent is from about 2 nanomoles to about 5 nanomoles. In embodiments, the therapeutically effective amount of the active agent is about 3 nanomoles. In embodiments, the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides methods of increasing tear production in an eye of a patient in need thereof by topically administering to the eye of the patient a pharmaceutical composition comprising a therapeutically effective amount of an active agent to increase tear production; wherein the therapeutically effective amount provides a concentration of the of the active agent in an amount of about 500 nM or more in the tear fluid of the eye about 1 hour to about 12 hours after administration; and wherein the active agent comprises a compound of Formula (I), a compound of Formula (II), a compound of Formula (III), a compound of Formula (IV), Compound A, Compound B, Compound C, Compound D, Compound E, or a pharmaceutically acceptable salt of any of the foregoing. In embodiments, the active agent is a compound of Formula (I) or a pharmaceutically acceptable salt thereof. In embodiments, the active agent is a compound of Formula (II) or a pharmaceutically acceptable salt thereof. In embodiments, the active agent is a compound of Formula (III) or a pharmaceutically acceptable salt thereof. In embodiments, the active agent is a compound of Formula (IV) or a pharmaceutically acceptable salt thereof. In embodiments, the active agent is Compound A or a pharmaceutically acceptable salt thereof. In embodiments, the active agent is Compound B or a pharmaceutically acceptable salt thereof. In embodiments, the active agent is Compound C or a pharmaceutically acceptable salt thereof. In embodiments, the active agent is Compound D or a pharmaceutically acceptable salt thereof. In embodiments, the active agent is Compound E or a pharmaceutically acceptable salt thereof. In embodiments, the pharmaceutical composition is a liquid pharmaceutical composition. In embodiments, the liquid pharmaceutical composition is a solution, a suspension, or an emulsion. In embodiments, the liquid pharmaceutical composition is an aqueous solution. In embodiments, the liquid pharmaceutical composition is a suspension; and the active agent is micronized. In embodiments, the pharmaceutical composition further comprises a pharmaceutically acceptable excipient. In embodiments, the pharmaceutically acceptable excipient is a stabilizer, a co-solvent, or a combination thereof. In embodiments, the methods comprise topically administering the pharmaceutical composition to the conjunctiva of the eye. In embodiments, the methods comprise topically administering the pharmaceutical composition to the conjunctival sac of the eye. In embodiments, the pharmaceutical composition is administered once per day. In embodiments, the pharmaceutical composition is administered twice per day. In embodiments, the composition is administered for about 14 days. In embodiments, the composition is administered for about one month. In embodiments, the methods further comprise administering a epithelial sodium channel inhibitor, a lymphocyte function-associated antigen-1 antagonist, an anti-inflammatory agent, a cholinergic agonist, a steroid, an antibiotic, or a combination of two or more thereof. In embodiments, the epithelial sodium channel inhibitor is amiloride; wherein the lymphocyte function-associated antigen-1 antagonist is lifitegrast; wherein the anti-inflammatory agent is cyclosporine; wherein the cholinergic agonist is pilocarpine or cevimeline; and wherein the steroid is a corticosteroid. In embodiments, the patient is a human. In embodiments, the patient has an open-circuit transepithelial potential difference on the eye that is lower than that of a control. In embodiments, the methods further comprise measuring the change in the open-circuit transepithelial potential difference, in response to contact with different solutions, at the surface of the eye of the patient, and comparing the result to a control.

In embodiments of the methods of increasing tear production in an eye of a patient described herein, the therapeutically effective amount provides a concentration of the active agent in an amount of about 500 nM or more in the tear fluid of the eye about 1 hour to about 12 hours after administration. In embodiments, the therapeutically effective amount provides a concentration of the active agent in an amount of (i) about 500 nM or more in the tear fluid of the eye about 30 minutes to about 3 hours after administration, or (ii) about 10 nM or more in the tear fluid of the eye about 4 hours to about to about 12 hours after administration, or (iii) both (i) and (ii). In embodiments, the therapeutically effective amount provides a concentration of the active agent in an amount from (i) about 500 nM to about 5,000 nM about 1 hour to about 3 hours after administration, or (ii) about 10 nM to about 2,000 nM about 4 hours to about 8 hours after administration, or (iii) both (i) and (ii). In embodiments, the therapeutically effective amount provides a concentration of the active agent in an amount from (i) about 500 nM to about 2,000 nM about 1 hour to about 3 hours after administration, or (ii) about 25 nM to about 1,000 nM about 4 hours to about 8 hours after administration, or (iii) both (i) and (ii). In embodiments, the therapeutically effective amount provides a concentration of the active agent in an amount from (i) about 500 nM to about 1,500 nM about 1 hour to about 3 hours after administration, or (ii) about 50 nM to about 500 nM about 5 hours to about 7 hours after administration, or (iii) both (i) and (ii). In embodiments, the therapeutically effective amount provides a concentration of the active agent in an amount from (i) about 750 nM to about 1,250 nM about 1 hour to about 3 hours after administration, or (ii) about 50 nM to about 200 nM about 5 hours to about 7 hours after administration, or (iii) both (i) and (ii). In embodiments, the therapeutically effective amount provides a concentration of the active agent in an amount from (i) about 1000 nM about 2 hours after administration, or (ii) about 100 nM about 6 hours after administration, or (iii) both (i) and (ii). In embodiments, the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides methods of treating a dry eye disease in a patient in need thereof by topically administering to an eye of the patient a pharmaceutical composition comprising a therapeutically effective amount of an active agent to treat the dry eye disease; wherein the therapeutically effective amount provides a concentration of the active agent in an amount from (i) about 500 nM or more in the tear fluid of the eye about 30 minutes to about 12 hours after administration; wherein the active agent comprises a compound of Formula (I), a compound of Formula (II), a compound of Formula (III), a compound of Formula (IV), Compound A, Compound B, Compound C, Compound D, Compound E, or a pharmaceutically acceptable salt of any of the foregoing. In embodiments, the active agent is a compound of Formula (I) or a pharmaceutically acceptable salt thereof. In embodiments, the active agent is a compound of Formula (II) or a pharmaceutically acceptable salt thereof. In embodiments, the active agent is a compound of Formula (III) or a pharmaceutically acceptable salt thereof. In embodiments, the active agent is a compound of Formula (IV) or a pharmaceutically acceptable salt thereof. In embodiments, the active agent is Compound A or a pharmaceutically acceptable salt thereof. In embodiments, the active agent is Compound B or a pharmaceutically acceptable salt thereof. In embodiments, the active agent is Compound C or a pharmaceutically acceptable salt thereof. In embodiments, the active agent is Compound D or a pharmaceutically acceptable salt thereof. In embodiments, the active agent is Compound E or a pharmaceutically acceptable salt thereof. In embodiments, the pharmaceutical composition is a liquid pharmaceutical composition. In embodiments, the liquid pharmaceutical composition is a solution, a suspension, or an emulsion. In embodiments, the liquid pharmaceutical composition is an aqueous solution. In embodiments, the liquid pharmaceutical composition is a suspension; and the active agent is micronized. In embodiments, the pharmaceutical composition further comprises a pharmaceutically acceptable excipient. In embodiments, the pharmaceutically acceptable excipient is a stabilizer, a co-solvent, or a combination thereof. In embodiments, the methods comprise topically administering the pharmaceutical composition to the conjunctiva of the eye. In embodiments, the methods comprise topically administering the pharmaceutical composition to the conjunctival sac of the eye. In embodiments, the pharmaceutical composition is administered once per day. In embodiments, the pharmaceutical composition is administered twice per day. In embodiments, the composition is administered for about 14 days. In embodiments, the composition is administered for about one month. In embodiments, the methods further comprise administering an epithelial sodium channel inhibitor, a lymphocyte function-associated antigen-1 antagonist, an anti-inflammatory agent, a cholinergic agonist, a steroid, an antibiotic, or a combination of two or more thereof. In embodiments, the epithelial sodium channel inhibitor is amiloride; wherein the lymphocyte function-associated antigen-1 antagonist is lifitegrast; wherein the anti-inflammatory agent is cyclosporine; wherein the cholinergic agonist is pilocarpine or cevimeline; and wherein the steroid is a corticosteroid. In embodiments, the patient is a human. In embodiments, the patient has an open-circuit transepithelial potential difference on the eye that is lower than that of a control. In embodiments, the methods further comprise measuring the change in the open-circuit transepithelial potential difference, in response to contact with different solutions, at the surface of the eye of the patient, and comparing the result to a control.

In embodiments of the methods of treating dry eye disease in a patient described herein, the therapeutically effective amount provides a concentration of the active agent in an amount from in an amount of about 500 nM or more in the tear fluid of the eye about 1 hour to about 12 hours after administration. In embodiments, the therapeutically effective amount provides a concentration of the active agent in an amount from (i) about 500 nM or more in the tear fluid of the eye about 30 minutes to about 3 hours after administration, or (ii) about 10 nM or more in the tear fluid of the eye about 4 hours to about to about 12 hours after administration, or (iii) both (i) and (ii). In embodiments, the therapeutically effective amount provides a concentration of the active agent in an amount from (i) about 500 nM to about 5,000 nM about 1 hour to about 3 hours after administration, or (ii) about 10 nM to about 2,000 nM about 4 hours to about 8 hours after administration, or (iii) both (i) and (ii). In embodiments, the therapeutically effective amount provides a concentration of the active agent in an amount from (i) about 500 nM to about 2,000 nM about 1 hour to about 3 hours after administration, or (ii) about 25 nM to about 1,000 nM about 4 hours to about 8 hours after administration, or (iii) both (i) and (ii). In embodiments, the therapeutically effective amount provides a concentration of the active agent in an amount from (i) about 500 nM to about 1,500 nM about 1 hour to about 3 hours after administration, or (ii) about 50 nM to about 500 nM about 5 hours to about 7 hours after administration, or (iii) both (i) and (ii). In embodiments, the therapeutically effective amount provides a concentration of the active agent in an amount from (i) about 750 nM to about 1,250 nM about 1 hour to about 3 hours after administration, or (ii) about 50 nM to about 200 nM about 5 hours to about 7 hours after administration, or (iii) both (i) and (ii). In embodiments, the therapeutically effective amount provides a concentration of the active agent in an amount from (i) about 1000 nM about 2 hours after administration, or (ii) about 100 nM about 6 hours after administration, or (iii) both (i) and (ii). In embodiments, the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

Pharmaceutical Compositions

The disclosure provides topical pharmaceutical compositions a therapeutically effective amount of an active agent and a pharmaceutically acceptable carrier; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing. In embodiments, the active agent is a compound of Formula (I) or a pharmaceutically acceptable salt thereof. In embodiments, the active agent is a compound of Formula (II) or a pharmaceutically acceptable salt thereof. In embodiments, the active agent is a compound of Formula (III) or a pharmaceutically acceptable salt thereof. In embodiments, the active agent is a compound of Formula (IV) or a pharmaceutically acceptable salt thereof. In embodiments, the active agent is Compound A or a pharmaceutically acceptable salt thereof. In embodiments, the active agent is Compound B or a pharmaceutically acceptable salt thereof. In embodiments, the active agent is Compound C or a pharmaceutically acceptable salt thereof. In embodiments, the active agent is Compound D or a pharmaceutically acceptable salt thereof. In embodiments, the active agent is Compound E or a pharmaceutically acceptable salt thereof. In embodiments, the pharmaceutical composition is a liquid pharmaceutical composition. In embodiments, the liquid pharmaceutical composition is a solution, a suspension, or an emulsion. In embodiments, the liquid pharmaceutical composition is an aqueous solution. In embodiments, the liquid pharmaceutical composition is a suspension; and the active agent is micronized. In embodiments, the pharmaceutical composition further comprises a pharmaceutically acceptable excipient. In embodiments, the pharmaceutically acceptable excipient is a stabilizer, a co-solvent, or a combination thereof.

In embodiments of the topical pharmaceutical compositions described herein, the therapeutically effective amount of the active agent is about 1 microgram or more. In embodiments, the therapeutically effective amount of the active agent is about 5 micrograms or more. In embodiments, the therapeutically effective amount of the active agent is from about 1 microgram to about 100 micrograms. In embodiments, the therapeutically effective amount of the active agent is from about 5 micrograms to about 100 micrograms. In embodiments, the therapeutically effective amount of the active agent is from about 5 micrograms to about 75 micrograms. In embodiments, the therapeutically effective amount of the active agent is from about 5 micrograms to about 50 micrograms. In embodiments, the therapeutically effective amount of the active agent is from about 5 micrograms to about 35 micrograms. In embodiments, the therapeutically effective amount of the active agent is from about 5 micrograms to about 20 micrograms. In embodiments, the therapeutically effective amount of the active agent is from about 5 micrograms to about 15 micrograms. In embodiments, the therapeutically effective amount of the active agent is from about 8 micrograms to about 12 micrograms. In embodiments, the therapeutically effective amount of the active agent is about 10 micrograms. In embodiments, the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides topical pharmaceutical compositions comprising an active agent and a pharmaceutically acceptable carrier; wherein the composition comprises the active agent at a concentration from about 1 nanomole to about 25 nmoles per 0.5 mL; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing. In embodiments, the active agent is a compound of Formula (I) or a pharmaceutically acceptable salt thereof. In embodiments, the active agent is a compound of Formula (II) or a pharmaceutically acceptable salt thereof. In embodiments, the active agent is a compound of Formula (III) or a pharmaceutically acceptable salt thereof. In embodiments, the active agent is a compound of Formula (IV) or a pharmaceutically acceptable salt thereof. In embodiments, the active agent is Compound A or a pharmaceutically acceptable salt thereof. In embodiments, the active agent is Compound B or a pharmaceutically acceptable salt thereof. In embodiments, the active agent is Compound C or a pharmaceutically acceptable salt thereof. In embodiments, the active agent is Compound D or a pharmaceutically acceptable salt thereof. In embodiments, the active agent is Compound E or a pharmaceutically acceptable salt thereof. In embodiments, the pharmaceutical composition is a liquid pharmaceutical composition. In embodiments, the liquid pharmaceutical composition is a solution, a suspension, or an emulsion. In embodiments, the liquid pharmaceutical composition is an aqueous solution. In embodiments, the pharmaceutical composition further comprises a pharmaceutically acceptable excipient. In embodiments, the pharmaceutically acceptable excipient is a stabilizer, a co-solvent, or a combination thereof.

In embodiments, the topical pharmaceutical compositions described herein comprise the active agent at a concentration from about 1 nanomole to about 50 nmoles per 0.5 mL. In embodiments, the compositions comprise the active agent at a concentration from about 1 nanomole to about 25 nmoles per 0.5 mL. In embodiments, the compositions comprise the active agent at a concentration from about 1 nanomole to about 20 nmoles per 0.5 mL. In embodiments, the compositions comprise the active agent at a concentration from about 1 nanomole to about 15 nmoles per 0.5 mL. In embodiments, the compositions comprise the active agent at a concentration from about 2 nanomoles to about 10 nmoles per 0.5 mL. In embodiments, the compositions comprise the active agent at a concentration from about 2 nanomoles to about 5 nmoles per 0.5 mL. In embodiments, the compositions comprise the active agent at a concentration from about 2 nanomoles to about 4 nmoles per 0.5 mL. In embodiments, the compositions comprise active agent at a concentration of about 3 nanomoles per 0.5 mL. In embodiments, the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

The disclosure provides eye droppers for delivering a drop of a topical pharmaceutical composition to the eye of a patient; wherein the eye dropper comprises a topical composition which comprises the active agent; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing. In embodiments, the active agent is a compound of Formula (I) or a pharmaceutically acceptable salt thereof. In embodiments, the active agent is a compound of Formula (II) or a pharmaceutically acceptable salt thereof. In embodiments, the active agent is a compound of Formula (III) or a pharmaceutically acceptable salt thereof. In embodiments, the active agent is a compound of Formula (IV) or a pharmaceutically acceptable salt thereof. In embodiments, the active agent is Compound A or a pharmaceutically acceptable salt thereof. In embodiments, the active agent is Compound B or a pharmaceutically acceptable salt thereof. In embodiments, the active agent is Compound C or a pharmaceutically acceptable salt thereof. In embodiments, the active agent is Compound D or a pharmaceutically acceptable salt thereof. In embodiments, the active agent is Compound E or a pharmaceutically acceptable salt thereof. In embodiments, the pharmaceutical composition is a liquid pharmaceutical composition. In embodiments, the liquid pharmaceutical composition is a solution, a suspension, or an emulsion. In embodiments, the liquid pharmaceutical composition is an aqueous solution. In embodiments, the pharmaceutical composition further comprises a pharmaceutically acceptable excipient. In embodiments, the pharmaceutically acceptable excipient is a stabilizer, a co-solvent, or a combination thereof.

Any eye dropper known in the art can be used to topically administer the compounds and compositions described herein. In embodiments, the eye dropper has a volume sufficient to house from about 1 drop to about 50 drops of the pharmaceutical compositions described herein. In embodiments, the eye dropper has a volume sufficient to house from about 1 drop to about 25 drops of the pharmaceutical compositions described herein. In embodiments, the eye dropper has a volume sufficient to house from about 1 drop to about 20 drops of the pharmaceutical compositions described herein. In embodiments, the eye dropper has a volume sufficient to house from about 1 drop to about 15 drops of the pharmaceutical compositions described herein. In embodiments, the eye dropper has a volume sufficient to house from about 1 drop to about 10 drops of the pharmaceutical compositions described herein. In embodiments, the eye dropper has a volume sufficient to house 1 to 5 drops of the composition. In embodiments, the eye dropper has a volume sufficient to house 1 to 4 drops of the composition. In embodiments, the eye dropper has a volume sufficient to house 1 to 3 drops of the composition. In embodiments, the eye dropper has a volume sufficient to house 1 or 2 drops of the composition.

A "drop" will be a volume of the pharmaceutical composition described herein that can provide a therapeutically effective amount of the compounds described herein when administered at the doses (e.g., 5 micrograms or more; 2 nanomoles or more) and dosing regimen (e.g., one or twice per day) described herein. In embodiments, a drop has a volume from about 10 µL to about 100 µL. In embodiments, a drop has a volume from about 20 µL to about 90 µL. In embodiments, a drop has a volume from about 30 µL to about 80 µL. In embodiments, a drop has a volume from about 40 µL to about 70 µL. In embodiments, a drop has a volume from about 50 µL to about 85 µL. In embodiments, a drop has a volume from about 30 µL to about 65 µL. In embodiments, a drop has a volume from about 40 µL to about 60 µL. In embodiments, a drop has a volume from about 55 µL to about 65 µL.

The disclosure provides kits comprising the eye droppers described herein. The kit can contain any number of eye droppers that can conveniently be used by the patient for administration of the compositions described herein. Generally the kit will contain an amount of eye droppers to meet the frequency of the dosing regimen. In embodiments, the kit will contain one eye dropper that can be re-used for the duration of the treatment regimen. In embodiments, the kit will contain seven eye droppers, sufficient to provide single use eye droppers for one week of treatment. In embodiments, the kit will contain fourteen eye droppers. In embodiments, the kit will contain twenty-eight eye droppers. In embodiments, the kit will contain fifty-six eye droppers.

The disclosure provides kits comprising an eye dropper, a container which comprises a topical pharmaceutical compositions which comprise the active agent, and instructions for use; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing. In embodiments, the active agent is a compound of Formula (I) or a pharmaceutically acceptable salt thereof. In embodiments, the active agent is a compound of Formula (II) or a pharmaceutically acceptable salt thereof. In embodiments, the active agent is a compound of Formula (III) or a pharmaceutically acceptable salt thereof. In embodiments, the active agent is a compound of Formula (IV) or a pharmaceutically acceptable salt thereof. In embodiments, the active agent is Compound A or a pharmaceutically acceptable salt thereof. In embodiments, the active agent is Compound B or a pharmaceutically acceptable salt thereof. In embodiments, the active agent is Compound C or a pharmaceutically acceptable salt thereof. In embodiments, the active agent is Compound D or a pharmaceutically acceptable salt thereof. In embodiments, the active agent is Compound E or a pharmaceutically acceptable salt thereof. In embodiments, the pharmaceutical composition is a liquid pharmaceutical composition. In embodiments, the liquid pharmaceutical composition is a solution, a suspension, or an emulsion. In embodiments, the liquid pharmaceutical composition is an aqueous solution. In embodiments, the liquid pharmaceutical composition is a suspension; and the active agent is micronized. In embodiments, the pharmaceutical composition further comprises a pharmaceutically acceptable excipient. In embodiments, the pharmaceutically acceptable excipient is a stabilizer, a co-solvent, or a combination thereof.

The kit can contain any number of eye droppers and any number of containers housing the pharmaceutical compositions that can conveniently be used by the patient for administration of the compositions described herein. Generally the kit will contain an amount of eye droppers and containers to meet the frequency of the dosing regimen. In embodiments, the kit will comprise one eye dropper and one container; where the container comprises one dose of the composition. In embodiments, the kit will comprise two eye droppers and one container; wherein the container comprises two doses of the composition. In embodiments, the kit will comprise two eye droppers and two containers; wherein each container comprises one dose of the composition. In embodiments, the kit will comprise seven eye droppers and seven containers; wherein each container comprises one dose of the composition. In embodiments, the kit will comprise fourteen eye droppers and seven containers; wherein each container comprises two doses of the composition. In embodiments, the kit will comprise fourteen eye droppers and fourteen containers; wherein each container comprises one dose of the composition.

In aspects, the disclosure provides methods of identifying a patient for treatment with a modulator of ocular surface membrane transport. In embodiments, the methods comprise the steps of: (i) measuring a change in an open-circuit transepithelial potential difference, in response to contact with different solutions, at an ocular surface of the patient; (ii) comparing the change in the open-circuit transepithelial potential difference, in response to contact with different solutions, to a control; and (iii) identifying that the patient should be treated with the modulator of ocular surface membrane transport if the change in the open-circuit transepithelial potential difference is lower than that of the control.

In aspects, the disclosure provides methods of identifying and treating a patient with a modulator of ocular surface membrane transport. In embodiments, the methods comprise the steps of: (i) measuring a change in an open-circuit transepithelial potential difference, in response to contact with different solutions, at an ocular surface of the patient; (ii) comparing the change in the open-circuit transepithelial potential difference, in response to contact with different solutions, to a control; (iii) identifying that the patient should be treated with the modulator of ocular surface membrane transport if the change in the open-circuit transepithelial potential difference is lower than that of the control; and (iv) treating the patient with a therapeutically effective amount of the modulator of ocular surface membrane transport.

Exemplary steps for measuring the change in the open-circuit transepithelial potential difference at an ocular surface of a patient are described in the examples herein. In embodiments, the method involves perfusion of the ocular surface with a series of different solutions during continuous measurement of the potential difference using a high-impedance voltmeter. Solutions containing compounds that result in depolarizations or hyperpolarizations may be identified as modulators of ocular surface membrane transport. The lower the baseline magnitude of the measurement relative to a control may indicate the greater the ability of the compound to modulate ocular surface membrane transport, which identifies compounds that will be more efficacious in increasing tear production and treating dry eye disease. In embodiments, the modulators of ocular surface membrane transport activate or increase ocular surface membrane transport. In embodiments, the modulator of ocular surface membrane transport is a CFTR agonist, such as the compounds of Formula (I) described herein.

In embodiments, the ocular surface membrane transport is an ion transporter. In embodiments, the ion transporter is a chloride transporter, a potassium transporter, or a bicarbonate transporter. In embodiments, the ocular surface membrane transport is a biomolecule transporter. In embodiments, the biomolecule transporter is a glucose transporter or a urea transporter. In embodiments, the methods further comprise treating the patient with a therapeutically effective amount of the modulator of ocular surface membrane transport. In embodiments, the modulator of ocular surface membrane transport is a CFTR agonist, a calcium-activated chloride channel activator, or an epithelial sodium channel (ENaC) inhibitor. In embodiments, the ocular surface is the cornea. In embodiments, the ocular surface is the conjunctiva.

In embodiments, the modulator of ocular surface membrane transport is a pharmaceutical composition comprising an active agent; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing. In embodiments, the active agent is a compound of Formula (I) or a pharmaceutically acceptable salt thereof. In embodiments, the active agent is a compound of Formula (II) or a pharmaceutically acceptable salt thereof. In embodiments, the active agent is a compound of Formula (III) or a pharmaceutically acceptable salt thereof. In embodiments, the active agent is a compound of Formula (IV) or a pharmaceutically acceptable salt thereof. In embodiments, the active agent is Compound A or a pharmaceutically acceptable salt thereof. In embodiments, the active agent is Compound B or a pharmaceutically acceptable salt thereof. In embodiments, the active agent is Compound C or a pharmaceutically acceptable salt thereof. In embodiments, the active agent is Compound D or a pharmaceutically acceptable salt thereof. In embodiments, the active agent is Compound E or a pharmaceutically acceptable salt thereof. In embodiments, the pharmaceutical composition is a liquid pharmaceutical composition. In embodiments, the liquid pharmaceutical composition is a solution, a suspension, or an emulsion. In embodiments, the liquid pharmaceutical composition is an aqueous solution. In embodiments, the pharmaceutical composition further comprises a pharmaceutically acceptable excipient. In embodiments, the pharmaceutically acceptable excipient is a stabilizer, a co-solvent, or a combination thereof.

The disclosure provides methods of identifying a patient for treatment with a modulator of intracellular signaling. In embodiments, the methods comprise the steps of: (i) measuring a change in an open-circuit transepithelial potential difference, in response to contact with different solutions, at an ocular surface of the patient; (ii) comparing the change in the open-circuit transepithelial potential difference, in response to contact with different solutions, to a control; and (iii) identifying that the patient should be treated with the modulator of intracellular signaling if the change in the open-circuit transepithelial potential difference is lower than that of the control. In embodiments, the modulator of intracellular signaling is cAMP, cGMP, or calcium signaling. In embodiments, the modulator directly modulates intracellular signaling. In embodiments, the modulator indirectly modulates intracellular signaling. In embodiments, the ocular surface is the cornea or the conjunctiva.

Compounds

In embodiments, the active agent is a compound of Formula (I) or a pharmaceutically acceptable salt thereof:

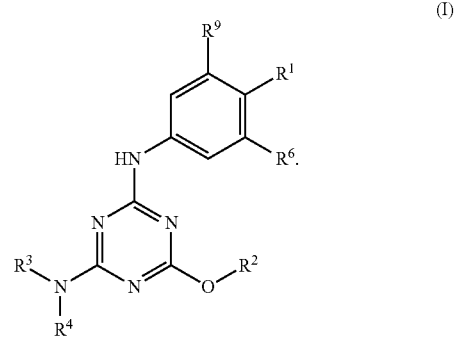

(I)

In the compound of Formula (I), $R^1$ is (i) hydrogen, (ii) $R^1$ and $R^6$ are joined to form, together with the atoms to which they are attached, a substituted (e.g., with a substituent group) or unsubstituted $C_8$-$C_{10}$ heterocycloalkyl or a substituted (e.g., with a substituent group) or unsubstituted $C_8$-$C_{10}$ heteroaryl; or (iii) $R^1$ and $R^9$ are joined to form, together with the atoms to which they are attached, a substituted (e.g., with a substituent group) or unsubstituted $C_8$-$C_{10}$ heterocycloalkyl or a substituted (e.g., with a substituent group) or unsubstituted $C_8$-$C_{10}$ heteroaryl. In embodiments, $R^1$ is hydrogen. In embodiments, $R^1$ and $R^6$ are joined to form, together with the atoms to which they are attached, a substituted (e.g., with a substituent group) or unsubstituted $C_8$-$C_{10}$ heterocycloalkyl or a substituted (e.g., with a substituent group) or unsubstituted $C_8$-$C_{10}$ heteroaryl. In embodiments, $R^1$ and $R^9$ are joined to form, together with the atoms to which they are attached, a substituted (e.g., with a substituent group) or unsubstituted $C_8$-$C_{10}$ heterocycloalkyl or a substituted or unsubstituted $C_8$-$C_{10}$ heteroaryl. In embodiments, $R^1$ is (i) hydrogen, (ii) $R^1$ and $R^6$ are joined to form, together with the atoms to which they are attached, an unsubstituted $C_8$-$C_{10}$ heterocycloalkyl or an unsubstituted $C_8$-$C_{10}$ heteroaryl; or (iii) $R^1$ and $R^9$ are joined to form, together with the atoms to which they are attached, an unsubstituted $C_8$-$C_{10}$ heterocycloalkyl or an or unsubstituted $C_8$-$C_{10}$ heteroaryl. In embodiments, $R^1$ is (i) hydrogen, or (ii) $R^1$ and $R^6$ are joined to form, together with the atoms to which they are attached, an unsubstituted $C_8$-$C_{10}$ heterocycloalkyl or an unsubstituted $C_8$-$C_{10}$ heteroaryl. In embodiments, the substituents for the substituted $C_8$-$C_{10}$ heterocycloalkyl are set forth in the definition of "substituents" (e.g., a substituent group). In embodiments, the substituents for the substituted $C_8$-$C_{10}$ heterocycloalkyl are set forth in the definition of "size-limited substituent" (e.g., size-limited substituent group). In embodiments, the substituents for the substituted $C_8$-$C_{10}$ heterocycloalkyl are set forth in the definition of "lower substituent" (e.g., lower substituent group). In embodiments, the substituents for the substituted $C_8$-$C_{10}$ heteroaryl are set forth in the definition of "substituents" (e.g., a substituent group). In embodiments, the substituents for the substituted $C_8$-$C_{10}$ heteroaryl are set forth in the definition of "size-limited substituent" (e.g., size-limited substituent group). In embodiments, the substituents for the substituted $C_8$-$C_{10}$ heteroaryl are set forth in the definition of "lower substituent" (e.g., lower substituent group).

In the compound of Formula (I), $R^2$ is a $C_2$-$C_4$ haloalkyl.

In the compound of Formula (I), $R^3$ is hydrogen or a $C_1$-$C_3$ alkyl.

In the compound of Formula (I), $R^4$ is hydrogen or a $C_1$-$C_3$ alkyl.

In the compound of Formula (I), $R^6$ is (i) hydrogen or (ii) $R^1$ and $R^6$ are joined to form, together with the atoms to which they are attached, a substituted (e.g., with a substituent group) or unsubstituted $C_8$-$C_{10}$ heterocycloalkyl or a substituted (e.g., with a substituent group) or unsubstituted $C_8$-$C_{10}$ heteroaryl. In embodiments, $R^6$ is hydrogen. In embodiments, $R^1$ and $R^6$ are joined to form, together with the atoms to which they are attached, a substituted (e.g., with a substituent group) or unsubstituted $C_8$-$C_{10}$ heterocycloalkyl or a substituted (e.g., with a substituent group) or unsubstituted $C_8$-$C_{10}$ heteroaryl.

In the compound of Formula (I), $R^9$ is (i) hydrogen or (ii) $R^1$ and $R^9$ are joined to form, together with the atoms to which they are attached, a substituted (e.g., with a substituent group) or unsubstituted $C_8$-$C_{10}$ heterocycloalkyl or a substituted (e.g., with a substituent group) or unsubstituted $C_8$-$C_{10}$ heteroaryl. In embodiments, $R^9$ is hydrogen. In embodiments, $R^1$ and $R^9$ are joined to form, together with the atoms to which they are attached, a substituted (e.g., with a substituent group) or unsubstituted $C_8$-$C_{10}$ heterocycloalkyl or a substituted (e.g., with a substituent group) or unsubstituted $C_8$-$C_{10}$ heteroaryl.

In embodiments, the active agent is a compound of Formula (II) or a pharmaceutically acceptable salt thereof:

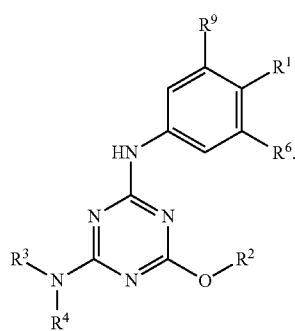

(II)

In the compounds of Formula (II), $R^1$ and $R^6$ or $R^1$ and $R^9$ are joined to form, together with the atoms to which they are attached, a $C_9$ heteroaryl, wherein $R^1$ and $R^6$ or $R^1$ and $R^9$ are —X1-CH=X2-, wherein X1 and X2 are each independently —O—, —N=, or —S—. In embodiments, $R^1$ and $R^6$ are joined to form, together with the atoms to which they are attached, a $C_9$ heteroaryl, wherein $R^1$ and $R^6$ are —X1-CH=X2-, wherein $X_1$ and $X_2$ are each independently —O—, —N=, or —S—. In embodiments, $R^1$ and $R^9$ are joined to form, together with the atoms to which they are attached, a $C_9$ heteroaryl, wherein $R^1$ and $R^9$ are —X1-CH=X2-, wherein X1 and X2 are each independently —O—, —N=, or —S—. In embodiments, X1 and X2 are not both oxygen, nitrogen, or sulfur. In embodiments, X1 is —N= and X2 is —S—. In embodiments, X1 is —S— and X2 is —N=. In embodiments, X1 is —N= and $X_2$ is —O—. In embodiments, X1 is —O— and X2 is —S—.

In the compounds of Formula (II), $R^2$ is —CH(CF$_3$)$_2$ or —CH$_2$CF$_2$CF$_2$H. In embodiments, $R^2$ is —CH(CF$_3$)$_2$. In embodiments, $R^2$ is —CH$_2$CF$_2$CF$_2$H.

In the compounds of Formula (II), $R^3$ is hydrogen, methyl, or ethyl. In embodiments, $R^3$ is hydrogen. In embodiments, $R^3$ is methyl. In embodiments, $R^3$ is ethyl.

In the compounds of Formula (II), $R^4$ is hydrogen, methyl, or ethyl. In embodiments, $R^4$ is hydrogen. In embodiments, $R^4$ is methyl. In embodiments, $R^4$ is ethyl.

In the compounds of Formula (II), $R^6$ is (i) hydrogen or (ii) $R^1$ and $R^6$ are joined to form, together with the atoms to which they are attached, a $C_9$ heteroaryl wherein $R^1$ and $R^6$ are —X1-CH=X2- and X1 is —O— or —N= and X2 is =N— or —O—. In embodiments, $R^6$ is hydrogen. In embodiments, $R^1$ and $R^6$ are joined to form, together with the atoms to which they are attached, a $C_9$ heteroaryl wherein $R^1$ and $R^6$ are —X—CH—X2- and X1 is —O— or —N= and X2 is =N— or —O—.

In the compounds of Formula (II), $R^9$ is (i) hydrogen or (ii) $R^1$ and $R^9$ are joined to form, together with the atoms to which they are attached, a $C_9$ heteroaryl wherein $R^1$ and $R^9$ are —X1-CH=X2- and X1 is —O— or —N= and X2 is =N— or —O—. In embodiments, $R^9$ is hydrogen. In embodiments, $R^1$ and $R^9$ are joined to form, together with the atoms to which they are attached, a $C_9$ heteroaryl wherein $R^1$ and $R^9$ are —X1-CH=X2- and X1 is —O— or —N= and X2 is =N— or —O—.

In embodiments, the active agent is a compound of Formula (III) or a pharmaceutically acceptable salt thereof:

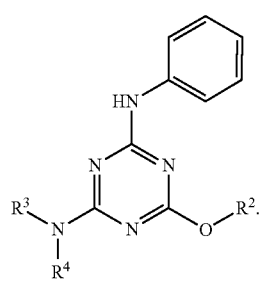

(III)

In the compounds of Formula (III), $R^2$ is —CH(CF$_3$)$_2$ or —CH$_2$CF$_2$CF$_2$H. In embodiments, $R^2$ is —CH(CF$_3$)$_2$. In embodiments, $R^2$ is —CH$_2$CF$_2$CF$_2$H.

In the compounds of Formula (III), $R^3$ is hydrogen, methyl, or ethyl. In embodiments, $R^3$ is hydrogen. In embodiments, $R^3$ is methyl. In embodiments, $R^3$ is ethyl.

In the compounds of Formula (III), $R^4$ is hydrogen, methyl, or ethyl. In embodiments, $R^4$ is hydrogen. In embodiments, $R^4$ is methyl. In embodiments, $R^4$ is ethyl.

In embodiments, the active agent is a compound of Formula (IV) or a pharmaceutically acceptable salt thereof:

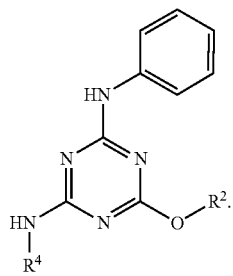

(IV)

In the compounds of Formula (IV), $R^2$ is —CH(CF$_3$)$_2$ or —CH$_2$CF$_2$CF$_2$H. In embodiments, $R^2$ is —CH(CF$_3$)$_2$. In embodiments, $R^2$ is —CH$_2$CF$_2$CF$_2$H.

In the compounds of Formula (IV), $R^4$ is hydrogen, methyl, or ethyl. In embodiments, $R^4$ is hydrogen. In embodiments, $R^4$ is methyl. In embodiments, $R^4$ is ethyl.

In embodiments, the active agent is Compound A or a pharmaceutically acceptable salt thereof:

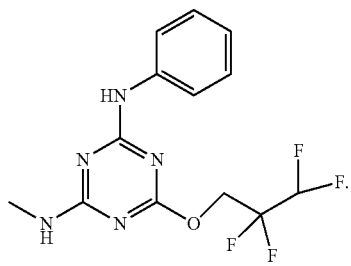

A

Compound A is also known as CFTR$_{act}$-K267 and as N-Methyl-N'-phenyl-6-(2,2,3,3-tetrafluoropropoxy)-1,3,5-triazine-2,4-diamine.

In embodiments, the active agent is Compound B or a pharmaceutically acceptable salt thereof:

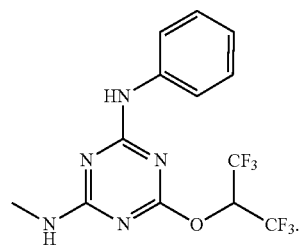

B

In embodiments, the active agent is Compound C or a pharmaceutically acceptable salt thereof:

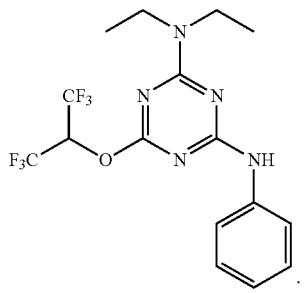

C

Compound C is also known as CFTR$_{act}$-K089.

In embodiments, the active agent is Compound D or a pharmaceutically acceptable salt thereof:

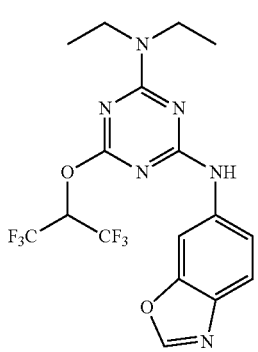

D

In embodiments, the active agent is Compound E or a pharmaceutically acceptable salt thereof:

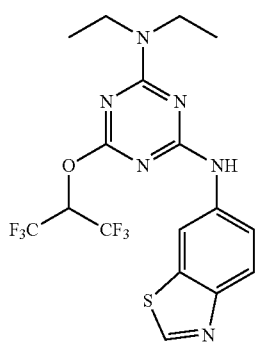

E

The compounds described herein can be made by processes known to those skilled in the art of synthetic organic chemistry. Such exemplary processes for making the compounds described herein are set forth in WO 2017/112951, the disclosure of which is incorporated by reference herein in its entirety.

The term "pharmaceutically acceptable salt" is meant to include salts of the active agents that are prepared with relatively nontoxic acids or bases, depending on the particular substituents found on the active agents described herein. When the active agents contain relatively acidic functionalities, base addition salts can be obtained by contacting the neutral form of such active agents with a sufficient amount of the desired base, either neat or in a suitable inert solvent. Examples of pharmaceutically acceptable base addition salts include sodium, potassium, calcium, ammonium, organic amino, or magnesium salt, or a similar salt. When the active agents contain relatively basic functionalities, acid addition salts can be obtained by contacting the neutral form of such active agents with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19).

The neutral forms of the active agents are regenerated by contacting the salt with a base or acid and isolating the parent active agent in the conventional manner. The parent form of the active agent differs from the various salt forms in certain physical properties, such as solubility in polar solvents and the like.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—, and —N= is equivalent to =N—.

"Alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

In embodiments, "alkyl" refers to and includes linear or branched univalent hydrocarbon structures and combination thereof, which may be fully saturated, mono- or polyunsaturated, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"), or 1 to 3 carbon atoms (a "$C_1$-$C_3$ alkyl"), or 1 to 2 carbon atoms (a "$C_1$-$C_2$ alkyl"). Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Examples of saturated $C_1$-$C_4$ alkyl include methyl ($CH_3$), ethyl ($C_2H_5$), propyl ($C_3H_7$) and butyl ($C_4H_9$). Examples of saturated $C_1$-$C_6$ alkyl include methyl ($CH_3$), ethyl ($C_2H_5$), propyl ($C_3H_7$), butyl ($C_4H_9$), pentyl ($C_5H_{11}$) and hexyl ($C_6H_{13}$). An alkyl group may be substituted (i.e., one or more hydrogen atoms are replaced with univalent or divalent radicals) with one more substituents, such as radicals described herein, for example, fluoro, chloro, bromo, iodo, hydroxyl, alkoxy, thio, amino, acylamino, alkoxycarbonylamido, carboxyl, acyl, alkoxycarbonyl, sulfonyl, cycloalkyl, aryl, heterocyclyl and heteroaryl, and other functional groups known in the art. A "perfluoroalkyl" refers to an alkyl group where every hydrogen atom is replaced with a fluorine atom. Examples of saturated $C_1$-$C_6$ perfluroalkyl include trifluoromethyl ($CF_3$), pentafluoroethyl ($C_2F_5$), heptafluoropropyl ($C_3F_7$), nonafluorobutyl ($C_4F_9$), undecafluoropentyl ($C_5F_{11}$) and tridecafluorohexyl ($C_6F_{13}$).

"Alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

"Heteroalkyl," by itself or in combination with another term, means, unless otherwise stated, a stable straight or branched chain, or combinations thereof, including at least one carbon atom and at least one heteroatom (e.g., selected from the group consisting of O, N, P, Si, and S), and wherein the nitrogen and sulfur atoms may optionally be oxidized, and the nitrogen heteroatom may optionally be quaternized. The heteroatom(s) (e.g., O, N, P, S, B, As, and Si) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CHO—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

"Heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—

CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R'', —OR', —SR', and/or —SO$_2$R'. Where "heteroalkyl" is recited, followed by recitations of specific heteroalkyl groups, such as —NR'R'' or the like, it will be understood that the terms heteroalkyl and —NR'R'' are not redundant or mutually exclusive. Rather, the specific heteroalkyl groups are recited to add clarity. Thus, the term "heteroalkyl" should not be interpreted herein as excluding specific heteroalkyl groups, such as —NR'R'' or the like.

"Cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

"Halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

"Acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

"Aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O-bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substituents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —NR'SO$_2$R", —NR'C=(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When the active agent includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C=(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When an active agent includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent" or "substituent group" or the term "substituted" (e.g., "substituted" alkyl, "substituted" heterocycloalkyl, "substituted" heteroaryl) as used herein, means a group selected from the following moieties: (A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from: (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the active agents herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the active agents herein are substituted with at least one substituent group. In other embodiments, at least one or all of these groups are substituted with at least one size-limited substituent group. In other embodiments, at least one or all of these groups are substituted with at least one lower substituent group.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In other embodiments of the active agents herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the active agents herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_5$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the active agent is a chemical species set forth in the Examples section, figures, or tables below.

Certain active agents described herein possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the disclosure. The disclosure includes active agents in racemic and optically pure forms. Optically active (R)- and (S)-, or (D)- and (L)-isomers may be prepared using chiral synthons or chiral reagents, or resolved using conventional techniques. When the active agents described herein contain olefinic bonds or other centers of geometric asymmetry, and unless specified otherwise, it is intended that the active agents include both E and Z geometric isomers.

The term "tautomer," as used herein, refers to one of two or more structural isomers which exist in equilibrium and which are readily converted from one isomeric form to another. It will be apparent to one skilled in the art that certain active agents may exist in tautomeric forms, all such tautomeric forms of the active agents being within the scope of the disclosure.

The symbol "-" denotes the point of attachment of a chemical moiety to the remainder of a molecule or chemical formula.

Description of the active agents is limited by principles of chemical bonding known to those skilled in the art. Accordingly, where a group may be substituted by one or more of a number of substituents, such substitutions are selected so as to comply with principles of chemical bonding and to give active agents which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable active agents.

EXAMPLES

The following examples are for purposes of illustration and are not intended to limit the spirit or scope of the disclosure or claims.

An attractive target for pro-secretory therapy of dry eye is CFTR (cystic fibrosis transmembrane conductance regulator), a cAMP-regulated chloride channel that is expressed in corneal and conjunctival epithelial cells as well as in various secretory epithelia outside of the eye. (References 4-11). While CFTR at the ocular surface is largely inactive under normal conditions, as it is in the intestine, once activated it can drive fluid secretion at the ocular surface, as it does in the intestine in secretory diarrheas such as cholera. (References 12, 13). As CFTR activation drives fluid secretion by epithelial cells lining the ocular surface, augmentation of tear fluid does not require functional lacrimal or Meibomian glands.

The inventors identified by high-throughput screening an aminophenyl-1,3,5-triazine class of small molecule activators of wildtype CFTR. A compound from the screen, Compound A, fully activated CFTR in cell cultures with $EC_{50}$ of about 250 nM, and, when delivered topically to mice, doubled tear volume for four hours. (Reference 14). In lacrimal gland ablation models in mice, Compound C, administered three times daily, normalized tear volume, prevented corneal epithelial disruption, and even reversed pathology when administered after development of dry eye. In a recent medicinal chemistry study, Compound C fully activated CFTR with $EC_{50}$ of about 30 nM and produced a sustained increase in tear volume in mice for 8 hours following 25 picomol topical administration. (Reference 15). Compound A was without effect in CFTR-deficient mice and was rapidly metabolized by the liver, a desirable characteristic for minimizing systemic exposure.

A total of 24 female adult New Zealand white rabbits (Western Oregon Rabbit Co., Philomath, OR) weighing 2-3 kg were used for this study. Rabbits were acclimated for 3 days prior to experiments and raised under standard laboratory conditions. Rabbit protocols were approved by the UCSF Institutional Animal Care and Use Committee and conducted in accordance with the ARVO Statement for the Use of Animals in Ophthalmic and Vision Research.

Chemicals and Formulation

Compound A was synthesized by stepwise substitution reactions of cyanuric chloride with methylamine, 2,2,3,3-tetrafluoropropanol, and aniline under basic conditions, as described in Reference 15, and purified to >95% by flash chromatography (1:2 ethyl acetate:hexane). Compound A was prepared as a 10 mM dimethyl sulfoxide (DMSO) stock solution. The ophthalmic formulation contained 0.22-μm filtered Ringer's solution containing 0.3% carboxymethyl-cellulose (CMC, high viscosity, VWR, Radnor, PA), 0.015% benzalkonium chloride (BAC) preservative, and 1% DMSO at pH 7.40. For some studies a higher concentration of CMC (0.665%) was used to increase viscosity.

Ocular Surface Potential Difference Measurements

Open-circuit transepithelial potential difference (PD, in mV) at the ocular surface was measured continuously in anesthetized rabbits using a procedure modified from that established in mice. (Reference 8). Rabbits were intubated and anesthetized with isoflurane, and respiratory rate, blood pressure and body temperature were monitored. For PD recording, solutions (see below) were serially perfused at 10 mL/min through PE-90 plastic tubing using a gravity multi-reservoir pinch-valve system (ALA Scientific, Westbury, NY) and a variable-flow peristaltic pump (medium flow model; Thermo Fisher Scientific, Fair Lawn, NJ). A probe catheter was fixed onto an adjustable stereotaxic frame with the tip immersed in solution contacting the ocular surface. Excess fluid was aspirated by continuous suction (low-powered wall vacuum) using ⅛-inch tubing (inner diameter 3/32 inch) positioned 3 mm from the orbit in order to maintain near-constant perfusate volume in contact with cornea, bulbar conjunctiva and palpebral conjunctiva without fluid runoff. The measuring electrode contacted the perfusion catheter and was connected to a high-impedance voltmeter (IsoMilivolt Meter; World Precision Instruments, Sarasota, FL). The reference electrode was grounded using a winged, 25-gauge needle filled with normal saline inserted subcutaneously in the abdomen. The measuring and reference electrodes consisted of Ag/AgCl with 3 M KCl agar bridges.

Solutions consisted of: i) Normal Cl⁻ solution (mM): 99 NaCl, 24 KCl, 32 NaHCO$_3$, 1.0 NaH$_2$PO$_4$, 0.6 MgCl$_2$, 0.8 CaCl$_2$); ii) Normal Cl⁻ solution with amiloride (100 μM); iii) Low Cl⁻ solution with amiloride (NaCl replaced by Na gluconate and KCl by K gluconate); iv) Low Cl⁻+amiloride+Compound A (1 μM); v) Low Cl⁻+amiloride+Compound A (10 μM); vi) Low Cl⁻+amiloride+Compound A (10 μM)+forskolin (FSK, 20 μM); vii) Low Cl⁻+amiloride+FSK+Compound A (10 μM)+CFTR$_{inh}$-172 (3-[(3-Trifluoromethyl)phenyl]-5-[(4-carboxyphenyl)methylene]-2-thioxo-4-thiazolidinone; 10 μM). The solutions were isomolar to rabbit tear film (302 mOsm) with pH of 7.4. All solutions contained 10 M indomethacin to prevent CFTR activation by prostaglandins.

Short-Circuit Measurements

Short-circuit current was measured in freshly isolated rabbit conjunctiva, as described[16] with modification. Rabbits were euthanized by injection of 150 mg/kg euthasol into the marginal ear vein. The entire eyeball with eyelids intact was removed from the orbit to preserve conjunctival epithelium integrity. Within 10 min a sheet of forniceal and palpebral conjunctiva was dissected, mounted onto a P2304 tissue slider (Physiologic Instruments, San Diego, CA), and placed into the Ussing chamber. The apical and basolateral chambers contained (in mM): 120 NaCl, 3 KCl, 1 CaCl$_2$, 1 MgCl$_2$, 10 glucose, 25 NaHCO$_3$ and 5 HEPES, pH 7.4. Solutions were bubbled with 95% O$_2$/5% CO$_2$ and maintained at 37° C. Hemichambers were connected to a DVC-1000 voltage clamp (World Precision Instruments Inc., Sarasota, FL) via Ag/AgCl electrodes and 3 M KCl agar bridges.

Schirmer Tear Test II

Tear production was measured using the anesthetized Schirmer Tear Test (STT, Eagle Vision, Memphis TN). To minimize reflex tearing, one drop of 0.5% proparacaine hydrochloride (Akorn, Lake Forest, TL) was placed onto the corneal surface and excess fluid was absorbed at the medial canthus using eye spear sponges (Fine Science Tools, Foster City, CA). After 5 min the notched strip was inserted into the lower lateral conjunctival fornix, maintaining contact with the lateral cornea. The wetted length (mm) of the strip indicated by blue dye appearance was read after 5 min.

Pharmacodynamics

Serial STT measurements were done before and at 1, 3, 6, 9, 12 and 24 hours following application of a single 30-μL drop of Compound A formulation (or vehicle alone) into the conjunctival sac. Both eyes received the same treatment to control for potential contralateral effects of a given treatment.

Pharmacokinetics and Tissue Distribution

Compound A was quantified by liquid chromatography/mass spectroscopy (LC/MS) at 15 min, 1 hour, 2 hours, 6 hours and 24 hours after a single, 3-nmol topical dose. To recover Compound A at indicated times, three eye washes of 30 μL sterile PBS were done with solution recovered from the lateral and medial canthi after manual eyelid blinking using 50-μL glass capillary tubes. Pooled washes were diluted in three volumes of ethyl acetate, centrifuged at 13,000 rpm for 15 min, and the collected supernatant was analyzed by LC/MS (Waters 2695 HPLC with Micromass ZQ).[14] LC was done on an Xterra MS C18 column (2.1 mm×100 mm, 3.5 μm) with 0.2 mL/min water/acetonitrile containing 0.1% formic acid, 12 min linear gradient, 5-95% acetonitrile.

In chronic treatment studies, Compound A (3 nmol, or formulation control) was given twice daily (8 am and 4 pm) for 28 days. Two mL of blood was collected from the marginal ear vein in EDTA tubes. Rabbits were then euthanized using 150 mg/kg euthasol, and ocular tissues, serum and peripheral organs were collected. Using a surgical microscope, 150 μL of aqueous humor was collected through the peripheral cornea using a 25-gauge needle, and 300 μL of vitreous fluid was aspirated through the pars plana with a 23-gauge needle. Following transcardial perfusion with heparinized phosphate-buffered saline (PBS), eyes were enucleated with lids intact, and the cornea, iris/ciliary body, lens, bulbar, forniceal and palpebral conjunctiva, and retina of both eyes were dissected, weighed, homogenized in 1:4 mixture of water:ethyl acetate (10 mL/1 g tissue) and centrifuged (3000 rpm for 15 min). Plasma, aqueous and vitreous samples were each mixed with 3 volumes of ethyl acetate and centrifuged for 15 min at 13,200 rpm, and the supernatant was evaporated and re-dissolved in HPLC eluent (100 μL of 1:3 water:acetonitrile containing 0.1% formic acid) for LC/MS analysis. Also, brain, kidney, heart and liver were removed, weighed, mixed with 1:4 mixture of water: ethyl acetate (10 mL/1 g tissue), and homogenized. The homogenized samples were vortexed and centrifuged (3000 rpm for 15 min), and the ethyl acetate-containing supernatant was evaporated, and then re-dissolved in HPLC eluent for LC/MS analysis. The lower limit of detection for Compound A was ~0.2 pg/mg of homogenized tissue or biological fluid, which was defined as giving a signal-to-noise ratio >3.

Clinical Examination

In chronic treatment studies, eyes were treated twice daily for 28 days as described above. STT, intraocular pressure (IOP), and central corneal thickness were measured on days 0, 7, 14, 21 and 28. Slit lamp examinations were performed on days 0, 14 and 28 by a board-certified ophthalmologist blinded to treatment status. STT was done one hour after the first treatment of the day (9 am). IOP was measured with a Tonolab rebound tonometer (Colonial Medical Supply, Windham, NH). Central corneal thickness was measured using the Corneo-Gage Plus 2 pachymeter (Sonogage Inc., Cleveland, OH). For slit lamp examination, Lissamine green strips (GreenGlo, HUB Pharmaceuticals LLC, Rancho Cucamonga, CA) were wetted with 25 mL lubricant eye drops and then applied gently into the inferior fornix. One minute later, photographs of the eye were taken with a digital camera and staining was evaluated according to a 12-point scale as described[17]: each corneal quadrant was scored in a blinded fashion on a 3-point scale: grade 0, no staining; grade 1, sporadic staining (involving <25% of the total surface); grade 2, diffuse punctate staining (25-75%); and grade 3, coalesced punctate staining (≥75%). The total grade is reported as the sum of scores from all 4 quadrants, ranging from 0 to 12. Conjunctival congestion, chemosis, discharge, corneal haze or neovascularization, anterior chamber cellular reaction or flare, iris neovascularization, lens opacification or loss of red reflex, were each rated using a modified McDonald-Shadduck scale on a four-point scale, where zero is normal.

Histology

A subset of chronically treated eyes were enucleated with eyelids intact after transcardial perfusion with PBS followed by 4% paraformaldehyde, and left overnight in 4° C. in 30% sucrose. Eyes were embedded in OCT and sectioned through central cornea, posterior pole, and superior and inferior fornices/eyelids. Cryosections (8 μm thickness) were stained with hematoxylin and eosin (H&E) using a standard protocol.

Statistics

Data are presented as mean±S.E.M. Statistical analyses were performed using GraphPad Prism software (GraphPad, San Diego, CA). Serial tear volume measurements, IOP and corneal thickness were analyzed by two-way ANOVA with Dunnett post hoc analysis.

Results

Compound A activates CFTR chloride conductance at the rabbit ocular surface.

Figure 2A:
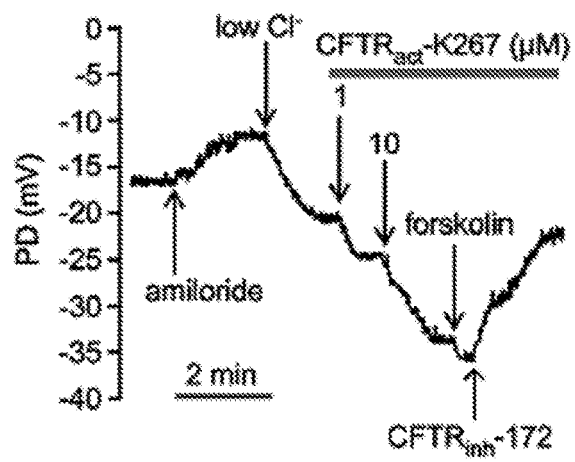
FIGS. 2A-D show an the electrophysiological analysis of CFTR activation by $CFTR_{act}$-K267 at the rabbit ocular surface.
Figure 2B:
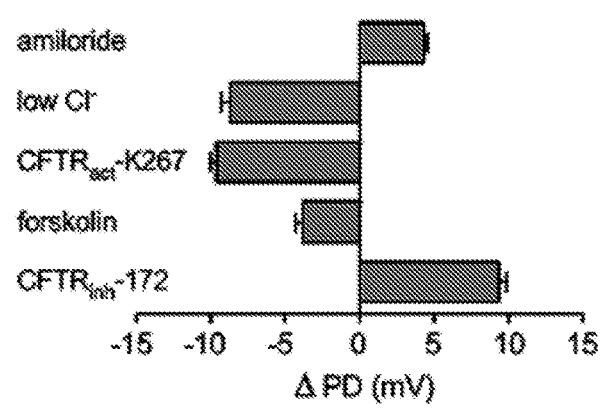

Compound A activity at the ocular surface in rabbits in vivo was measured using an open-circuit potential difference (PD) method, as developed originally in mice. The method involves perfusion of the ocular surface with a series of solutions during continuous measurement of PD using a high-impedance voltmeter, as illustrated in FIG. 1A. The average absolute PD measured initially was −14±1 mV (mean±S.E.M., n=16 eyes). The representative PD curve in FIG. 2A shows an initial depolarization following addition of the ENaC inhibitor amiloride, with hyperpolarizations following perfusion with low Cl⁻ solutions without and then with Compound A, and then with a high concentration of the cAMP agonist forskolin to maximally activate CFTR. The CFTR inhibitor $CFTR_{inh}$-172 was present in the final perfusion solution. Compound A produced a substantial depolarization that was minimally further increased by forskolin, with the depolarizations largely reversed by $CFTR_{inh}$-172. Averaged changes in PD from measurements done on 16 eyes are summarized in FIG. 2B. These results confirm activation of CFTR at the rabbit ocular surface by Compound A. However, ocular surface PD data should be considered semi-quantitative because of non-linearity in PD values with CFTR function, and because of uncertainties in the extent of perfusate fluid contact with whole ocular surface and of compound accumulation in ocular surface cells.

Figure 2C:
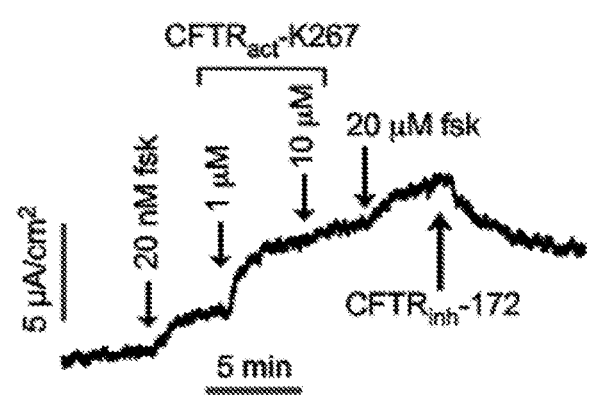
Figure 2D:
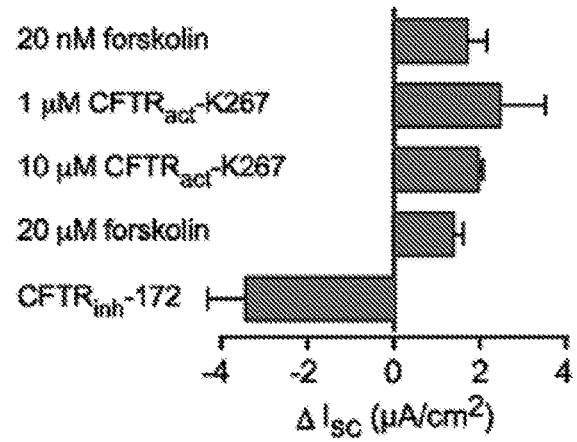

In separate electrophysiological studies, CFTR activation was measured in freshly isolated conjunctiva ex vivo by short-circuit current analysis. The representative curve in FIG. 2C shows a small increase in current in response to addition of a low concentration of forskolin (25 nM), which was further increased by 1 and then 10 M Compound A. Maximal CFTR activation was produced by a high concentration of forskolin. The increases in short-circuit current were inhibited by $CFTR_{inh}$-172. Amiloride (10 μM) had no effect on short-circuit current (not shown). Averaged changes in short-circuit current are summarized in FIG. 2D. These ex vivo results confirm Compound A activation of CFTR in conjunctival epithelium, with the data at 1 vs. 10 μM Compound A indicating an apparent $EC_{50}$<1 μM.

Compound A Pharmacodynamics

Figure 3A:
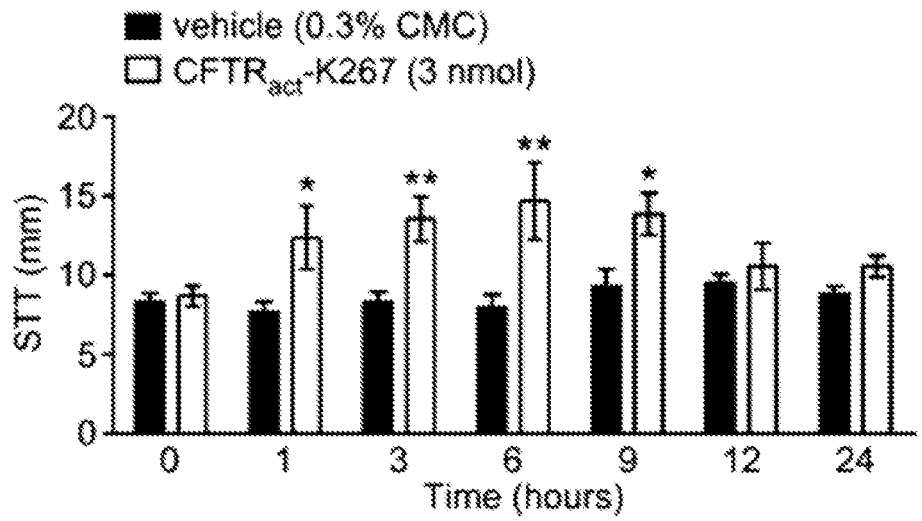
Figure 3B:
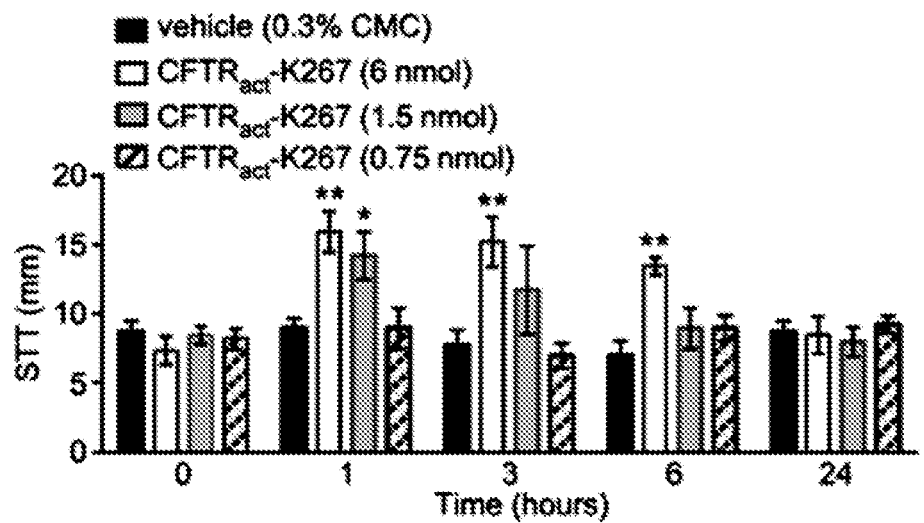
Figure 3B:
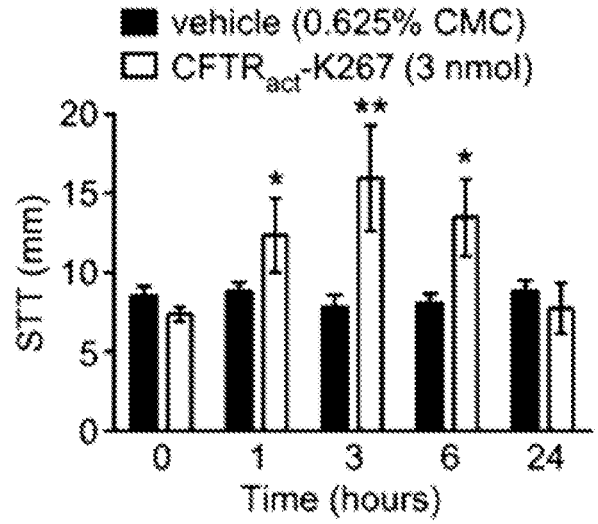

Compound A was tested for its efficacy in augmenting tear fluid production in rabbits. Prior work identified a formulation (0.325% CMC in Ringer's solution containing 0.015% BAC and 1% DMSO) that stably solubilized Compound A and was effective when delivered topically to mice.[15] A single application of 3 nmol Compound A (10 L of a 100 M solution) increased tear volume by ~60% for at least 9 hours compared to vehicle (FIG. 3A). Dose-dependence studies showed similar activity of 6 nmol Compound A, but reduced duration of activity with 1.5 nmol Compound A and no significant increase in tear production with 0.75 nmol Compound A (FIG. 3B). When 3 nmol of Compound A was delivered in a more viscous formulation containing 0.625% (instead of 0.3%) CMC, to potentially increase Compound A ocular surface residence time, compound efficacy was unchanged (FIG. 3C).

Compound A Pharmacokinetics

Figure 4A:
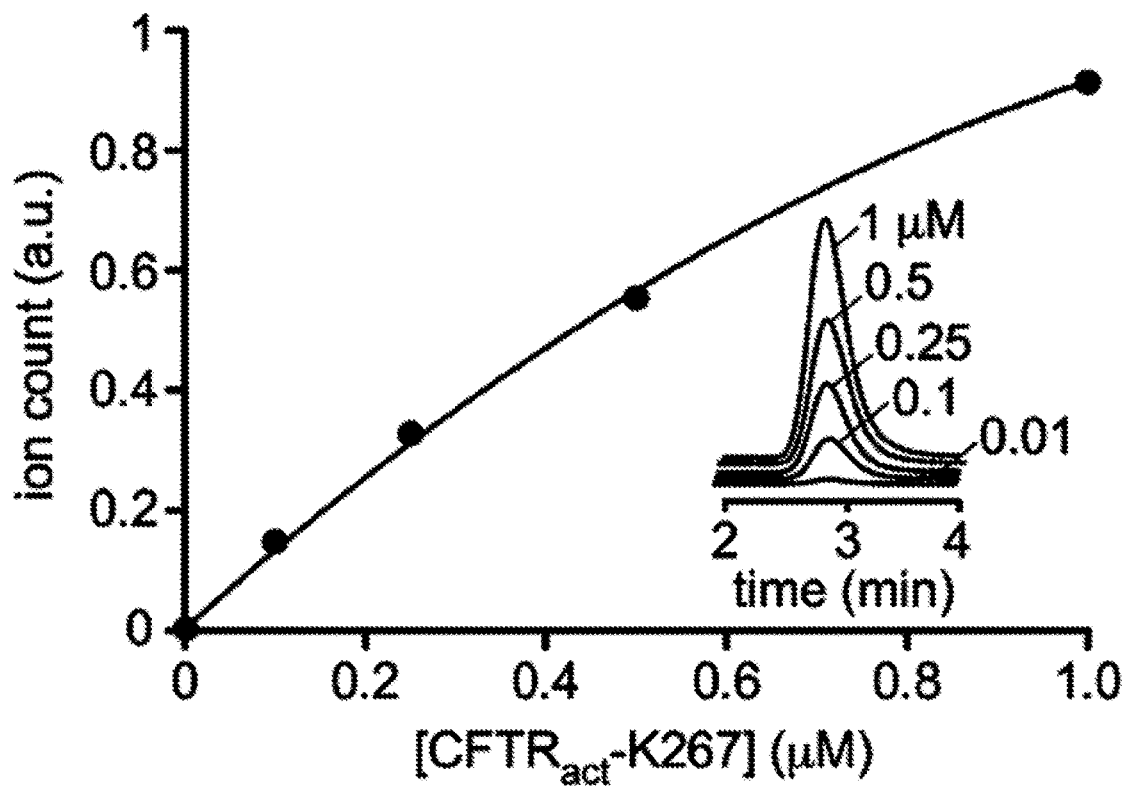
FIGS. 4A-B shows the $CFTR_{act}$-K267 concentration in rabbit tear fluid following instillation of a single 3-nmol dose.
Figure 4B:
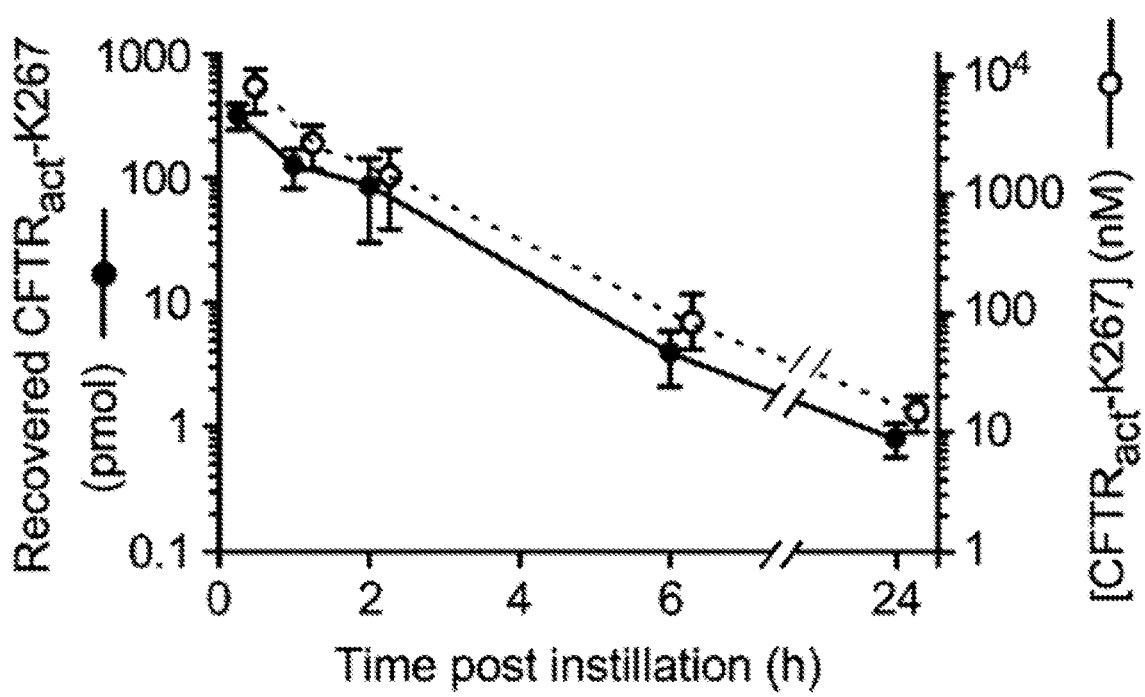

Pharmacokinetics in tear fluid was measured by LC/MS analysis of material recovered in three eye washes done at specified times following a single topical dose of 3 nmol Compound A. FIG. 4A shows original LC/MS data and a standard curve from which the amount of recovered Compound A was deduced. FIG. 4B shows an approximate exponential decline in Compound A recovered from tear fluid (closed circles, left axis). Corresponding compound concentrations in tear fluid (open circles, right ordinate) were estimated using tear volumes deduced from STT measurements in FIG. 2A. These results support the conclusion that Compound A remains at predicted therapeutic concentrations in tear fluid for at least several hours following administration of a 3-nmol dose.

Chronic Administration Studies

Figure 5A:
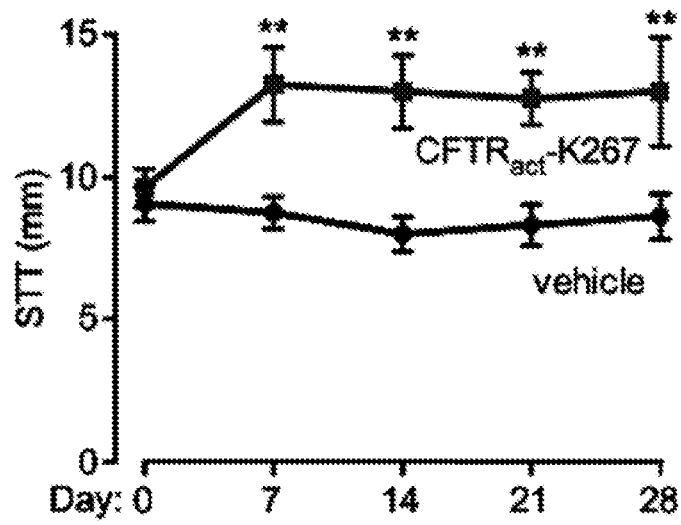
FIGS. 5A-5C show ocular toxicity studies in a chronic $CFTR_{act}$-K267 administration model. Rabbits were treated with 3 nmol $CFTR_{act}$-K267 (or vehicle control) twice daily for 28 days. STT (FIG. 5A), IOP (FIG. 5B) and central corneal thickness (FIG. 5C) is graphed before and weekly following initiation of $CFTR_{act}$-K267 administration (mean±S.E.M., 8 eyes). ** P<0.01, ANOVA, comparing $CFTR_{act}$-K267 vs. vehicle-treated.
Figure 5B:
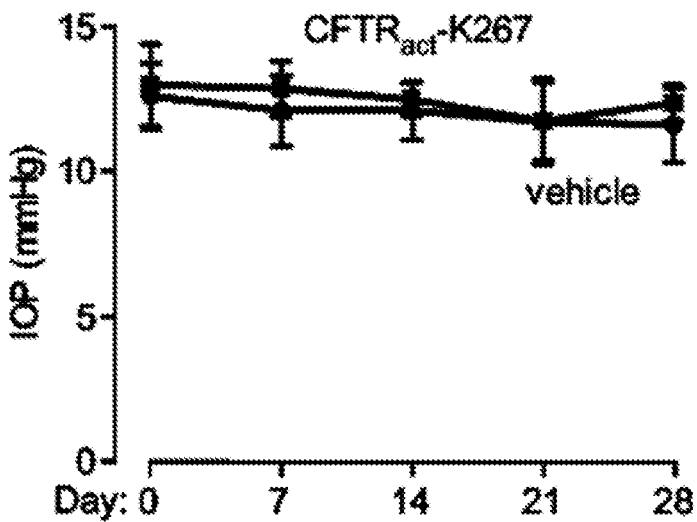
Figure 5C:
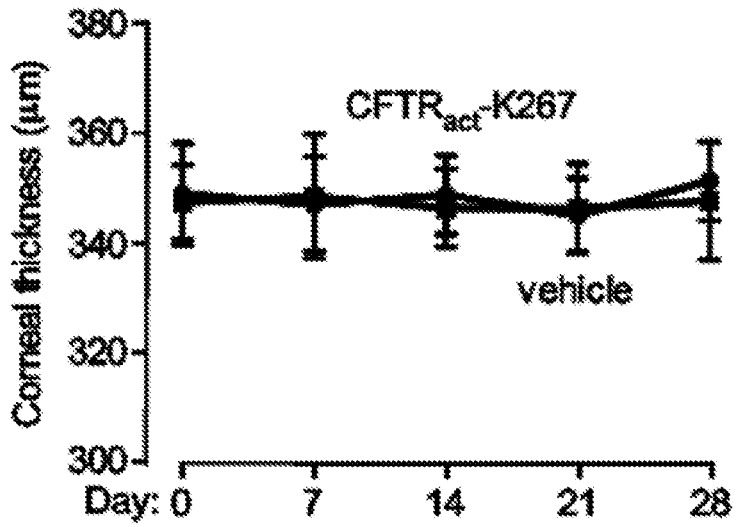
Figure 6A:
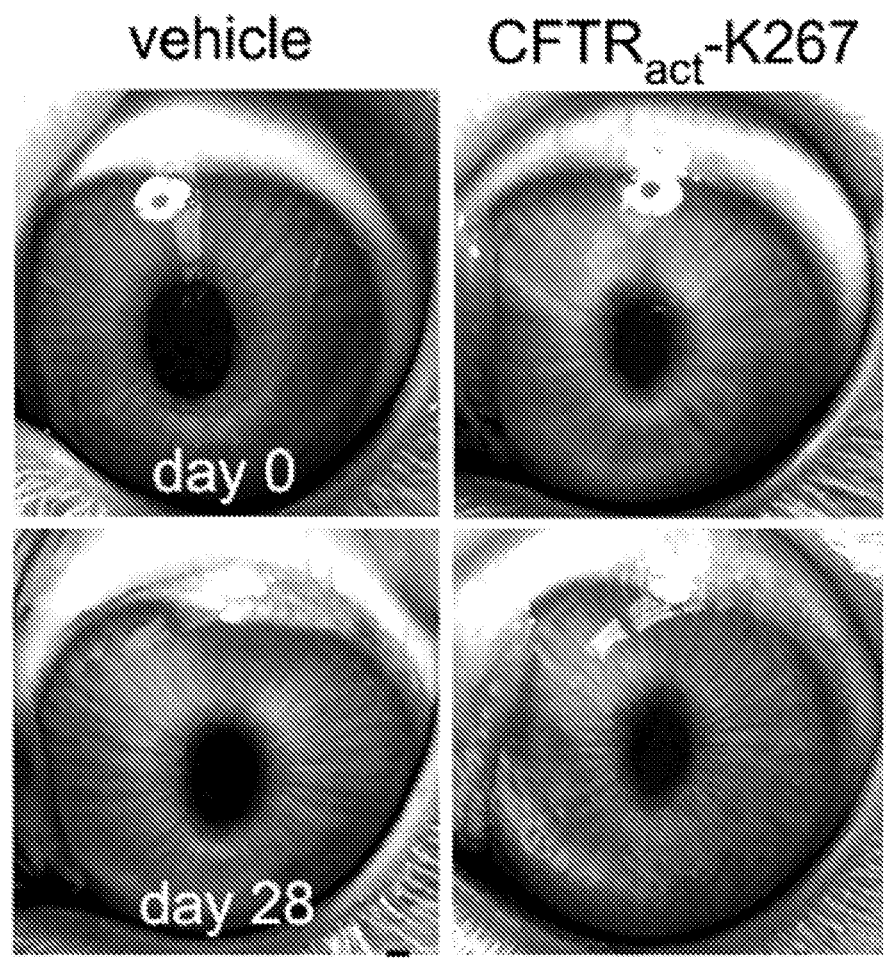
FIGS. 6A-C.
Figure 6B:
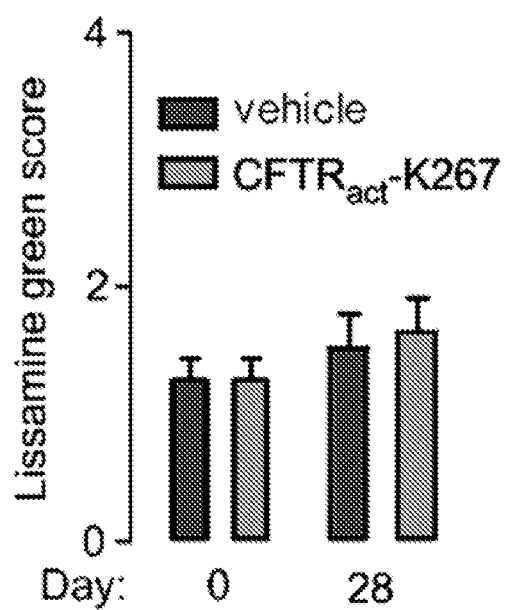
Figure 6C:
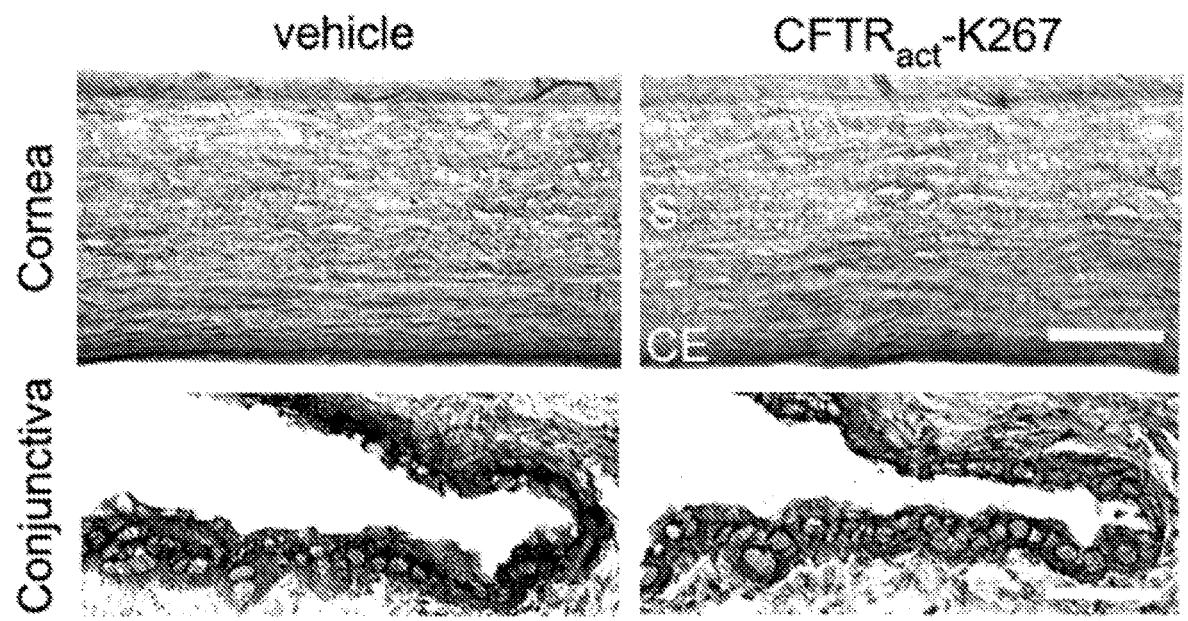

Repeated topical delivery of Compound A (3 nmol, twice-daily for 28 days) augmented tear volume in a sustained fashion without tachyphylaxis (FIG. 5A). No significant differences were found comparing vehicle and Compound A-treated eyes on IOP (FIG. 5B) or central corneal thickness (FIG. 5C). No apparent acute ocular irritation was observed following topical administrations, as evidenced by a lack of excessive blinking or altered behavior. Slit-lamp evaluation showed no evidence of conjunctival hyperemia, anterior chamber inflammation, or lens opacification. Lissamine green staining showed no injury to the ocular surface in vehicle and Compound A-treated eyes (FIG. 6A). Histology showed no pathological changes in cornea or conjunctiva at day 28 (FIG. 6E), or in lens, ciliary body or retina (not shown).

Figure 7A:
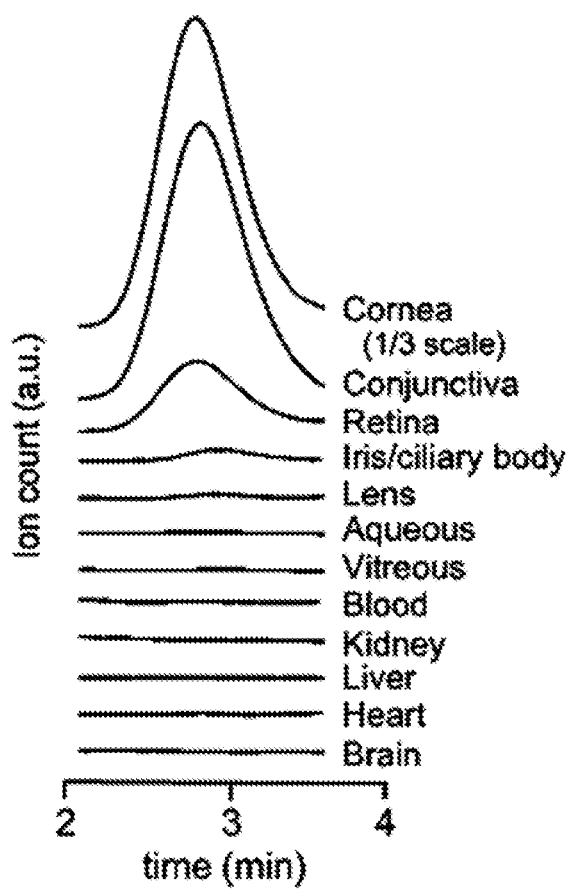
FIGS. 7A-B show tissue levels following chronic $CFTR_{act}$-K267 administration (3 nmol twice-daily for 28 days).
Figure 7B:
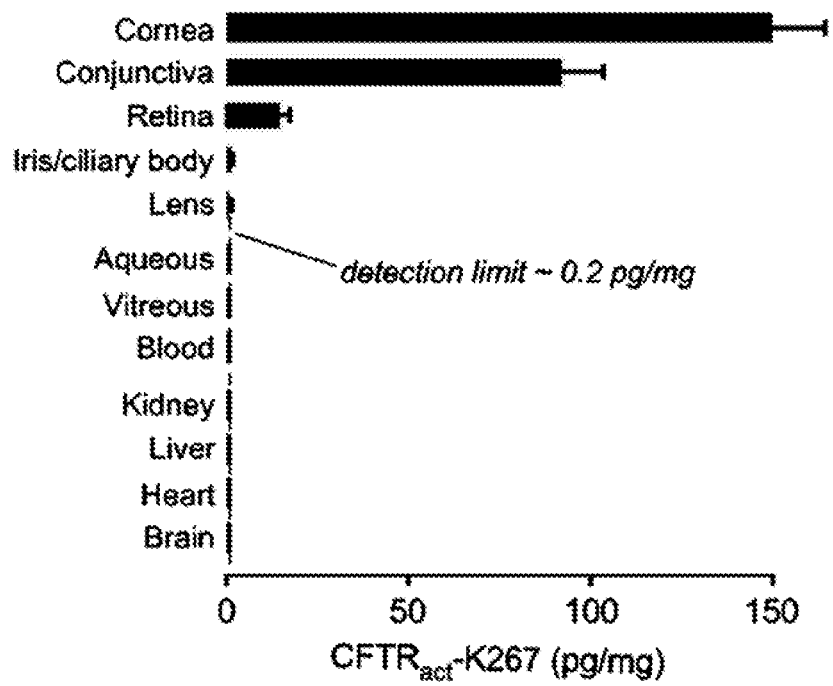

Following the chronic treatment, Compound A was below the limit of detection by LC/MS in blood, heart, brain, liver and kidney (FIGS. 7A and 7B), indicating minimal systemic exposure, as expected, given the rapid predicted hepatic metabolism of Compound A deduced from in vitro microsomal stability measurements. Reference 15. In ocular tissues, the LC/MS analysis showed Compound A in cornea>conjunctiva>>retina, with levels near or below the limit of detection in aqueous and vitreous fluid, lens and iris/ciliary body. The low but measurable level in retina, equivalent to <10 nM Compound A, may result from trans-scleral transport since Compound A was not detected ins vitreous fluid.

Discussion

The functional data showed rapid and prolonged activation of CFTR chloride channels at the rabbit ocular surface following exposure to Compound A. A single topical dose of 3 nmol Compound A produced a substantial and sustained increase in tear secretion for at least 9 hours, which, if translated to human dry eye, could have therapeutic efficacy with once or twice daily dosing. The sustained augmentation in tear production over 9 hours, averaging 5.3 mm by STT, corresponds to a 2.7 µL increase in tear fluid volume using the reported relationship between STT wetting and volume. Reference 18.

Prior studies showed CFTR activation by Compound A with nanomolar potency and without detectable elevation of total cellular cAMP. (Reference 15). The absence of Compound A effect in CFTR-deficient mice supported CFTR-dependent action at the ocular surface. Pharmacodynamic and pharmacokinetic studies here in rabbits showed sustained elevation in tear aqueous production with predicted therapeutic concentrations of Compound A in tear fluid. Chronic administration studies with twice-daily dosing for 28 days revealed Compound A accumulation in ocular tissue, mainly in cornea>conjunctiva>>retina, with levels below the limit of detection in aqueous and vitreous fluid, and in blood and peripheral tissues. Ocular toxicity was not observed as assessed by in vivo examination of the ocular surface, cornea and lens, by measurements of intraocular pressure and corneal thickness, and by ocular histology. Together these finding support the development of Compound A for dry eye disorders.

The potential difference measurement method used here, which was developed initially for studies of ion channels at the mouse ocular surface (References 8, 19), was motivated by nasal potential difference measurements used for decades to study CFTR function in cystic fibrosis. Reference 20. Unlike short-circuit current measurements in isolated cornea or conjunctiva,[16,21] ocular surface PD measurements provide information about CFTR function in its native environment in which ocular surface anatomy and physiology are preserved, which is important because of heterogeneity in transport properties of cornea and conjunctiva (References 19, 22-24), and because of possible changes in basal cyclic nucleotide levels following tissue excision. The PD results here in rabbits showed rapid CFTR activation at the ocular surface with maximal effects within a few minutes after exposure to Compound A. Because of its simplicity and good signal-to-noise, measurements of ocular surface PD may be translatable to humans as a surrogate functional assay of drug candidates targeting ion channels.

The substantial and sustained CFTR activation at the ocular surface produced by Compound A, without tachyphylaxis, is consistent with the known biology of CFTR as studied extensively in the airways and intestine. (References 10, 25, 26). An alternative pro-secretory strategy for dry eye is pharmacological activation of calcium-activated chloride channels, which are thought to be expressed on conjunctival epithelia, mucin cells and lacrimal glands. (References 21, 27). The UTP analog diquafosol, which activates epithelial $P2Y_2$ receptors and downstream calcium signaling, has been approved for dry eye in Japan but did not show efficacy in phase III trials in the United States (Reference 28), perhaps because of the only transient calcium elevation and consequent chloride channel activation produced by $P2Y_2$ agonists. Another pro-secretory strategy for increasing tear fluid is anti-absorptive therapy by inhibition of ENaC sodium channels. In a phase IIIa study the ENaC inhibitor P321 has shown tolerability and safety in patients with mild to moderate dry eye (Reference 29), and a phase II study is in progress. Theoretical modeling supports the efficacy of an anti-absorptive approach to increase tear fluid, albeit with lower efficacy than a pro-secretory approach; modeling also supports the additive action of anti-absorptive and pro-secretory drugs. (Reference 19). We note that pro-secretory or anti-absorption drugs are combinable with anti-inflammatory drugs because they target distinct mechanisms in dry eye pathogenesis. Finally, we note that pro-secretory or anti-absorptive therapy may not correct lipid or mucin deficiency in some cases of dry eye; however, augmentation of aqueous volume is predicted to correct tear fluid hyperosmolality and downstream inflammation even in evaporative dry eye.

Conclusions

In summary, a small molecule CFTR activator with nanomolar potency was effective in producing sustained tear fluid hypersecretion in rabbits following single-dose topical administration. At therapeutic doses administered twice daily for 28 days, compound activity was not diminished, no signs of ocular toxicity were observed, and compound was not detectable outside of the eye. Compound A may thus be a safe and effective therapy of human dry eye disorders, alone or when combined with other dry eye medications.

REFERENCES (1) Alves M, Foseca E C, Alves M F, et al. Dry eye disease treatment: a systematic review of published trials and critical appraisal of therapeutic strategies. Ocul Surf. 2013; 11:181-192. (2) Sheppard J D, Torkildsen G L, Lonsdale J D, et al. Lifitegrast ophthalmic solution 5.0% for treatment of dry eye disease: results of the OPUS-1 phase 3 study. Ophthalmology 2014; 121:475-483. (3) Milner M S, Beckman K A, Luchs J I, et al. Dysfunctional tear syndrome: dry eye disease and associated tear film disorders—new strategies for diagnosis and treatment. Curr Opin Ophthalmol. 2017; 27:3-47. (4) Zaidi T S, Lyczak J, Preston M, Pier G B. Cystic fibrosis transmembrane conductance regulator-mediated corneal epithelial cell ingestion of Pseudomonas aeruginosa is a key component in the pathogenesis of experimental murine keratitis. Infect Immun. 1999; 67:1481-1492. (5) Al-Nakkash L, Reinach P S. Activation of a CFTR-mediated chloride current in a rabbit corneal epithelial cell line. Invest Ophthalmol Vis Sci. 2001; 42:2364-2370. (6) Turner H C, Bernstein A, Candia O A. Presence of CFTR in the conjunctival epithelium. Curr Eye Res. 2002; 24:182-187. (7) Shiue M H, Gukasyan H J, Kim K J, Loo D D, Lee V H. Characterization of cyclic AMP-regulated chloride conductance in the pigmented rabbit conjunctival epithelial cells. Can J Physiol Pharmacol. 2002; 80:533-540. (8) Levin M H, Verkman A S. CFTR-regulated chloride transport at the ocular surface in living mice measured by potential differences. Invest Ophthalmol Vis Sci. 2005; 46:1428-1434. (9) Li J, Allen K T, Sun X C, Cui M, Bonanno J A. Dependence of cAMP meditated increases in Cl$^-$ and HCO$_3^-$ permeability on CFTR in bovine corneal endothelial cells. Exp Eye Res. 2008; 86:684-690. (10) Verkman A S, Galietta U. Chloride channels as drug targets. Nat Rev Drug Discov. 2009; 8:153-171. (11) Cao L, Zhang X D, Liu X, Chen T Y, Zhao M. Chloride channels and transporters in human corneal epithelium. Exp Eye Res. 2010; 90:771-779. (12) Gabriel S E, Brigman K N, Koller B H, Boucher R C, Stutts M J. Cystic fibrosis heterozygote resistance to cholera toxin in the cystic fibrosis mouse model. Science. 1994; 266:107-109. (13) Thiajarajah J R, Donowitz M, Verkman A S. Secretory diarrhea: mechanisms and emerging therapies. Nature Rev Gastroenterol Hepatol. 2015; 12:446-457. (14) Flores A M, Casey S D, Felix C M, Phuan P W, Verkman A S, Levin M H. Small-molecule CFTR activators increase tear secretion and prevent experimental dry eye disease. FASEB J. 2016; 30:1789-1797. (15) Lee S, Phuan P W, Felix C M, Tan J A, Levin M H, Verkman A S. Nanomolar-potency aminophenyl-1,3,5-triazine activators of the cystic fibrosis transmembrane conductance regulator (CFTR) chloride channel for pro-secretory therapy of dry eye diseases. J Med Chem. 2017; 60:1210-1218. (16) Murakami T, Fujihara T, Horibe Y, Nakamura M. Diquafosol elicits increases in net Cl$^-$ transport through P2Y$_2$ receptor stimulation in rabbit conjunctiva. Ophthalmic Res. 2004; 36:89-93. (17) Vijmasi T, Chen F Y T, Chen Y T, Gallup M, McNamara N. Topical administration of interleukin-1 receptor antagonist as a therapy for aqueous-deficient dry eye in autoimmune disease. Mol Vis. 2013; 19:1957-1965. (18) Whittaker A L, Williams D L. Evaluation of lacrimation characteristics in clinically normal New Zealand white rabbits by using the Schirmer tear test I. J Am Assoc Lab Anim Sci. 2015; 54:783-787. (19) Levin M H, Kim J K, Hu J, Verkman A S. Potential difference measurements of ocular surface Na$^+$ absorption analyzed using an electrokinetic model. Invest Ophthalmol Vis Sci. 2006; 47:306-316. (20) Rowe S M, Clancy J P, Wilschanski M. Nasal potential difference measurements to assess CFTR ion channel activity. Meth Mol Biol. 2011; 741:69-86. (21) Yu D, Thelin W R, Rogers T D, et al. Regional differences in rat conjunctival ion transport activities. Am J Physiol Cell Physiol. 2012; 303:C767-C780. (22) Dartt D A. Regulation of mucin and fluid secretion by conjunctival epithelial cells. Prog Retin Eye Res. 2002; 21:555-576. (23) Candia O A. Electrolyte and fluid transport across corneal, conjunctival, and lens epithelia. Exp Eye Res. 2004; 78:527-535. (24) Kompella U B, Kim K J, Lee V H. Active chloride transport in the pigmented rabbit conjunctiva. Curr Eye Res. 1993; 12:1041-1048. (25) Hong J H, Park S, Shcheynikov N, Muallem S. Mechanism and synergism in epithelial fluid and electrolyte secretion. Pflugers Arch. 2014; 466:1487-1499. (26) Saint-Criq V, Gray M A. Role of CFTR in epithelial physiology. Cell Mol Life Sci. 2017; 74:93-115. (27) Nichols K K, Yerxa B, Kellerman D J. Diquafosol tetrasodium: a novel dry eye therapy. Expert Opin Invest Drugs. 2004; 13:47-54. (28) Tauber J, Davitt W F, Bokosky J E, et al. Double-masked, placebo-controlled safety and efficacy trial of diquafosol tetrasodium (INS365) ophthalmic solution for the treatment of dry eye. Cornea. 2004; 23:784-792. (29) Boyer J L, et al. IOVS 2016; 57:ARVO E-Abstract 2875. (30) Bhattacharya D, Ning Y, Zhao F, Stevenson W, Chen R, Zhang J, Wang M. Tear production after bilateral main lacrimal gland resection in rabbits. Invest Ophthalmol Vis Sci. 2015; 56:7774-7783.

P EMBODIMENTS

Embodiment P1. A method of increasing tear production in an eye of a patient in need thereof, the method comprising topically administering to the eye of the patient a pharmaceutical composition comprising about 5 micrograms or more of an active agent to increase tear production; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

Embodiment P2. A method of treating a dry eye disease in a patient in need thereof, the method comprising topically administering to an eye of the patient a pharmaceutical composition comprising about 5 micrograms or more of an active agent to treat the dry eye disease; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

Embodiment P3. The method of embodiment P1 or P2, wherein the pharmaceutical composition comprises from about 5 micrograms to about 100 micrograms of the active agent.

Embodiment P4. The method of embodiment P1 or P2, wherein the pharmaceutical composition comprises from about 5 micrograms to about 50 micrograms of the active agent.

Embodiment P5. The method of embodiment P1 or P2, wherein the pharmaceutical composition comprises from about 5 micrograms to about 35 micrograms of the active agent.

Embodiment P6. The method of embodiment P1 or P2, wherein the pharmaceutical composition comprises about 10 micrograms of the active agent.

Embodiment P7. A method of increasing tear production in an eye of a patient in need thereof, the method comprising topically administering to the eye of the patient a pharmaceutical composition comprising about 2 nanomoles or more of an active agent to increase tear production; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

Embodiment P8. A method of treating a dry eye disease in a patient in need thereof, the method comprising topically administering to an eye of the patient a pharmaceutical composition comprising about 2 nanomoles or more of an active agent to treat the dry eye disease; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

Embodiment P9. The method of embodiment P7 or P8, wherein the pharmaceutical composition comprises from about 2 nanomoles to about 50 nanomoles of the active agent.

Embodiment P10. The method of embodiment P7 or P8, wherein the pharmaceutical composition comprises from about 2 nanomoles to about 25 nanomoles of the active agent.

Embodiment P11. The method of embodiment P7 or P8, wherein the pharmaceutical composition comprises from about 2 nanomoles to about 10 nanomoles of the active agent.

Embodiment P12. The method of embodiment P7 or P8, wherein the pharmaceutical composition comprises about 3 nanomoles of the active agent.

Embodiment P13. A method of increasing tear production in an eye of a patient in need thereof, the method comprising topically administering to the eye of the patient a pharmaceutical composition comprising a therapeutically effective amount of an active agent to increase tear production; wherein the therapeutically effective amount provides a concentration of the active agent in an amount of about 500 nM or more in the tear fluid of the eye about 1 hour to about 12 hours after administration; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

Embodiment P14. A method of treating a dry eye disease in a patient in need thereof, the method comprising topically administering to an eye of the patient a pharmaceutical composition comprising a therapeutically effective amount of an active agent to treat the dry eye disease; wherein the therapeutically effective amount provides a concentration of the active agent in an amount of (i) about 500 nM or more in the tear fluid of the eye about 30 minutes to about 3 hours after administration, or (ii) about 10 nM or more in the tear fluid of the eye about 4 hours to about to about 12 hours after administration; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

Embodiment P15. The method of embodiment P13 or P14, wherein the therapeutically effective amount of the active agent provides a concentration of (i) about 500 nM to about 5,000 nM about 1 hour to about 3 hours after administration, or (ii) about 10 nM to about 2,000 nM about 4 hours to about 8 hours after administration.

Embodiment P16. The method of embodiment P13 or P14, wherein the therapeutically effective amount of the active agent provides a concentration of (i) about 500 nM to about 1,500 nM about 1 hour to about 3 hours after administration, or (ii) about 50 nM to about 500 nM about 5 hours to about 7 hours after administration.

Embodiment P17. The method of embodiment P13 or P14, wherein the therapeutically effective amount of the active agent provides a concentration of (i) about 1000 nM about 2 hours after administration, or (ii) about 100 nM about 6 hours after administration.

Embodiment P18. A method of increasing tear production in an eye of a patient in need thereof, the method comprising topically administering once per day or twice per day to the eye of the patient a pharmaceutical composition comprising of an active agent to increase tear production; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

Embodiment P19. A method of treating a dry eye disease in a patient in need thereof, the method comprising topically administering once per day or twice per day to an eye of the patient a pharmaceutical composition comprising an active agent to treat the dry eye disease; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

Embodiment P20. The method of any one of embodiments P1 to P19, wherein the pharmaceutical composition is a liquid pharmaceutical composition.

Embodiment P21. The method of embodiment P20, wherein the liquid pharmaceutical composition is a solution, a suspension, or an emulsion.

Embodiment P22. The method of embodiment P20, wherein the liquid pharmaceutical composition is an aqueous solution.

Embodiment P23. The method of embodiment P20, wherein the liquid pharmaceutical composition is a suspension; and wherein the active agent is micronized.

Embodiment P24. The method of any one of embodiments P1 to 2P3, wherein the active agent is the compound of Formula (I) or the pharmaceutically acceptable salt thereof.

Embodiment P25. The method of any one of embodiments P1 to P23, wherein the active agent is the compound of Formula (II) or the pharmaceutically acceptable salt thereof.

Embodiment P26. The method of any one of embodiments P1 to P23, wherein the active agent is the compound of Formula (III) or the pharmaceutically acceptable salt thereof.

Embodiment P27. The method of any one of embodiments P1 to P23, wherein the active agent is the compound of Formula (IV) or the pharmaceutically acceptable salt thereof Embodiment P28. The method of any one of embodiments P1 to P23, wherein the active agent is Compound A or the pharmaceutically acceptable salt thereof.

Embodiment P29. The method of any one of embodiments P1 to P23, wherein the active agent is Compound B or the pharmaceutically acceptable salt thereof.

Embodiment P30. The method of any one of embodiments P1 to P23, wherein the active agent is Compound C or the pharmaceutically acceptable salt thereof Embodiment P31. The method of any one of embodiments P1 to P23, wherein the active agent is Compound D or the pharmaceutically acceptable salt thereof.

Embodiment P32. The method of any one of embodiments P1 to P23, wherein the active agent is Compound E or the pharmaceutically acceptable salt thereof.

Embodiment P33. The method of any one of embodiments P1 to P32 wherein the composition further comprises a pharmaceutically acceptable excipient.

Embodiment P34. The method of embodiment P33, wherein the pharmaceutically acceptable excipient is a stabilizer, a co-solvent, or a combination thereof.

Embodiment P35. The method of any one of embodiments P1 to P34, comprising topically administering the pharmaceutical composition to the conjunctiva of the eye.

Embodiment P36. The method of any one of embodiments P1 to P34 comprising topically administering the pharmaceutical composition to the conjunctival sac of the eye.

Embodiment P37. The method of any one of embodiments P1 to P36, wherein the pharmaceutical composition is administered once per day.

Embodiment P38. The method of any one of embodiments P1 to P36, wherein the pharmaceutical composition is administered twice per day.

Embodiment P39. The method of any one of embodiments P1 to P38, wherein the composition is administered for about 14 days.

Embodiment P40. The method of any one of embodiments P1 to P38, wherein the composition is administered for about one month.

Embodiment P41. The method of any one of embodiments P1 to P40, further comprising administering a epithelial sodium channel inhibitor, a lymphocyte function-associated antigen-1 antagonist, an anti-inflammatory agent, a cholinergic agonist, a steroid, an antibiotic, or a combination of two or more thereof.

Embodiment P42. The method of embodiment 41, wherein the epithelial sodium channel inhibitor is amiloride; wherein the lymphocyte function-associated antigen-1 antagonist is lifitegrast; wherein the anti-inflammatory agent is cyclosporine; wherein the cholinergic agonist is pilocarpine or cevimeline; and wherein the steroid is a corticosteroid.

Embodiment P43. The method of any one of embodiments P1 to P42, wherein the patient is a human.

Embodiment P44. The method of any one of embodiments P1 to P43, wherein the patient has an open-circuit transepithelial potential difference, in response to contact with different solutions, that is lower than that of a control.

Embodiment P45. The method of any one of embodiments P1 to P44, further comprising testing the change in the open-circuit transepithelial potential difference, in response to contact with different solutions, at the surface of the eye of the patient, and comparing the result to a control.

Embodiment P46. A topical pharmaceutical composition comprising about 5 micrograms or more of an active agent and a pharmaceutically acceptable carrier; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

Embodiment P47. The composition of embodiment P46, comprising from about 5 micrograms to about 1 gram of the active agent.

Embodiment P48. The composition of embodiment P46, comprising from about 5 micrograms to about 1 milligram of the active agent.

Embodiment P49. The composition of embodiment P46, comprising from about 5 micrograms to about 500 micrograms.

Embodiment P50. The composition of embodiment P46, comprising from about 5 micrograms to about 35 micrograms of the active agent.

Embodiment P51. The composition of embodiment P47, comprising about 10 micrograms.

Embodiment P52. A topical pharmaceutical composition comprising from about 1 nanomole to about 25 nmoles per 0.5 mL of an active agent and a pharmaceutically acceptable excipient; wherein the active agent is a compound of Formula (I), a compound of Formula (II), a compound of Formula (III), a compound of Formula (IV), Compound A, Compound B, Compound C, Compound D, Compound E, or a pharmaceutically acceptable salt of any of the foregoing.

Embodiment P53. The composition of embodiment P52, comprising from about 1 nanomole to about 15 nmoles per 0.5 mL of the active agent.

Embodiment P54. The composition of embodiment P52, comprising from about 2 nanomoles to about 10 nmoles per 0.5 mL of the active agent.

Embodiment P55. The composition of embodiment P52, comprising about 3 nanomoles per 0.5 mL of the active agent.

Embodiment P56. The composition of any one of embodiments P46 to P55, wherein the topical pharmaceutical composition is a liquid pharmaceutical composition.

Embodiment P57. The composition of embodiment P56, wherein the liquid pharmaceutical composition is a solution, a suspension, or an emulsion.

Embodiment P58. The composition of embodiment P56, wherein the liquid pharmaceutical composition is an aqueous solution.

Embodiment P59. The composition of embodiment P56, wherein the liquid pharmaceutical composition is a suspension; and wherein the compound is micronized.

Embodiment P60. The composition of any one of embodiments P46 to P59, wherein the composition further comprises a pharmaceutically acceptable excipient.

Embodiment P61. The composition of embodiment P60, wherein the pharmaceutically acceptable excipient is a stabilizer, a co-solvent, or a combination thereof.

Embodiment P62. The composition of any one of embodiments P46 to P61, wherein the active agent is the compound of Formula (I) or the pharmaceutically acceptable salt thereof.

Embodiment P63. The composition of any one of embodiments P46 to P61, wherein the active agent is the compound of Formula (II) or the pharmaceutically acceptable salt thereof.

Embodiment P64. The composition of any one of embodiments P46 to P61, wherein the active agent is the compound of Formula (III) or the pharmaceutically acceptable salt thereof.

Embodiment P65. The composition of any one of embodiments P46 to P61, wherein the pharmaceutical composition comprises the compound of Formula (IV) or the pharmaceutically acceptable salt thereof.

Embodiment P66. The composition of any one of embodiments P46 to P61, wherein the active agent is Compound A or the pharmaceutically acceptable salt thereof.

Embodiment P67. The composition of any one of embodiments P46 to P61, wherein the active agent is Compound B or the pharmaceutically acceptable salt thereof.

Embodiment P68. The composition of any one of embodiments P46 to P61, wherein the active agent is Compound C or the pharmaceutically acceptable salt thereof.

Embodiment P69. The composition of any one of embodiments P46 to P61, wherein the active agent is Compound D or the pharmaceutically acceptable salt thereof.

Embodiment P70. The composition of any one of embodiments P46 to P61, wherein the active agent is Compound E or the pharmaceutically acceptable salt thereof.

Embodiment P71. An eye dropper for delivering a drop of a topical pharmaceutical composition to the eye of a patient; wherein the eye dropper comprises the topical composition of any one of embodiments P46 to P70.

Embodiment P72. The eye dropper of embodiment P71 having a volume sufficient to house 1 to 25 drops of the composition.

Embodiment P73. The eye dropper of embodiment P71 having a volume sufficient to house 1 to 15 drops of the composition.

Embodiment P74. The eye dropper of embodiment P1 having a volume sufficient to house 1 to 10 drops of the composition.

Embodiment P75. A kit comprising the eye dropper of any one of embodiments P71 to P74 and instructions for use.

Embodiment P76. The kit of embodiment P75, comprising seven eye droppers, fourteen eye droppers, twenty-eight eye droppers, or fifty-six eye droppers.

Embodiment P77. A kit comprising an eye dropper, a container which comprises the topical pharmaceutical composition of any one of embodiments P46 to P70, and instructions for use.

Embodiment P78. The kit of embodiment P77, comprising one eye dropper and one container; wherein the container comprises one dose of the composition.

Embodiment P79. The kit of embodiment P77, comprising two eye droppers and one container; wherein the container comprises two doses of the composition.

Embodiment P80. The kit of embodiment P77, comprising two eye droppers and two containers; wherein each container comprises one dose of the composition.

Embodiment P81. The kit of embodiment P77, comprising seven eye droppers and seven containers; wherein each container comprises one dose of the composition.

Embodiment P82. The kit of embodiment P77, comprising fourteen eye droppers and seven containers; wherein each container comprises two doses of the composition.

Embodiment P83. The kit of embodiment P77, comprising fourteen eye droppers and fourteen containers; wherein each container comprises one dose of the composition.

Embodiment P84. A method of identifying a patient for treatment with a modulator of ocular surface membrane transport, the method comprising the steps of:
(i) measuring a change in an open-circuit transepithelial potential difference, in response to contact with different solutions, at an ocular surface of the patient;
(ii) comparing the change in the open-circuit transepithelial potential difference, in response to contact with different solutions, to a control; and
(iii) identifying that the patient should be treated with the modulator of ocular surface membrane transport if the change in the open-circuit transepithelial potential difference is lower than that of the control.

Embodiment P85. The method of embodiment P84, wherein the ocular surface membrane transport is an ion transporter or a biomolecule transporter.

Embodiment P86. The method of embodiment P85, wherein the ion transporter is a chloride transporter, a potassium transporter, or a bicarbonate transporter; and wherein the biomolecule transporter is a glucose transporter or a urea transporter.

Embodiment P87. The method of embodiment P85, further comprising treating the patient with a therapeutically effective amount of the modulator of ocular surface membrane transport.

Embodiment P88. The method of embodiment P85, wherein the modulator of ocular surface membrane transport is a CFTR agonist, a calcium-activated chloride channel activator, or an epithelial sodium channel (ENaC) inhibitor.

Embodiment P89. The method of embodiment P85, wherein the modulator of ocular surface membrane transport is a pharmaceutical composition of any one of claims 46 to 70.

Embodiment P90. A method of identifying a patient for treatment with a modulator of intracellular signaling, the method comprising the steps of:
(i) measuring a change in an open-circuit transepithelial potential difference, in response to contact with different solutions, at an ocular surface of the patient;
(ii) comparing the change in the open-circuit transepithelial potential difference, in response to contact with different solutions, to a control; and
(iii) identifying that the patient should be treated with the modulator of intracellular signaling if the change in the open-circuit transepithelial potential difference is lower than that of the control.

Embodiment P91. The method of embodiment P90, wherein the modulator of intracellular signaling is cAMP, cGMP, or calcium signaling; wherein the modulator directly or indirectly modulates intracellular signaling.

Embodiment P92. The method of embodiment P90, further comprising treating the patient by administering a therapeutically effective amount of the pharmaceutical composition of any one of claims 46 to 70.

Embodiment P93. The method of any one of embodiments P84 to P92, wherein the ocular surface is the cornea or the conjunctiva.

EMBODIMENTS

Embodiment 1. A method of treating a patient in need of increased tear production comprising topically administering to an eye of the patient at least about 5 micrograms of at least one compound selected from a group consisting of:
(a) a compound of Formula (I), or a pharmaceutically acceptable salt thereof:

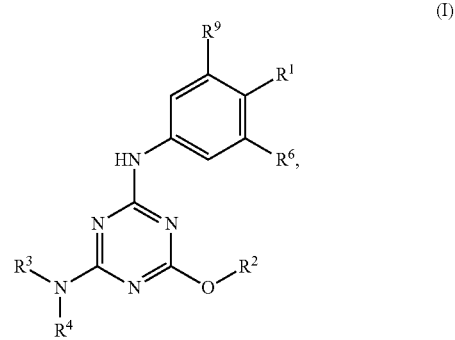

wherein:
$R^1$ is:
(i) hydrogen;
(ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; or
(iii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;

$R^2$ is a $C_2$-$C_4$ haloalkyl;

$R^3$ is hydrogen or a $C_1$-$C_3$ alkyl;

$R^4$ is hydrogen or a $C_1$-$C_3$ alkyl;

$R^6$ is:

(i) hydrogen; or (ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; and $R^9$ is:

(i) hydrogen; or (ii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;

(b) a compound of Formula (II), or a pharmaceutically acceptable salt thereof:

(II)

[Chemical structure of Formula (II)]

wherein:

$R^1$ and $R^6$ are joined to form, together with the atoms to which they are attached, a $C_9$ heteroaryl, wherein $R^1$ and $R^6$ are —X1-CH—X2-, wherein X1 and X2 are each independently —O—, —N═, or —S—;

$R^1$ and $R^9$ are joined to form, together with the atoms to which they are attached, a $C_9$ heteroaryl, wherein $R^1$ and $R^9$ are —X1-CH—X2-, wherein X1 and X2 are each independently —O—, —N═, or —S—;

$R^2$ is —CH(CF$_3$)$_2$ or —CH$_2$CF$_2$CF$_2$H;

$R^3$ is hydrogen, methyl, or ethyl;

$R^4$ is hydrogen, methyl, or ethyl;

$R^6$ is:

(i) hydrogen; or (ii) $R^1$ and $R^6$ are joined to form, together with the atoms to which they are attached, a $C_9$ heteroaryl wherein $R^1$ and $R^6$ are —X—CH—X2- and X1 is —O— or —N═ and X2 is ═N— or —O—; and $R^9$ is:

(i) hydrogen; or (ii) $R^1$ and $R^9$ are joined to form, together with the atoms to which they are attached, a $C_9$ heteroaryl wherein $R^1$ and $R^9$ are —X—CH—X2- and X1 is —O— or —N═ and X2 is ═N— or —O—;

(c) a compound of Formula (III), or a pharmaceutically acceptable salt thereof:

(III)

[Chemical structure of Formula (III)]

wherein:

$R^2$ is —CH(CF$_3$)$_2$ or —CH$_2$CF$_2$CF$_2$H;

$R^3$ is hydrogen, methyl, or ethyl; and $R^4$ is hydrogen, methyl, or ethyl;

(d) a compound of Formula (IV), or a pharmaceutically acceptable salt thereof:

(IV)

[Chemical structure of Formula (IV)]

wherein:

$R^2$ is —CH(CF$_3$)$_2$ or —CH$_2$CF$_2$CF$_2$H; and $R^4$ is hydrogen, methyl, or ethyl;

(e) compound A having the formula:

A

[Chemical structure of compound A]

or a pharmaceutically acceptable salt thereof, (f) compound B having the formula:

B

[Chemical structure of compound B]

or a pharmaceutically acceptable salt thereof;

(g) compound C having the formula:

C

<chemical structure: Compound C - triazine with N(ethyl)2, O-CH(CF3)(C(CF3)), and NH-phenyl substituents> or a pharmaceutically acceptable salt thereof;

(h) compound D having the formula:

D

<chemical structure: Compound D - triazine with N(ethyl)2, O-CH(CF3)2, and NH-benzoxazole substituents> or a pharmaceutically acceptable salt thereof; and (i) compound E having the formula:

E

<chemical structure: Compound E - triazine with N(ethyl)2, O-CH(CF3)2, and NH-benzothiazole substituents> or a pharmaceutically acceptable salt thereof.

Embodiment 2. A method of treating a dry eye disease in a patient comprising topically administering to an eye of the patient at least about 5 micrograms of at least one active agent selected from a group consisting of:

(a) a compound of Formula (I), or a pharmaceutically acceptable salt thereof:

(I)

<chemical structure of Formula (I)> wherein:
$R^1$ is:
(i) hydrogen;
(ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; or
(iii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;
$R^2$ is a $C_2$-$C_4$ haloalkyl;
$R^3$ is hydrogen or a $C_1$-$C_3$ alkyl;
$R^4$ is hydrogen or a $C_1$-$C_3$ alkyl;
$R^6$ is:
(i) hydrogen; or
(ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; and
$R^9$ is:
(i) hydrogen; or
(ii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;

(b) a compound of Formula (II), or a pharmaceutically acceptable salt thereof:

(II)

<chemical structure of Formula (II)> wherein:
$R^1$ and $R^6$ are joined to form, together with the atoms to which they are attached, a $C_9$ heteroaryl, wherein $R^1$ and R⁶ are —X1-CH—X2-, wherein X1 and X2 are each independently —O—, —N═, or —S—;

R¹ and R⁹ are joined to form, together with the atoms to which they are attached, a C₉ heteroaryl, wherein R¹ and R⁹ are —X1-CH—X2-, wherein X1 and X2 are each independently —O—, —N═, or —S—;

R² is —CH(CF₃)₂ or —CH₂CF₂CF₂H;

R³ is hydrogen, methyl, or ethyl;

R⁴ is hydrogen, methyl, or ethyl;

R⁶ is:

(i) hydrogen; or (ii) R¹ and R⁶ are joined to form, together with the atoms to which they are attached, a C₉ heteroaryl wherein R¹ and R⁶ are —X1-CH—X2- and X1 is —O— or —N═ and X2 is ═N— or —O—; and R⁹ is:

(i) hydrogen; or (ii) R¹ and R⁹ are joined to form, together with the atoms to which they are attached, a C₉ heteroaryl wherein R¹ and R⁹ are —X1-CH—X2- and X1 is —O— or —N═ and X2 is ═N— or —O—:

(c) a compound of Formula (III), or a pharmaceutically acceptable salt thereof:

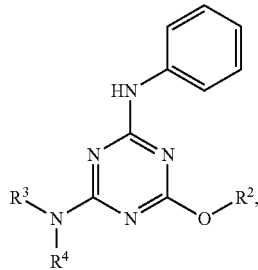

(III)

wherein:

R² is —CH(CF₃)₂ or —CH₂CF₂CF₂H;

R³ is hydrogen, methyl, or ethyl; and

R⁴ is hydrogen, methyl, or ethyl;

(d) a compound of Formula (IV), or a pharmaceutically acceptable salt thereof:

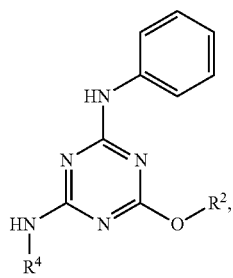

(IV)

wherein:

R² is —CH(CF₃)₂ or —CH₂CF₂CF₂H; and

R⁴ is hydrogen, methyl, or ethyl;

(e) compound A having the formula:

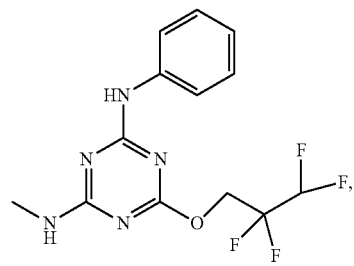

A or a pharmaceutically acceptable salt thereof;

(f) compound B having the formula:

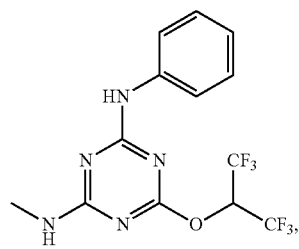

B or a pharmaceutically acceptable salt thereof;

(g) compound C having the formula:

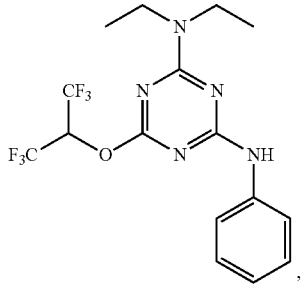

C or a pharmaceutically acceptable salt thereof;

(h) compound D having the formula:

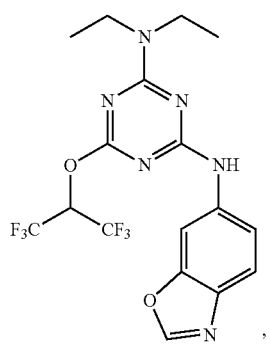

D or a pharmaceutically acceptable salt thereof, and
(i) compound E having the formula:

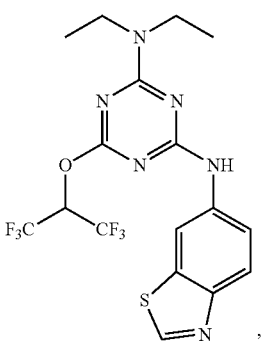

or a pharmaceutically acceptable salt thereof.

Embodiment 3. The method of embodiment 1 or 2, wherein the method comprises administering from about 5 micrograms to about 100 micrograms of the active agent.

Embodiment 4. The method of embodiment 1 or 2, wherein the method comprises administering from about 5 micrograms to about 50 micrograms of the active agent.

Embodiment 5. The method of embodiment 1 or 2, wherein the method comprises administering from about 5 micrograms to about 35 micrograms of the active agent.

Embodiment 6. The method of embodiment 1 or 2, wherein the method comprises administering about 10 micrograms of the active agent.

Embodiment 7. A method of treating a patient in need of increased tear production comprising: topically administering to an eye of the patient at least about 2 nanomoles of at least one active agent selected from a group consisting of:

(a) a compound of Formula (I), or a pharmaceutically acceptable salt thereof:

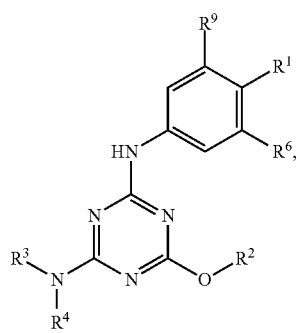

wherein:
$R^1$ is:
(i) hydrogen;
(ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; or
(iii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;

$R^2$ is a $C_2$-$C_4$ haloalkyl;
$R^3$ is hydrogen or a $C_1$-$C_3$ alkyl;
$R^4$ is hydrogen or a $C_1$-$C_3$ alkyl;
$R^6$ is:
(i) hydrogen; or
(ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; and $R^9$ is:
(i) hydrogen; or
(ii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;

(b) a compound of Formula (II), or a pharmaceutically acceptable salt thereof:

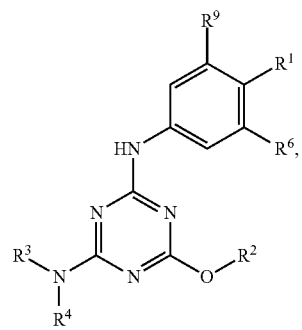

wherein:
$R^1$ and $R^6$ are joined to form, together with the atoms to which they are attached, a $C_9$ heteroaryl, wherein $R^1$ and $R^6$ are —X1-CH—X2-, wherein X1 and X2 are each independently —O—, —N=, or —S—;

$R^1$ and $R^9$ are joined to form, together with the atoms to which they are attached, a $C_9$ heteroaryl, wherein $R^1$ and $R^9$ are —X1-CH—X2-, wherein X1 and X2 are each independently —O—, —N=, or —S—;

$R^2$ is —CH(CF$_3$)$_2$ or —CH$_2$CF$_2$CF$_2$H;
$R^3$ is hydrogen, methyl, or ethyl;
$R^4$ is hydrogen, methyl, or ethyl;
$R^6$ is:
(i) hydrogen; or
(ii) $R^1$ and $R^6$ are joined to form, together with the atoms to which they are attached, a $C_9$ heteroaryl wherein $R^1$ and $R^6$ are —X—CH—X2- and X1 is —O— or —N= and X2 is =N— or —O—; and $R^9$ is:
(i) hydrogen; or
(ii) $R^1$ and $R^9$ are joined to form, together with the atoms to which they are attached, a $C_9$ heteroaryl wherein $R^1$ and $R^9$ are —X—CH—X2- and X1 is —O— or —N= and X2 is =N— or —O—;

(c) a compound of Formula (III), or a pharmaceutically acceptable salt thereof:

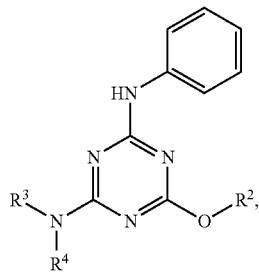

(III)

wherein:
R² is —CH(CF₃)₂ or —CH₂CF₂CF₂H;
R³ is hydrogen, methyl, or ethyl; and
R⁴ is hydrogen, methyl, or ethyl;

(d) a compound of Formula (IV), or a pharmaceutically acceptable salt thereof:

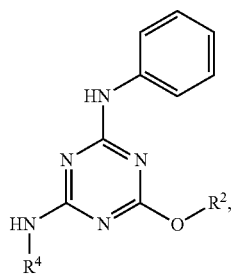

(IV)

wherein:
R² is —CH(CF₃)₂ or —CH₂CF₂CF₂H; and
R⁴ is hydrogen, methyl, or ethyl;

(e) compound A having the formula:

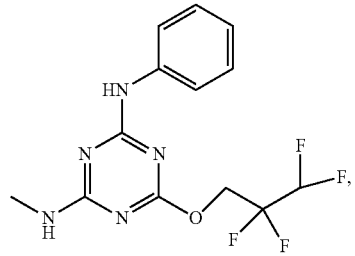

A or a pharmaceutically acceptable salt thereof, (f) compound B having the formula:

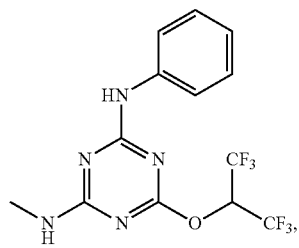

B or a pharmaceutically acceptable salt thereof;

(g) compound C having the formula:

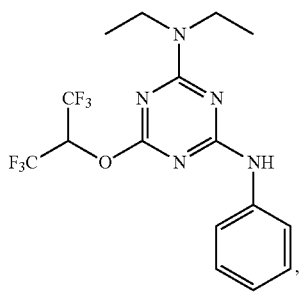

C or a pharmaceutically acceptable salt thereof;

(h) compound D having the formula:

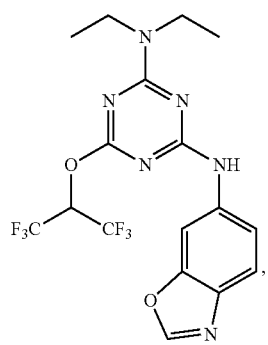

D or a pharmaceutically acceptable salt thereof, and
(i) compound E having the formula:

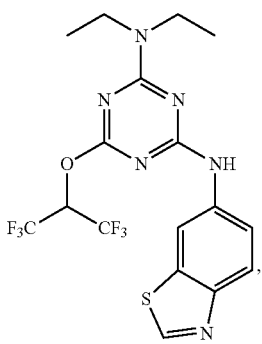

or a pharmaceutically acceptable salt thereof.

Embodiment 8. A method of treating a patient with dry eye disease comprising: topically administering to an eye of the patient at least about 2 nanomoles of at least one active agent selected from a group consisting of:
(a) a compound of Formula (I), or a pharmaceutically acceptable salt thereof:

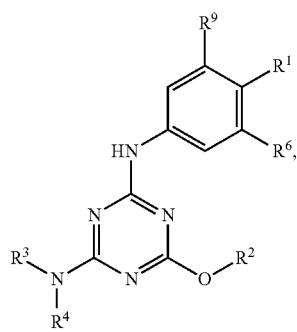

wherein:
$R^1$ is:
(i) hydrogen;
(ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; or
(iii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;
$R^2$ is a $C_2$-$C_4$ haloalkyl;
$R^3$ is hydrogen or a $C_1$-$C_3$ alkyl;
$R^4$ is hydrogen or a $C_1$-$C_3$ alkyl;
$R^6$ is:
(i) hydrogen; or
(ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; and
$R^9$ is:
(i) hydrogen; or
(ii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;
(b) a compound of Formula (II), or a pharmaceutically acceptable salt thereof:

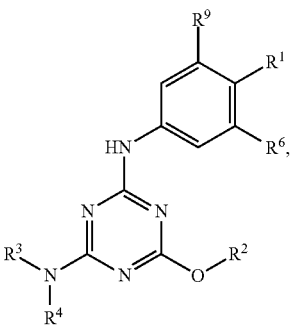

wherein:
$R^1$ and $R^6$ are joined to form, together with the atoms to which they are attached, a $C_9$ heteroaryl, wherein $R^1$ and $R^6$ are —X1-CH—X2-, wherein X1 and X2 are each independently —O—, —N═, or —S—;
$R^1$ and $R^9$ are joined to form, together with the atoms to which they are attached, a $C_9$ heteroaryl, wherein $R^1$ and $R^9$ are —X1-CH—X2-, wherein X1 and X2 are each independently —O—, —N═, or —S—;
$R^2$ is —CH(CF$_3$)$_2$ or —CH$_2$CF$_2$CF$_2$H;
$R^3$ is hydrogen, methyl, or ethyl;
$R^4$ is hydrogen, methyl, or ethyl;
$R^6$ is:
(i) hydrogen; or
(ii) $R^1$ and $R^6$ are joined to form, together with the atoms to which they are attached, a $C_9$ heteroaryl wherein $R^1$ and $R^6$ are —X1-CH—X2- and X1 is —O— or —N═ and X2 is ═N— or —O—; and
$R^9$ is:
(i) hydrogen; or
(ii) $R^1$ and $R^9$ are joined to form, together with the atoms to which they are attached, a $C_9$ heteroaryl wherein $R^1$ and $R^9$ are —X1-CH—X2- and X1 is —O— or —N═ and X2 is ═N— or —O—:
(c) a compound of Formula (III), or a pharmaceutically acceptable salt thereof:

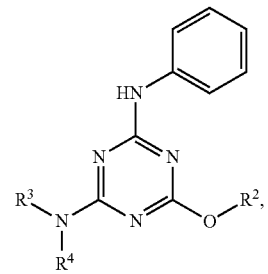

wherein:
$R^2$ is —CH(CF$_3$)$_2$ or —CH$_2$CF$_2$CF$_2$H;
$R^3$ is hydrogen, methyl, or ethyl; and
$R^4$ is hydrogen, methyl, or ethyl;
(d) a compound of Formula (IV), or a pharmaceutically acceptable salt thereof:

(IV)

[Structure: triazine with HN-phenyl, HN-R⁴, O-R²]

wherein:

R² is —CH(CF₃)₂ or —CH₂CF₂CF₂H; and
R⁴ is hydrogen, methyl, or ethyl;

(e) compound A having the formula:

[Structure of compound A: triazine with HN-phenyl, NH-CH₃, O-CH₂CF₂CF₂H]

A or a pharmaceutically acceptable salt thereof;

(f) compound B having the formula:

[Structure of compound B: triazine with HN-phenyl, NH-CH₃, O-CH(CF₃)₂]

B or a pharmaceutically acceptable salt thereof;

(g) compound C having the formula:

[Structure of compound C: triazine with N(Et)₂, NH-phenyl, O-CH(CF₃)₂]

C or a pharmaceutically acceptable salt thereof;

(h) compound D having the formula:

[Structure of compound D: triazine with N(Et)₂, NH-benzoxazolyl, O-CH(CF₃)₂]

D or a pharmaceutically acceptable salt thereof, a (i) compound E having the formula:

[Structure of compound E: triazine with N(Et)₂, NH-benzothiazolyl, O-CH(CF₃)₂]

E or a pharmaceutically acceptable salt thereof.

Embodiment 9. The method of embodiment 7 or 8, wherein the method comprises administering from about 2 nanomoles to about 50 nanomoles of the active agent.

Embodiment 10. The method of embodiment 7 or 8, wherein the method comprises administering from about 2 nanomoles to about 25 nanomoles of the active agent.

Embodiment 11. The method of embodiment 7 or 8, wherein the method comprises administering from about 2 nanomoles to about 10 nanomoles of the active agent.

Embodiment 12. The method of embodiment 7 or 8, wherein the method comprises administering about 3 nanomoles of the active agent.

Embodiment 13. A method of treating a patient in need of increased tear production comprising: topically administering to an eye of the patient an amount of an active agent producing a concentration of about 500 nM or more in the tear fluid of the eye about 1 hour to about 12 hours after administration; wherein the active agent is selected from a group consisting of:

(a) a compound of Formula (I), or a pharmaceutically acceptable salt thereof:

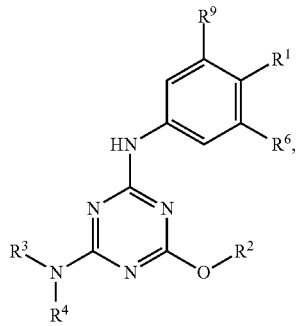

wherein:

$R^1$ is:

(i) hydrogen;

(ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; or (iii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;

$R^2$ is a $C_2$-$C_4$ haloalkyl;

$R^3$ is hydrogen or a $C_1$-$C_3$ alkyl;

$R^4$ is hydrogen or a $C_1$-$C_3$ alkyl;

$R^6$ is:

(i) hydrogen; or (ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; and $R^9$ is:

(i) hydrogen; or (ii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;

(b) a compound of Formula (II), or a pharmaceutically acceptable salt thereof:

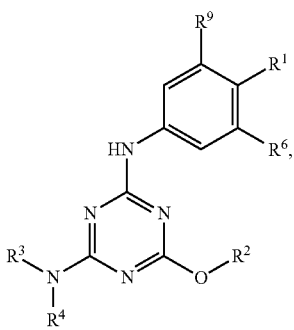

wherein:

$R^1$ and $R^6$ are joined to form, together with the atoms to which they are attached, a $C_9$ heteroaryl, wherein $R^1$ and $R^6$ are —X1-CH—X2-, wherein X1 and X2 are each independently —O—, —N═, or —S—;

$R^1$ and $R^9$ are joined to form, together with the atoms to which they are attached, a $C_9$ heteroaryl, wherein $R^1$ and $R^9$ are —X1-CH—X2-, wherein X1 and X2 are each independently —O—, —N═, or —S—;

$R^2$ is —CH(CF$_3$)$_2$ or —CH$_2$CF$_2$CF$_2$H;

$R^3$ is hydrogen, methyl, or ethyl;

$R^4$ is hydrogen, methyl, or ethyl;

$R^6$ is:

(i) hydrogen; or (ii) $R^1$ and $R^6$ are joined to form, together with the atoms to which they are attached, a $C_9$ heteroaryl wherein $R^1$ and $R^6$ are —X—CH—X2- and X1 is —O— or —N═ and X2 is ═N— or —O—; and $R^9$ is:

(i) hydrogen; or (ii) $R^1$ and $R^9$ are joined to form, together with the atoms to which they are attached, a $C_9$ heteroaryl wherein $R^1$ and $R^9$ are —X—CH—X2- and X1 is —O— or —N═ and X2 is ═N— or —O—:

(c) a compound of Formula (III), or a pharmaceutically acceptable salt thereof:

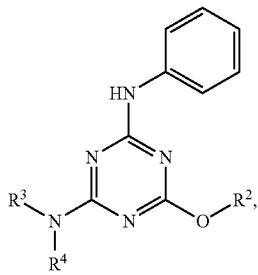

wherein:

$R^2$ is —CH(CF$_3$)$_2$ or —CH$_2$CF$_2$CF$_2$H;

$R^3$ is hydrogen, methyl, or ethyl; and $R^4$ is hydrogen, methyl, or ethyl;

(d) a compound of Formula (IV), or a pharmaceutically acceptable salt thereof:

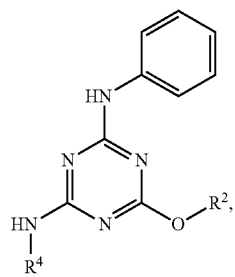

wherein:

R² is —CH(CF₃)₂ or —CH₂CF₂CF₂H; and

R⁴ is hydrogen, methyl, or ethyl;

(e) compound A having the formula:

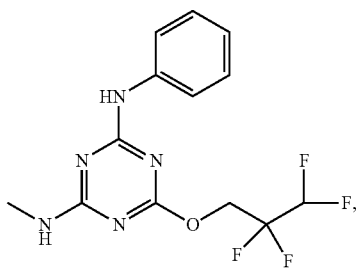

A or a pharmaceutically acceptable salt thereof, (f) compound B having the formula:

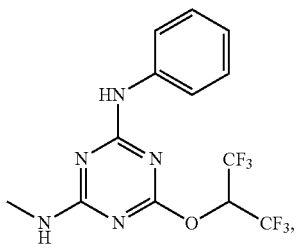

B or a pharmaceutically acceptable salt thereof;

(g) compound C having the formula:

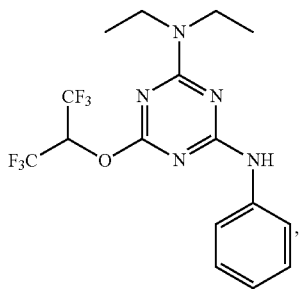

C or a pharmaceutically acceptable salt thereof;

(h) compound D having the formula:

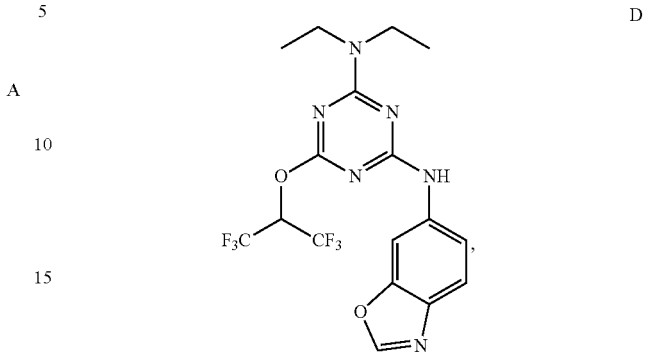

D or a pharmaceutically acceptable salt thereof, and (i) compound E having the formula:

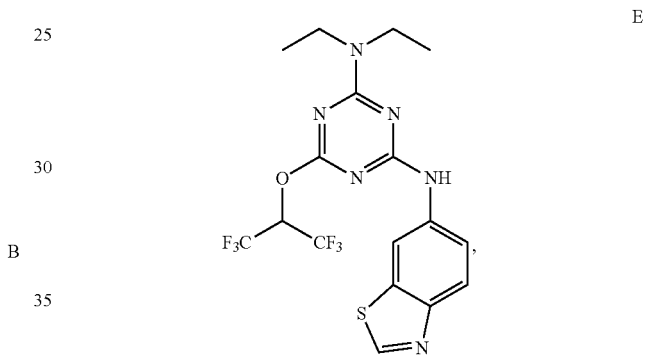

E or a pharmaceutically acceptable salt thereof.

Embodiment 14. A method of treating a patient with dry eye disease comprising: topically administering to an eye of the patient an amount of an active agent producing (i) about 500 nM or more in the tear fluid of the eye about 30 minutes to about 3 hours after administration, or (ii) about 10 nM or more in the tear fluid of the eye about 4 hours to about to about 12 hours after administration; wherein the active agent is selected from a group consisting of:

(a) a compound of Formula (I), or a pharmaceutically acceptable salt thereof:

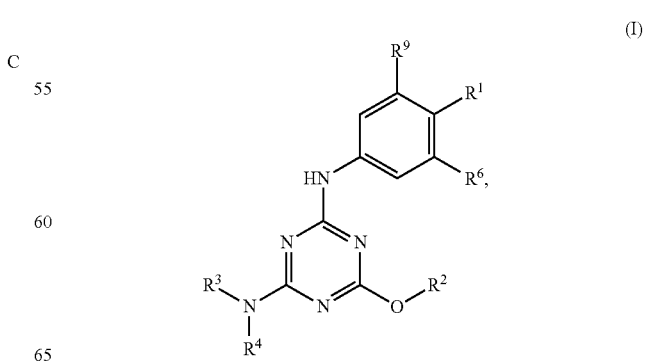

(I)

wherein:

R¹ is:
(i) hydrogen;
(ii) R¹ and R⁶ are joined to form, together with the atoms to which they are attached, a substituted or unsubstituted $C_8$-$C_{10}$ heterocycloalkyl or a substituted or unsubstituted $C_8$-$C_{10}$ heteroaryl; or
(iii) R¹ and R⁹ are joined to form, together with the atoms to which they are attached, a substituted or unsubstituted $C_8$-$C_{10}$ heterocycloalkyl or a substituted or unsubstituted $C_8$-$C_{10}$ heteroaryl;

R² is a $C_2$-$C_4$ haloalkyl;
R³ is hydrogen or a $C_1$-$C_3$ alkyl;
R⁴ is hydrogen or a $C_1$-$C_3$ alkyl;

R⁶ is:
(i) hydrogen; or
(ii) R¹ and R⁶ are joined to form, together with the atoms to which they are attached, a substituted or unsubstituted $C_8$-$C_{10}$ heterocycloalkyl or a substituted or unsubstituted $C_8$-$C_{10}$ heteroaryl; and R⁹ is:
(i) hydrogen; or
(ii) R¹ and R⁹ are joined to form, together with the atoms to which they are attached, a substituted or unsubstituted $C_8$-$C_{10}$ heterocycloalkyl or a substituted or unsubstituted $C_8$-$C_{10}$ heteroaryl;

(b) a compound of Formula (II), or a pharmaceutically acceptable salt thereof:

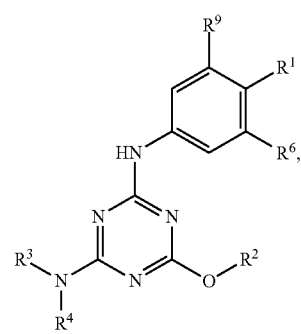

(II)

wherein:
R¹ and R⁶ are joined to form, together with the atoms to which they are attached, a $C_9$ heteroaryl, wherein R¹ and R⁶ are —X1-CH—X2-, wherein X1 and X2 are each independently —O—, —N═, or —S—;
R¹ and R⁹ are joined to form, together with the atoms to which they are attached, a $C_9$ heteroaryl, wherein R¹ and R⁹ are —X1-CH—X2-, wherein X1 and X2 are each independently —O—, —N═, or —S—;
R² is —CH(CF₃)₂ or —CH₂CF₂CF₂H;
R³ is hydrogen, methyl, or ethyl;
R⁴ is hydrogen, methyl, or ethyl;
R⁶ is:
(i) hydrogen; or
(ii) R¹ and R⁶ are joined to form, together with the atoms to which they are attached, a $C_9$ heteroaryl wherein R¹ and R⁶ are —X1-CH—X2- and X1 is —O— or —N═ and X2 is ═N— or —O—; and R⁹ is:
(i) hydrogen; or
(ii) R¹ and R⁹ are joined to form, together with the atoms to which they are attached, a $C_9$ heteroaryl wherein R¹ and R⁹ are —X1-CH—X2- and X1 is —O— or —N═ and X2 is ═N— or —O—:

(c) a compound of Formula (III), or a pharmaceutically acceptable salt thereof:

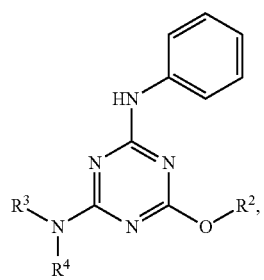

(III)

wherein:
R² is —CH(CF₃)₂ or —CH₂CF₂CF₂H;
R³ is hydrogen, methyl, or ethyl; and
R⁴ is hydrogen, methyl, or ethyl;

(d) a compound of Formula (IV), or a pharmaceutically acceptable salt thereof:

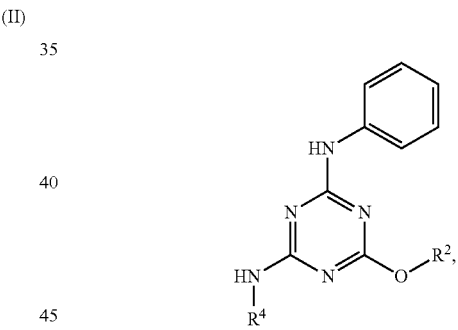

(IV)

wherein:
R² is —CH(CF₃)₂ or —CH₂CF₂CF₂H; and
R⁴ is hydrogen, methyl, or ethyl;

(e) compound A having the formula:

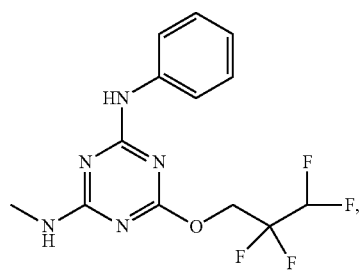

A or a pharmaceutically acceptable salt thereof;

(f) compound B having the formula:

B
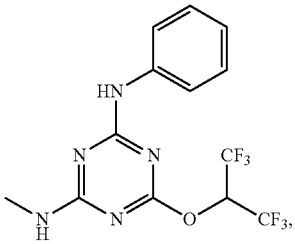

or a pharmaceutically acceptable salt thereof;

(g) compound C having the formula:

C
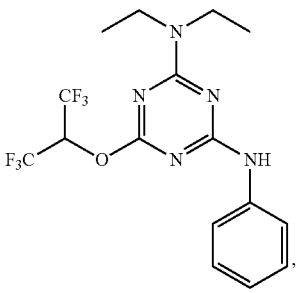

or a pharmaceutically acceptable salt thereof;

(h) compound D having the formula:

D
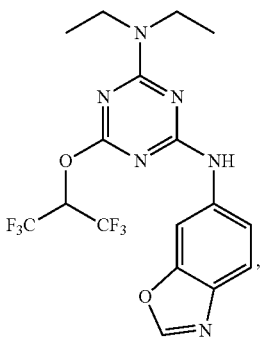

or a pharmaceutically acceptable salt thereof, and (i) compound E having the formula:

E
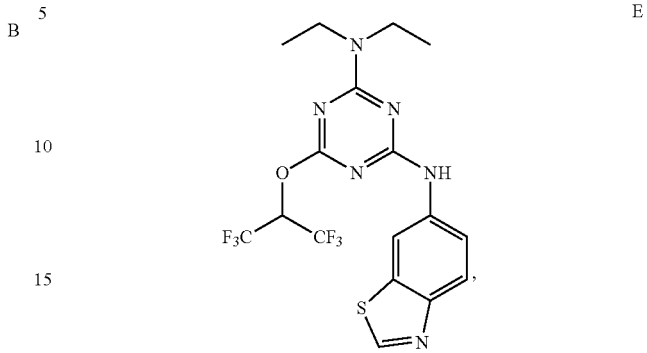

or a pharmaceutically acceptable salt thereof.

Embodiment 15. The method of embodiment 13 or 14, wherein the therapeutically effective amount of the active agent provides a concentration of (i) about 500 nM to about 5,000 nM about 1 hour to about 3 hours after administration, or (ii) about 10 nM to about 2,000 nM about 4 hours to about 8 hours after administration.

Embodiment 16. The method of embodiment 13 or 14, wherein the therapeutically effective amount of the active agent provides a concentration of (i) about 500 nM to about 1,500 nM about 1 hour to about 3 hours after administration, or (ii) about 50 nM to about 500 nM about 5 hours to about 7 hours after administration.

Embodiment 17. The method of embodiment 13 or 14, wherein the therapeutically effective amount of the active agent provides a concentration of (i) about 1000 nM about 2 hours after administration, or (ii) about 100 nM about 6 hours after administration.

Embodiment 18. A method of increasing tear production in an eye of a patient in need thereof, the method comprising topically administering once per day or twice per day to the eye of the patient at least one active agent selected from a group consisting of:

(a) a compound of Formula (I), or a pharmaceutically acceptable salt thereof:

(I)
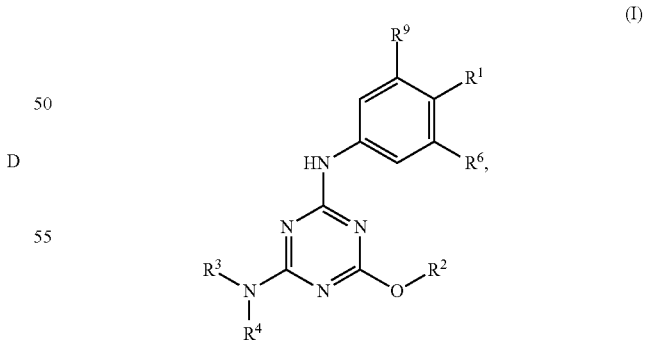

wherein:
$R^1$ is:
(i) hydrogen;
(ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; or (iii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;

$R^2$ is a $C_2$-$C_4$ haloalkyl;

$R^3$ is hydrogen or a $C_1$-$C_3$ alkyl;

$R^4$ is hydrogen or a $C_1$-$C_3$ alkyl;

$R^6$ is:

(i) hydrogen; or (ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; and $R^9$ is:

(i) hydrogen; or (ii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;

(b) a compound of Formula (II), or a pharmaceutically acceptable salt thereof:

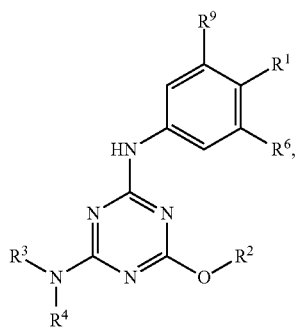

(II)

wherein:

$R^1$ and $R^6$ are joined to form, together with the atoms to which they are attached, a $C_9$ heteroaryl, wherein $R^1$ and $R^6$ are —X1-CH—X2-, wherein X1 and X2 are each independently —O—, —N=, or —S—;

$R^1$ and $R^9$ are joined to form, together with the atoms to which they are attached, a $C_9$ heteroaryl, wherein $R^1$ and $R^9$ are —X1-CH—X2-, wherein X1 and X2 are each independently —O—, —N=, or —S—;

$R^2$ is —CH(CF$_3$)$_2$ or —CH$_2$CF$_2$CF$_2$H;

$R^3$ is hydrogen, methyl, or ethyl;

$R^4$ is hydrogen, methyl, or ethyl;

$R^6$ is:

(i) hydrogen; or (ii) $R^1$ and $R^6$ are joined to form, together with the atoms to which they are attached, a $C_9$ heteroaryl wherein $R^1$ and $R^6$ are —X1-CH—X2- and X1 is —O— or —N= and X2 is =N— or —O—; and $R^9$ is:

(i) hydrogen; or (ii) $R^1$ and $R^9$ are joined to form, together with the atoms to which they are attached, a $C_9$ heteroaryl wherein $R^1$ and $R^9$ are —X1-CH—X2- and X1 is —O— or —N= and X2 is =N— or —O—:

(c) a compound of Formula (III), or a pharmaceutically acceptable salt thereof:

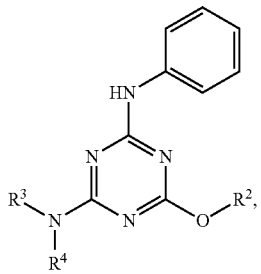

(III)

wherein:

$R^2$ is —CH(CF$_3$)$_2$ or —CH$_2$CF$_2$CF$_2$H;

$R^3$ is hydrogen, methyl, or ethyl; and $R^4$ is hydrogen, methyl, or ethyl;

(d) a compound of Formula (IV), or a pharmaceutically acceptable salt thereof:

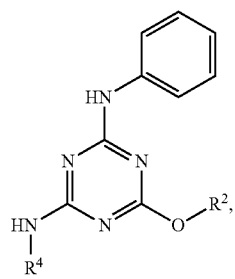

(IV)

wherein:

$R^2$ is —CH(CF$_3$)$_2$ or —CH$_2$CF$_2$CF$_2$H; and $R^4$ is hydrogen, methyl, or ethyl;

(e) compound A having the formula:

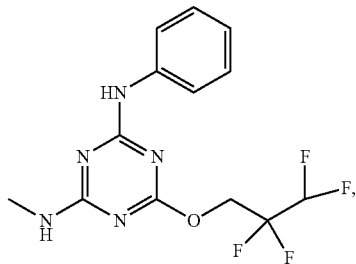

A or a pharmaceutically acceptable salt thereof, (f) compound B having the formula:

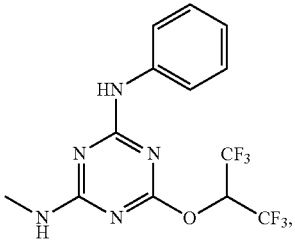

B or a pharmaceutically acceptable salt thereof;

(g) compound C having the formula:

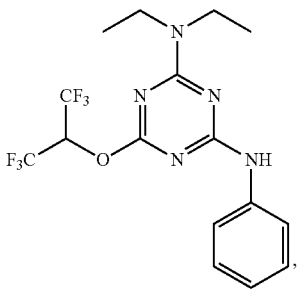

C or a pharmaceutically acceptable salt thereof;

(h) compound D having the formula:

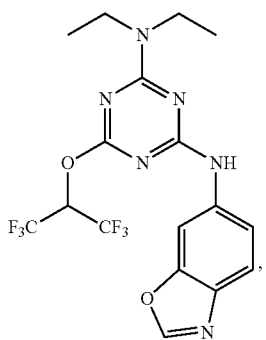

D or a pharmaceutically acceptable salt thereof, and (i) compound E having the formula:

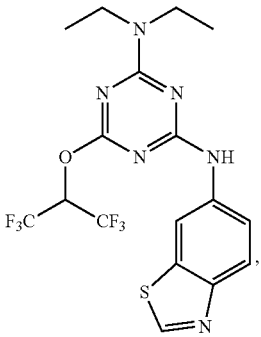

E or a pharmaceutically acceptable salt thereof.

Embodiment 19. A method of treating a patient with a dry eye disease comprising: topically administering once or twice per day to an eye of the patient an amount of at least one active agent effective to treat the dry eye disease; wherein the active agent is selected from a group consisting of:

(a) a compound of Formula (I), or a pharmaceutically acceptable salt thereof:

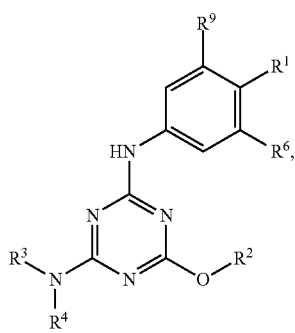

(I)

wherein:

$R^1$ is:

(i) hydrogen;

(ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; or (iii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;

$R^2$ is a $C_2$-$C_4$ haloalkyl;

$R^3$ is hydrogen or a $C_1$-$C_3$ alkyl;

$R^4$ is hydrogen or a $C_1$-$C_3$ alkyl;

$R^6$ is:

(i) hydrogen; or (ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; and R⁹ is:
(i) hydrogen; or
(ii) R¹ and R⁹ are joined to form, together with the atoms to which they are attached, a substituted or unsubstituted $C_8$-$C_{10}$ heterocycloalkyl or a substituted or unsubstituted $C_8$-$C_{10}$ heteroaryl;
(b) a compound of Formula (II), or a pharmaceutically acceptable salt thereof:

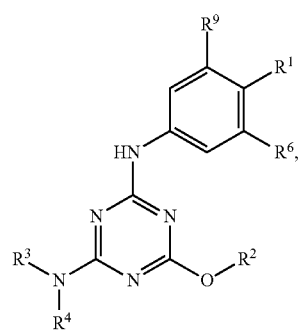

(II)

wherein:
R¹ and R⁶ are joined to form, together with the atoms to which they are attached, a $C_9$ heteroaryl, wherein R¹ and R⁶ are —X1-CH—X2-, wherein X1 and X2 are each independently —O—, —N═, or —S—;
R¹ and R⁹ are joined to form, together with the atoms to which they are attached, a $C_9$ heteroaryl, wherein R¹ and R⁹ are —X1-CH—X2-, wherein X1 and X2 are each independently —O—, —N═, or —S—;
R² is —CH(CF₃)₂ or —CH₂CF₂CF₂H;
R³ is hydrogen, methyl, or ethyl;
R⁴ is hydrogen, methyl, or ethyl;
R⁶ is:
(i) hydrogen; or
(ii) R¹ and R⁶ are joined to form, together with the atoms to which they are attached, a $C_9$ heteroaryl wherein R¹ and R⁶ are —X1-CH—X2- and X1 is —O— or —N═ and X2 is ═N— or —O—; and
R⁹ is:
(i) hydrogen; or
(ii) R¹ and R⁹ are joined to form, together with the atoms to which they are attached, a $C_9$ heteroaryl wherein R¹ and R⁹ are —X1-CH—X2- and X1 is —O— or —N═ and X2 is ═N— or —O—:
(c) a compound of Formula (III), or a pharmaceutically acceptable salt thereof:

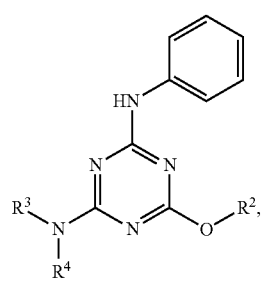

(III)

wherein:
R² is —CH(CF₃)₂ or —CH₂CF₂CF₂H;
R³ is hydrogen, methyl, or ethyl; and
R⁴ is hydrogen, methyl, or ethyl;
(d) a compound of Formula (IV), or a pharmaceutically acceptable salt thereof:

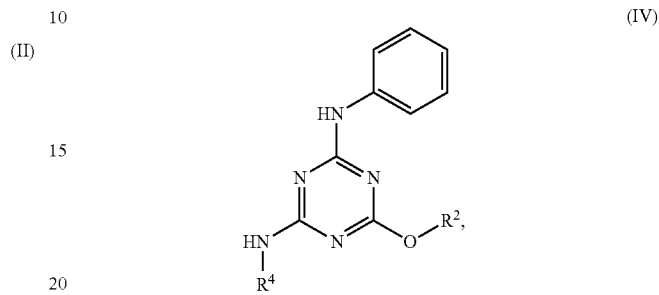

(IV)

wherein:
R² is —CH(CF₃)₂ or —CH₂CF₂CF₂H; and
R⁴ is hydrogen, methyl, or ethyl;
(e) compound A having the formula:

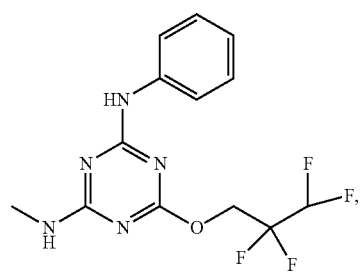

A or a pharmaceutically acceptable salt thereof;
(f) compound B having the formula:

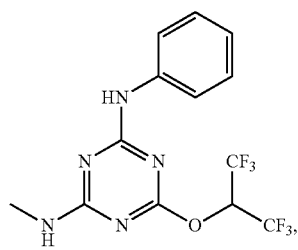

B or a pharmaceutically acceptable salt thereof;

(g) compound C having the formula:

C or a pharmaceutically acceptable salt thereof;

(h) compound D having the formula:

D or a pharmaceutically acceptable salt thereof, and (i) compound E having the formula:

E or a pharmaceutically acceptable salt thereof.

Embodiment 20. The method of any one of embodiments 1 to 19, wherein the active agent is the compound of Formula (I) or the pharmaceutically acceptable salt thereof.

Embodiment 21. The method of any one of embodiments 1 to 19, wherein the active agent is the compound of Formula (II) or the pharmaceutically acceptable salt thereof.

Embodiment 22. The method of any one of embodiments 1 to 19, wherein the active agent is the compound of Formula (III) or the pharmaceutically acceptable salt thereof.

Embodiment 23. The method any one of embodiments 1 to 19, wherein the active agent is the compound of Formula (IV) or the pharmaceutically acceptable salt thereof.

Embodiment 24. The method of any one of embodiments 1 to 19, wherein the active agent is Compound A or the pharmaceutically acceptable salt thereof.

Embodiment 25. The method of any one of embodiments 1 to 19, wherein the active agent is Compound B or the pharmaceutically acceptable salt thereof.

Embodiment 26. The method of any one of embodiments 1 to 19, wherein the active agent is Compound C or the pharmaceutically acceptable salt thereof.

Embodiment 27. The method of any one of embodiments 1 to 19, wherein the active agent is Compound D or the pharmaceutically acceptable salt thereof.

Embodiment 28. The method of any one of embodiments 1 to 19, wherein the active agent is Compound E or the pharmaceutically acceptable salt thereof.

Embodiment 29. The method of any one of embodiments 1 to 28, comprising topically administering the active agent to the conjunctiva of the eye.

Embodiment 30. The method of any one of embodiments 1 to 28, comprising topically administering the active agent to the conjunctival sac of the eye.

Embodiment 31. The method of any one of embodiments 1 to 30, wherein the active agent is administered once per day.

Embodiment 32. The method of any one of embodiments 1 to 30, wherein the active agent is administered twice per day.

Embodiment 33. The method of any one of embodiments 1 to 30, wherein the active agent is administered for about 14 days.

Embodiment 34. The method of any one of embodiments 1 to 30, wherein the active agent is administered for about one month.

Embodiment 35. The method of any one of embodiments 1 to 34, further comprising: co-administering one or more additional therapeutic agents in amounts effective to enhance the therapeutic effects of the active agent, wherein the additional therapeutic agents are selected from a group consisting of: an epithelial sodium channel inhibitor, a lymphocyte function-associated antigen-1 antagonist, an anti-inflammatory agent, a cholinergic agonist, a steroid, and an antibiotic.

Embodiment 36. The method of embodiment 35, wherein the epithelial sodium channel inhibitor is amiloride; wherein the lymphocyte function-associated antigen-1 antagonist is lifitegrast; wherein the anti-inflammatory agent is cyclosporine; wherein the cholinergic agonist is pilocarpine or cevimeline; and wherein the steroid is a corticosteroid.

Embodiment 37. The method of any one of embodiments 1 to 36, wherein the patient is a human.

Embodiment 38. The method of any one of embodiments 1 to 37, wherein the patient has an open-circuit transepithelial potential difference, in response to contact with different solutions, that is lower than that of a control.

Embodiment 39. The method of any one of embodiments 1 to 38, further comprising testing the change in the open-circuit transepithelial potential difference, in response to contact with different solutions, at the surface of the eye of the patient, and comparing the result to a control.

Embodiment 40. A topical pharmaceutical composition comprising at least about 5 micrograms of at least one active agent and a pharmaceutically acceptable carrier; wherein the active agent is selected from a group consisting of:

(a) a compound of Formula (I), or a pharmaceutically acceptable salt thereof:

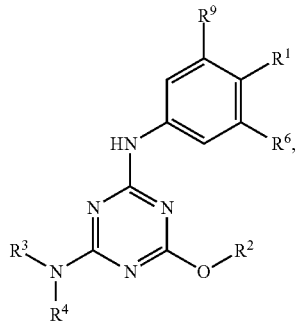

(I)

wherein:

R¹ is:
(i) hydrogen;
(ii) R¹ and R⁶ are joined to form, together with the atoms to which they are attached, a substituted or unsubstituted $C_8$-$C_{10}$ heterocycloalkyl or a substituted or unsubstituted $C_8$-$C_{10}$ heteroaryl; or
(iii) R¹ and R⁹ are joined to form, together with the atoms to which they are attached, a substituted or unsubstituted $C_8$-$C_{10}$ heterocycloalkyl or a substituted or unsubstituted $C_8$-$C_{10}$ heteroaryl;

R² is a $C_2$-$C_4$ haloalkyl;
R³ is hydrogen or a $C_1$-$C_3$ alkyl;
R⁴ is hydrogen or a $C_1$-$C_3$ alkyl;
R⁶ is:
(i) hydrogen; or
(ii) R¹ and R⁶ are joined to form, together with the atoms to which they are attached, a substituted or unsubstituted $C_8$-$C_{10}$ heterocycloalkyl or a substituted or unsubstituted $C_8$-$C_{10}$ heteroaryl; and
R⁹ is:
(i) hydrogen; or
(ii) R¹ and R⁹ are joined to form, together with the atoms to which they are attached, a substituted or unsubstituted $C_8$-$C_{10}$ heterocycloalkyl or a substituted or unsubstituted $C_8$-$C_{10}$ heteroaryl;

(b) a compound of Formula (II), or a pharmaceutically acceptable salt thereof:

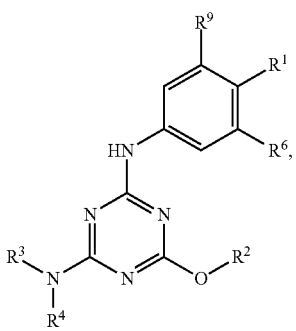

(II)

wherein:
R¹ and R⁶ are joined to form, together with the atoms to which they are attached, a $C_9$ heteroaryl, wherein R¹ and R⁶ are —X1-CH—X2-, wherein X1 and X2 are each independently —O—, —N═, or —S—;

R¹ and R⁹ are joined to form, together with the atoms to which they are attached, a $C_9$ heteroaryl, wherein R¹ and R⁹ are —X1-CH—X2-, wherein X1 and X2 are each independently —O—, —N═, or —S—;

R² is —CH(CF₃)₂ or —CH₂CF₂CF₂H;
R³ is hydrogen, methyl, or ethyl;
R⁴ is hydrogen, methyl, or ethyl;
R⁶ is:
(i) hydrogen; or
(ii) R¹ and R⁶ are joined to form, together with the atoms to which they are attached, a $C_9$ heteroaryl wherein R¹ and R⁶ are —X1-CH—X2- and X1 is —O— or —N═ and X2 is ═N— or —O—; and
R⁹ is:
(i) hydrogen; or
(ii) R¹ and R⁹ are joined to form, together with the atoms to which they are attached, a $C_9$ heteroaryl wherein R¹ and R⁹ are —X1-CH—X2- and X1 is —O— or —N═ and X2 is ═N— or —O—:

(c) a compound of Formula (III), or a pharmaceutically acceptable salt thereof:

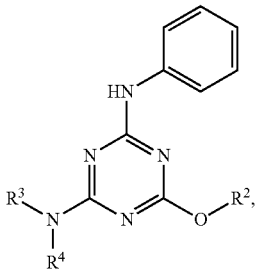

(III)

wherein:
R² is —CH(CF₃)₂ or —CH₂CF₂CF₂H;
R³ is hydrogen, methyl, or ethyl; and
R⁴ is hydrogen, methyl, or ethyl;

(d) a compound of Formula (IV), or a pharmaceutically acceptable salt thereof:

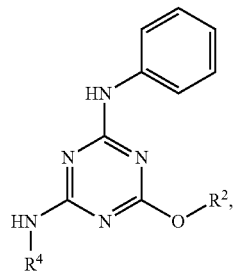

(IV)

wherein:
R² is —CH(CF₃)₂ or —CH₂CF₂CF₂H; and
R⁴ is hydrogen, methyl, or ethyl;

(e) compound A having the formula:

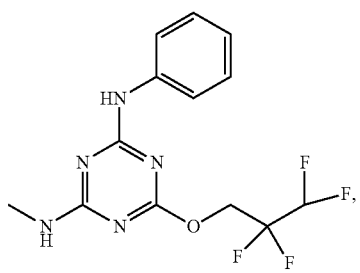

or a pharmaceutically acceptable salt thereof,
(f) compound B having the formula:

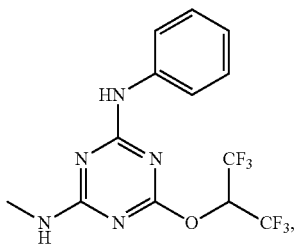

or a pharmaceutically acceptable salt thereof;
(g) compound C having the formula:

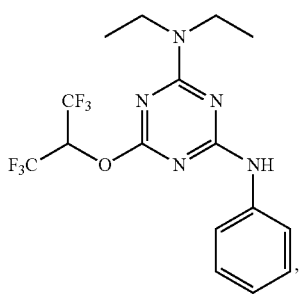

or a pharmaceutically acceptable salt thereof;
(h) compound D having the formula:

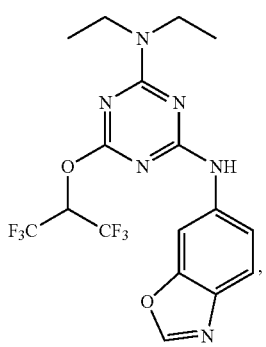

or a pharmaceutically acceptable salt thereof; and
(i) compound E having the formula:

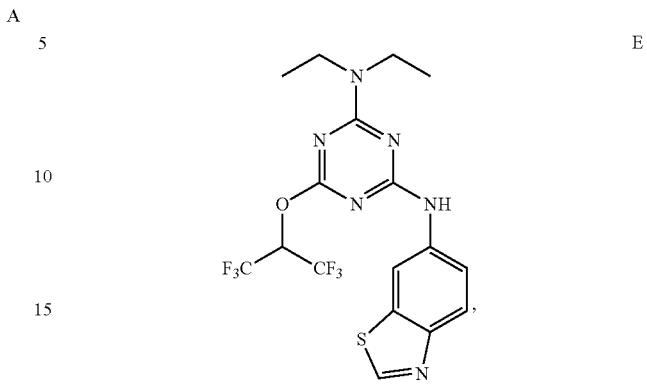

or a pharmaceutically acceptable salt thereof.

Embodiment 41. The composition of embodiment 40 comprising from about 5 micrograms to about 1 gram of the active agent.

Embodiment 42. The composition of embodiment 40 comprising from about 5 micrograms to about 1 milligram of the active agent.

Embodiment 43. The composition of embodiment 40 comprising from about 5 micrograms to about 500 micrograms.

Embodiment 44. The composition of embodiment 40 comprising from about 5 micrograms to about 35 micrograms of the active agent.

Embodiment 45. The composition of embodiment 40 comprising about 10 micrograms.

Embodiment 46. A topical pharmaceutical composition comprising from about 1 nanomole to about 25 nmoles per 0.5 mL of an active agent and a pharmaceutically acceptable excipient; wherein the active agent is selected from a group consisting of:
(a) a compound of Formula (I), or a pharmaceutically acceptable salt thereof:

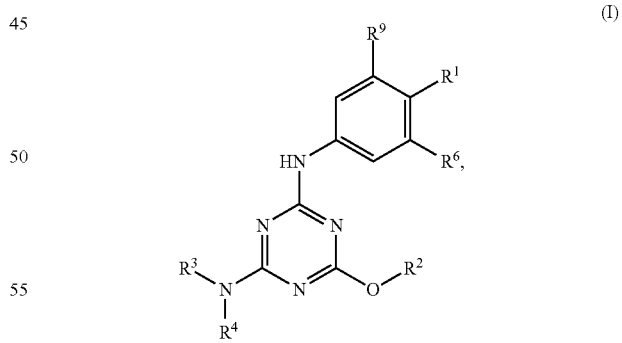

wherein:
$R^1$ is:
(i) hydrogen;
(ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; or
(iii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;

$R^2$ is a $C_2$-$C_4$ haloalkyl;

$R^3$ is hydrogen or a $C_1$-$C_3$ alkyl;

$R^4$ is hydrogen or a $C_1$-$C_3$ alkyl;

$R^6$ is:

(i) hydrogen; or (ii) $R^1$ and $R^6$ are joined to form, together with the atoms to which they are attached, a substituted or unsubstituted $C_8$-$C_{10}$ heterocycloalkyl or a substituted or unsubstituted $C_8$-$C_{10}$ heteroaryl; and $R^9$ is:

(i) hydrogen; or (ii) $R^1$ and $R^9$ are joined to form, together with the atoms to which they are attached, a substituted or unsubstituted $C_8$-$C_{10}$ heterocycloalkyl or a substituted or unsubstituted $C_8$-$C_{10}$ heteroaryl;

(b) a compound of Formula (II), or a pharmaceutically acceptable salt thereof:

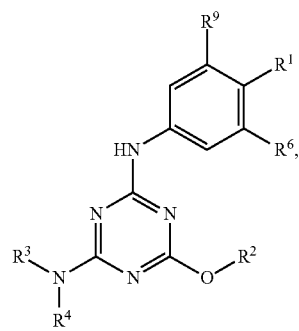

(II)

wherein:

$R^1$ and $R^6$ are joined to form, together with the atoms to which they are attached, a $C_9$ heteroaryl, wherein $R^1$ and $R^6$ are —X1-CH—X2-, wherein X1 and X2 are each independently —O—, —N=, or —S—;

$R^1$ and $R^9$ are joined to form, together with the atoms to which they are attached, a $C_9$ heteroaryl, wherein $R^1$ and $R^9$ are —X1-CH—X2-, wherein X1 and X2 are each independently —O—, —N=, or —S—;

$R^2$ is —CH(CF$_3$)$_2$ or —CH$_2$CF$_2$CF$_2$H;

$R^3$ is hydrogen, methyl, or ethyl;

$R^4$ is hydrogen, methyl, or ethyl;

$R^6$ is:

(i) hydrogen; or (ii) $R^1$ and $R^6$ are joined to form, together with the atoms to which they are attached, a $C_9$ heteroaryl wherein $R^1$ and $R^6$ are —X1-CH—X2- and X1 is —O— or —N= and X2 is =N— or —O—; and $R^9$ is:

(i) hydrogen; or (ii) $R^1$ and $R^9$ are joined to form, together with the atoms to which they are attached, a $C_9$ heteroaryl wherein $R^1$ and $R^9$ are —X1-CH—X2- and X1 is —O— or —N= and X2 is =N— or —O—:

(c) a compound of Formula (III), or a pharmaceutically acceptable salt thereof:

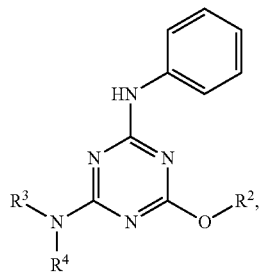

(III)

wherein:

$R^2$ is —CH(CF$_3$)$_2$ or —CH$_2$CF$_2$CF$_2$H;

$R^3$ is hydrogen, methyl, or ethyl; and $R^4$ is hydrogen, methyl, or ethyl;

(d) a compound of Formula (IV), or a pharmaceutically acceptable salt thereof:

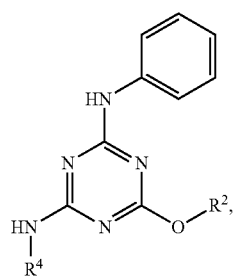

(IV)

wherein:

$R^2$ is —CH(CF$_3$)$_2$ or —CH$_2$CF$_2$CF$_2$H; and $R^4$ is hydrogen, methyl, or ethyl;

(e) compound A having the formula:

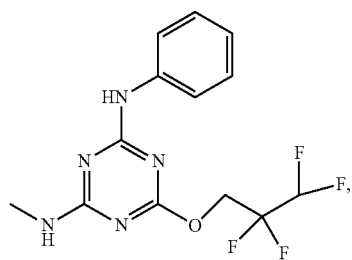

A or a pharmaceutically acceptable salt thereof;

(f) compound B having the formula:

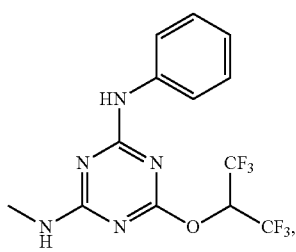

B or a pharmaceutically acceptable salt thereof;
(g) compound C having the formula:

C or a pharmaceutically acceptable salt thereof;
(h) compound D having the formula:

D or a pharmaceutically acceptable salt thereof; and
(i) compound E having the formula:

E or a pharmaceutically acceptable salt thereof.

Embodiment 47. The composition of embodiment 46 comprising from about 1 nanomole to about 15 nmoles per 0.5 mL of the active agent.

Embodiment 48. The composition of embodiment 46 comprising from about 2 nanomoles to about 10 nmoles per 0.5 mL of the active agent.

Embodiment 49. The composition of embodiment 46 comprising about 3 nanomoles per 0.5 mL of the active agent.

Embodiment 50. The composition of any one of embodiments 40 or 49, wherein the topical pharmaceutical composition is a liquid pharmaceutical composition.

Embodiment 51. The composition of embodiment 50, wherein the liquid pharmaceutical composition is a solution, a suspension, or an emulsion.

Embodiment 52. The composition of embodiment 50, wherein the liquid pharmaceutical composition is an aqueous solution.

Embodiment 53. The composition of embodiment 50, wherein the liquid pharmaceutical composition is a suspension; and wherein the compound is micronized.

Embodiment 54. The composition of any one of embodiments 40 to 53, wherein the composition further comprises a pharmaceutically acceptable excipient.

Embodiment 55. The composition of embodiment 54, wherein the pharmaceutically acceptable excipient is a stabilizer, a co-solvent, or a combination thereof.

Embodiment 56. The composition of any one of embodiments 40 to 55, wherein the active agent is the compound of Formula (I) or the pharmaceutically acceptable salt thereof.

Embodiment 57. The composition of any one of embodiments 40 to 55, wherein the active agent is the compound of Formula (II) or the pharmaceutically acceptable salt thereof.

Embodiment 58. The composition of any one of embodiments 40 to 55, wherein the active agent is the compound of Formula (III) or the pharmaceutically acceptable salt thereof.

Embodiment 59. The composition of any one of embodiments 40 to 55, wherein the pharmaceutical composition comprises the compound of Formula (IV) or the pharmaceutically acceptable salt thereof.

Embodiment 60. The composition of any one of embodiments 40 to 55, wherein the active agent is Compound A or the pharmaceutically acceptable salt thereof.

Embodiment 61. The composition of any one of embodiments 40 to 55, wherein the active agent is Compound B or the pharmaceutically acceptable salt thereof.

Embodiment 62. The composition of any one of embodiments 40 to 55, wherein the active agent is Compound C or the pharmaceutically acceptable salt thereof.

Embodiment 63. The composition of any one of embodiments 40 to 55, wherein the active agent is Compound D or the pharmaceutically acceptable salt thereof.

Embodiment 64. The composition of any one of embodiments 40 to 55, wherein the active agent is Compound E or the pharmaceutically acceptable salt thereof.

Embodiment 65. An eye dropper for delivering a drop of a topical pharmaceutical composition to the eye of a patient; wherein the eye dropper comprises the topical composition of any one of embodiments 40 to 64.

Embodiment 66. The eye dropper of embodiment 65 having a volume sufficient to house 1 to 25 drops of the composition.

Embodiment 67. The eye dropper of embodiment 65 having a volume sufficient to house 1 to 15 drops of the composition.

Embodiment 68. The eye dropper of embodiment 65 having a volume sufficient to house 1 to 10 drops of the composition.

Embodiment 69. A kit comprising the eye dropper of any one of embodiments 65 to 68 and instructions for use.

Embodiment 70. The kit of embodiment 69, comprising seven eye droppers, fourteen eye droppers, twenty-eight eye droppers, or fifty-six eye droppers.

Embodiment 71. A kit comprising an eye dropper, a container which comprises the topical pharmaceutical composition of any one of embodiments 40 to 64, and instructions for use.

Embodiment 72. The kit of embodiment 71, comprising one eye dropper and one container; wherein the container comprises one dose of the composition.

Embodiment 73. The kit of embodiment 71, comprising two eye droppers and one container; wherein the container comprises two doses of the composition.

Embodiment 74. The kit of embodiment 71, comprising two eye droppers and two containers; wherein each container comprises one dose of the composition.

Embodiment 75. The kit of embodiment 71, comprising seven eye droppers and seven containers; wherein each container comprises one dose of the composition.

Embodiment 76. The kit of embodiment 71, comprising fourteen eye droppers and seven containers; wherein each container comprises two doses of the composition.

Embodiment 77. The kit of embodiment 71, comprising fourteen eye droppers and fourteen containers; wherein each container comprises one dose of the composition.

Embodiment 78. A method of identifying a patient for treatment with a modulator of ocular surface membrane transport, the method comprising the steps of:
  (i) measuring a change in an open-circuit transepithelial potential difference, in response to contact with different solutions, at an ocular surface of the patient;
  (ii) comparing the change in the open-circuit transepithelial potential difference, in response to contact with different solutions, to a control; and
  (iii) identifying that the patient should be treated with the modulator of ocular surface membrane transport if the change in the open-circuit transepithelial potential difference is lower than that of the control.

Embodiment 79. The method of embodiment 78, wherein the ocular surface membrane transport is an ion transporter or a biomolecule transporter.

Embodiment 80. The method of embodiment 79, wherein the ion transporter is a chloride transporter, a potassium transporter, or a bicarbonate transporter; and wherein the biomolecule transporter is a glucose transporter or a urea transporter.

Embodiment 81. The method of embodiment 79, further comprising treating the patient with a therapeutically effective amount of the modulator of ocular surface membrane transport.

Embodiment 82. The method of embodiment 79, wherein the modulator of ocular surface membrane transport is a CFTR agonist, a calcium-activated chloride channel activator, or an epithelial sodium channel (ENaC) inhibitor.

Embodiment 83. The method of embodiment 79, wherein the modulator of ocular surface membrane transport is a pharmaceutical composition of claim 46.

Embodiment 84. A method of identifying a patient for treatment with a modulator of intracellular signaling, the method comprising the steps of:
  (i) measuring a change in an open-circuit transepithelial potential difference, in response to contact with different solutions, at an ocular surface of the patient;
  (ii) comparing the change in the open-circuit transepithelial potential difference, in response to contact with different solutions, to a control; and
  (iii) identifying that the patient should be treated with the modulator of intracellular signaling if the change in the open-circuit transepithelial potential difference is lower than that of the control.

Embodiment 85. The method of embodiment 84, wherein the modulator of intracellular signaling is cAMP, cGMP, or calcium signaling; wherein the modulator directly or indirectly modulates intracellular signaling.

Embodiment 86. The method of embodiment 84, further comprising treating the patient by administering a therapeutically effective amount of the pharmaceutical composition of claim 39 or 45.

Embodiment 87. The method of any one of embodiments, 78 to 86, wherein the ocular surface is the cornea or the conjunctiva.

What is claimed is:

1. A method of treating a patient in need of increased tear production, the method comprising:
topically administering to an eye of the patient at least about 5 micrograms of compound A having formula:

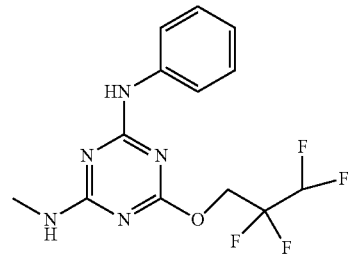 [SMILES: CNc1nc(Nc2ccccc2)nc(OCC(F)(F)C(F)F)n1]

or a pharmaceutical acceptable salt thereof.

2. The method of claim 1, wherein the patient has a dry eye disease.

3. The method of claim 1, wherein the topically administering is effective to produce a concentration of compound A of at least about 500 nM in the tear fluid of the eye at about 1 hour to about 12 hours following administration.

4. A method of treating a patient with dry eye disease, the method comprising topically administering once or twice per day to an eye of the patient an effective amount of compound A having the formula:

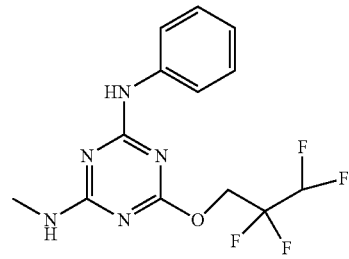 [SMILES: CNc1nc(Nc2ccccc2)nc(OCC(F)(F)C(F)F)n1]

or a pharmaceutical acceptable salt thereof.

5. The method of claim 4, wherein the topically administering is effective to produce a concentration of Compound A of at least about 500 nM in the tear fluid of the eye at about 1 hour to about 12 hours following administration.

6. The method of claim 4, comprising administering once or twice per day to the eye of the patient at least about 5 micrograms of compound A.

7. The method of claim 4, wherein the topically administering is effective to increase tear production in the eye of the patient.

8. A method of treating a patient with dry eye disease, the method comprising topically administering to an eye of the patient at least about 5 micrograms of compound A having formula:

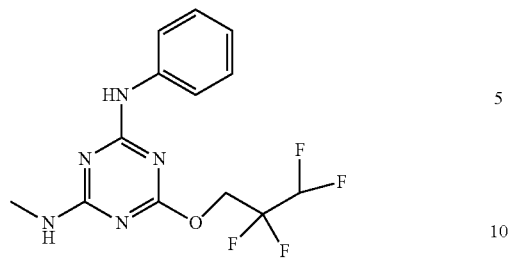

or a pharmaceutical acceptable salt thereof.

9. The method of claim 8, wherein the topically administering is effective to produce a concentration of compound A of at least about 500 nM in the tear fluid of the eye at about 1 hour to about 12 hours following administration.

10. The method of claim 8, wherein the topically administering is effective to increase tear production in the eye of the patient.

* * * * *

UNITED STATES PATENT AND TRADEMARK OFFICE
CERTIFICATE OF CORRECTION

| | | |
|---|---|---|
| PATENT NO. | : 11,839,616 B2 | Page 1 of 1 |
| APPLICATION NO. | : 16/641621 | |
| DATED | : December 12, 2023 | |
| INVENTOR(S) | : Alan S. Verkman et al. | |

It is certified that error appears in the above-identified patent and that said Letters Patent is hereby corrected as shown below:

In the Specification

<u>Column 1, Line 15:</u>
Delete "EY13574,"

Signed and Sealed this
Twelfth Day of August, 2025

Coke Morgan Stewart
*Acting Director of the United States Patent and Trademark Office*